(12) United States Patent
Bonutti et al.

(10) Patent No.: US 9,439,642 B2
(45) Date of Patent: Sep. 13, 2016

(54) METHODS AND DEVICES FOR UTILIZING BONDABLE MATERIALS

(75) Inventors: Peter M. Bonutti, Effingham, IL (US); Matthew J. Cremens, Effingham, IL (US); Justin E. Beyers, Effingham, IL (US)

(73) Assignee: P Tech, LLC, Effingham, IL (US)

( * ) Notice: Subject to any disclaimer, the term of this patent is extended or adjusted under 35 U.S.C. 154(b) by 8 days.

(21) Appl. No.: 12/711,540

(22) Filed: Feb. 24, 2010

(65) Prior Publication Data

US 2010/0211120 A1   Aug. 19, 2010

Related U.S. Application Data

(63) Continuation-in-part of application No. 12/202,210, filed on Aug. 29, 2008, now Pat. No. 8,496,657, which is a continuation-in-part of application No. 11/416,618, filed on May 3, 2006, now Pat. No. 7,967,820, and a continuation-in-part of application No. 11/689,670, filed on Mar. 22, 2007, and a continuation-in-part of application No. 11/671,556, filed on Feb. 6, 2007.

(60) Provisional application No. 61/155,133, filed on Feb. 24, 2009.

(51) Int. Cl.
*A61B 17/72* (2006.01)
*A61B 17/04* (2006.01)
(Continued)

(52) U.S. Cl.
CPC ........... *A61B 17/0401* (2013.01); *A61B 17/68* (2013.01); *A61B 17/7059* (2013.01); *A61B 17/7233* (2013.01); *A61B 17/7266* (2013.01); *A61B 17/866* (2013.01); *A61B 17/8685* (2013.01); *A61B 17/88* (2013.01); *A61B 17/8872* (2013.01); *A61F 2/30* (2013.01); *A61F 2/46* (2013.01); *A61L 24/001* (2013.01); *A61L 24/046* (2013.01); *A61B 17/11* (2013.01);
(Continued)

(58) Field of Classification Search
CPC ................... A61B 17/72–17/7291; A61B 17/80–17/8095; A61B 17/84–17/8695
USPC ........................... 606/62–68, 280–331, 86 B
See application file for complete search history.

(56) References Cited

U.S. PATENT DOCUMENTS

| 319,296 A | 6/1885 | Molesworth |
|---|---|---|
| 668,878 A | 2/1901 | Jensen |

(Continued)

FOREIGN PATENT DOCUMENTS

| CA | 2641580 | 8/2007 |
|---|---|---|
| CA | 2680827 | 9/2008 |

(Continued)

OTHER PUBLICATIONS

Copending U.S. Appl. No. 11/461,110, Request for Continued Examination Mar. 12, 2008.

(Continued)

*Primary Examiner* — Jan Christopher Merene
*Assistant Examiner* — Steven Cotroneo

(57) ABSTRACT

The invention primarily relates to fastening and stabilizing tissues, implants, and/or bondable materials, such as the fastening of a tissue and/or implant to a bondable material, the fastening of an implant to tissue, and/or the fastening of an implant to another implant. This may involve using an energy source to bond and/or mechanically to stabilize a tissue, an implant, a bondable material, and/or other biocompatible material. The invention may also relate to the use of an energy source to remove and/or install an implant and/or bondable material or to facilitate solidification and/or polymerization of bondable material.

28 Claims, 34 Drawing Sheets

(51) Int. Cl.

| | | |
|---|---|---|
| *A61B 17/68* | (2006.01) | |
| *A61B 17/70* | (2006.01) | |
| *A61B 17/86* | (2006.01) | |
| *A61B 17/88* | (2006.01) | |
| *A61F 2/30* | (2006.01) | |
| *A61F 2/46* | (2006.01) | |
| *A61L 24/00* | (2006.01) | |
| *A61L 24/04* | (2006.01) | |
| *A61B 17/11* | (2006.01) | |
| *A61B 17/32* | (2006.01) | |
| *A61B 17/00* | (2006.01) | |
| *A61F 2/08* | (2006.01) | |
| *A61F 2/32* | (2006.01) | |
| *A61F 2/34* | (2006.01) | |
| *A61F 2/36* | (2006.01) | |
| *A61F 2/38* | (2006.01) | |
| *A61F 2/40* | (2006.01) | |
| *A61F 2/42* | (2006.01) | |
| *A61F 2/44* | (2006.01) | |
| *A61F 2/06* | (2013.01) | |
| *A61F 2/28* | (2006.01) | |

(52) U.S. Cl.
CPC ........ *A61B17/1128* (2013.01); *A61B 17/1146* (2013.01); *A61B 17/320068* (2013.01); *A61B 17/8836* (2013.01); *A61B 2017/005* (2013.01); *A61B 2017/044* (2013.01); *A61B 2017/0409* (2013.01); *A61B 2017/1107* (2013.01); *A61F 2/0811* (2013.01); *A61F 2/3094* (2013.01); *A61F 2/30721* (2013.01); *A61F 2/30756* (2013.01); *A61F 2/32* (2013.01); *A61F 2/34* (2013.01); *A61F 2/36* (2013.01); *A61F 2/3603* (2013.01); *A61F 2/38* (2013.01); *A61F 2/3804* (2013.01); *A61F 2/389* (2013.01); *A61F 2/3859* (2013.01); *A61F 2/40* (2013.01); *A61F 2/4081* (2013.01); *A61F 2/4202* (2013.01); *A61F 2/44* (2013.01); *A61F 2/4455* (2013.01); *A61F 2/468* (2013.01); *A61F 2002/067* (2013.01); *A61F 2002/2817* (2013.01); *A61F 2002/30062* (2013.01); *A61F 2002/30065* (2013.01); *A61F 2002/30067* (2013.01); *A61F 2002/3068* (2013.01); *A61F 2002/30133* (2013.01); *A61F 2002/30451* (2013.01); *A61F 2002/30576* (2013.01); *A61F 2002/30604* (2013.01); *A61F 2002/30677* (2013.01); *A61F 2002/30785* (2013.01); *A61F 2002/30787* (2013.01); *A61F 2002/30878* (2013.01); *A61F 2002/30892* (2013.01); *A61F 2002/30894* (2013.01); *A61F 2002/30971* (2013.01); *A61F 2002/30973* (2013.01); *A61F 2002/3401* (2013.01); *A61F 2002/3403* (2013.01); *A61F 2002/444* (2013.01); *A61F 2002/4619* (2013.01); *A61F 2002/4683* (2013.01); *A61F 2210/0004* (2013.01); *A61F 2210/0071* (2013.01); *A61F 2220/0058* (2013.01); *A61F 2230/0015* (2013.01); *A61F 2250/0068* (2013.01); *A61F 2310/00011* (2013.01); *A61F 2310/00365* (2013.01); *A61F 2310/00383* (2013.01); *A61F 2310/00952* (2013.01)

(56) References Cited

U.S. PATENT DOCUMENTS

| | | | |
|---|---|---|---|
| 668,879 A | 2/1901 | Miller | |
| 702,789 A | 6/1902 | Gibson | |
| 862,712 A | 8/1907 | Collins | |
| 2,121,193 A | 12/1932 | Hanicke | |
| 2,187,852 A | 8/1936 | Friddle | |
| 2,178,840 A | 11/1939 | Lorenian | |
| 2,199,025 A | 4/1940 | Conn | |
| 2,235,419 A | 3/1941 | Callahan | |
| 2,248,054 A | 7/1941 | Becker | |
| 2,270,188 A | 1/1942 | Longfellow | |
| 2,518,276 A | 8/1950 | Braward | |
| 2,557,669 A | 6/1951 | Lloyd | |
| 2,566,499 A | 9/1951 | Richter | |
| 2,621,653 A | 12/1952 | Briggs | |
| 2,725,053 A | 11/1955 | Bambara | |
| 2,830,587 A | 4/1958 | Everett | |
| 3,204,635 A | 9/1965 | Voss et al. | |
| 3,347,234 A | 10/1967 | Voss | |
| 3,367,809 A | 2/1968 | Soloff | |
| 3,391,690 A | 7/1968 | Armao | |
| 3,477,429 A | 11/1969 | Sampson | |
| 3,513,848 A | 5/1970 | Winston et al. | |
| 3,518,993 A | 7/1970 | Blake | |
| 3,577,991 A | 5/1971 | Wilkinson | |
| 3,596,292 A | 8/1971 | Erb et al. | |
| 3,608,539 A | 9/1971 | Miller | |
| 3,625,220 A | 12/1971 | Engelsher | |
| 3,648,705 A | 3/1972 | Lary | |
| 3,653,388 A | 4/1972 | Tenckhoff | |
| 3,656,476 A | 4/1972 | Swinney | |
| 3,657,056 A | 4/1972 | Winston et al. | |
| 3,678,980 A | 7/1972 | Gutshall | |
| 3,709,218 A * | 1/1973 | Halloran | 606/64 |
| 3,711,347 A | 1/1973 | Wagner et al. | |
| 3,760,808 A | 9/1973 | Bleuer | |
| 3,788,318 A | 1/1974 | Kim et al. | |
| 3,789,852 A | 2/1974 | Kim et al. | |
| 3,802,438 A | 4/1974 | Wolvek | |
| 3,807,394 A | 4/1974 | Attenborough | |
| 3,809,075 A | 5/1974 | Matles | |
| 3,811,449 A | 5/1974 | Gravlee et al. | |
| 3,825,010 A | 7/1974 | McDonald | |
| 3,833,003 A | 9/1974 | Taricco | |
| 3,835,849 A | 9/1974 | McGuire | |
| 3,842,824 A | 10/1974 | Neufeld | |
| 3,857,396 A | 12/1974 | Hardwick | |
| 3,867,932 A | 2/1975 | Huene | |
| 3,875,652 A | 4/1975 | Arnold | |
| 3,898,992 A | 8/1975 | Balamuth | |
| 3,918,442 A | 11/1975 | Nikolaev et al. | |
| 3,968,800 A | 7/1976 | Vilasi | |
| 4,023,559 A | 5/1977 | Gaskell | |
| 4,064,566 A | 12/1977 | Fletcher et al. | |
| 4,089,071 A | 5/1978 | Kainberz et al. | |
| 4,156,574 A | 5/1979 | Boden | |
| 4,164,794 A | 8/1979 | Spector et al. | |
| 4,171,544 A | 10/1979 | Hench et al. | |
| 4,183,102 A | 1/1980 | Guiset | |
| 4,199,864 A | 4/1980 | Ashman | |
| 4,200,939 A | 5/1980 | Oser | |
| 4,210,148 A | 7/1980 | Stivala | |
| 4,213,816 A | 7/1980 | Morris | |
| 4,235,233 A | 11/1980 | Mouwen | |
| 4,235,238 A | 11/1980 | Ogiu et al. | |
| 4,257,411 A | 3/1981 | Cho | |
| 4,265,231 A | 5/1981 | Scheller, Jr. et al. | |
| 4,281,649 A * | 8/1981 | Derweduwen | 606/64 |
| 4,291,698 A | 9/1981 | Fuchs | |
| 4,309,488 A | 1/1982 | Heide et al. | |
| 4,320,762 A | 3/1982 | Bentov | |
| 4,351,069 A | 9/1982 | Ballintyn et al. | |
| 4,364,381 A | 12/1982 | Sher et al. | |
| 4,365,356 A | 12/1982 | Broemer et al. | |
| 4,388,921 A | 6/1983 | Sutter et al. | |
| 4,395,798 A | 8/1983 | McVey | |
| 4,409,974 A | 10/1983 | Freedland | |
| 4,414,166 A | 11/1983 | Charlson et al. | |
| 4,437,191 A | 3/1984 | Van der Zat et al. | |
| 4,437,362 A | 3/1984 | Hurst | |
| 4,444,180 A | 4/1984 | Schneider et al. | |
| 4,448,194 A | 5/1984 | DiGiovanni et al. | |

(56) References Cited

U.S. PATENT DOCUMENTS

| | | |
|---|---|---|
| 4,456,005 A | 6/1984 | Lichty |
| 4,461,281 A | 7/1984 | Carson |
| 4,493,317 A | 1/1985 | Klaue |
| 4,495,664 A | 1/1985 | Blanquaert |
| 4,501,031 A | 2/1985 | McDaniel et al. |
| 4,504,268 A | 3/1985 | Herlitze |
| 4,506,681 A | 3/1985 | Mundell |
| 4,514,125 A | 4/1985 | Stol |
| 4,526,173 A | 7/1985 | Sheehan |
| 4,532,926 A | 8/1985 | O'Holla |
| 4,535,772 A | 8/1985 | Sheehan |
| 4,547,327 A | 10/1985 | Bruins et al. |
| 4,556,350 A | 12/1985 | Bernhardt et al. |
| 4,566,138 A | 1/1986 | Lewis et al. |
| 4,589,868 A | 5/1986 | Dretler |
| 4,590,928 A | 5/1986 | Hunt et al. |
| 4,597,379 A | 7/1986 | Kihn et al. |
| 4,599,085 A | 7/1986 | Riess et al. |
| 4,601,893 A | 7/1986 | Cardinal |
| 4,606,335 A | 8/1986 | Wedeen |
| 4,621,640 A | 11/1986 | Mulhollan et al. |
| 4,630,609 A | 12/1986 | Chin |
| 4,632,101 A | 12/1986 | Freedland |
| 4,645,503 A | 2/1987 | Lin et al. |
| 4,657,460 A | 4/1987 | Bien |
| 4,659,268 A | 4/1987 | Del Mundo et al. |
| 4,662,063 A | 5/1987 | Collins et al. |
| 4,662,068 A | 5/1987 | Polonsky |
| 4,662,887 A | 5/1987 | Turner et al. |
| 4,669,473 A | 6/1987 | Richards et al. |
| 4,685,458 A | 8/1987 | Leckrone |
| 4,705,040 A | 11/1987 | Mueller et al. |
| 4,706,670 A | 11/1987 | Andersen et al. |
| 4,708,139 A | 11/1987 | Dunbar, IV |
| 4,713,077 A | 12/1987 | Small |
| 4,716,901 A | 1/1988 | Jackson et al. |
| 4,718,909 A | 1/1988 | Brown |
| 4,722,331 A | 2/1988 | Fox |
| 4,722,948 A | 2/1988 | Sanderson |
| 4,724,584 A | 2/1988 | Kasai |
| 4,738,255 A | 4/1988 | Goble et al. |
| 4,739,751 A | 4/1988 | Sapega et al. |
| 4,741,330 A | 5/1988 | Hayhurst |
| 4,749,585 A | 6/1988 | Greco et al. |
| 4,750,492 A | 6/1988 | Jacobs |
| 4,768,507 A | 9/1988 | Fischell |
| 4,772,286 A | 9/1988 | Goble et al. |
| 4,776,328 A | 10/1988 | Frey et al. |
| 4,776,738 A | 10/1988 | Winston |
| 4,776,851 A | 10/1988 | Bruchman et al. |
| 4,781,182 A | 11/1988 | Purnell et al. |
| 4,790,303 A | 12/1988 | Steffee |
| 4,792,336 A | 12/1988 | Hlavacek et al. |
| 4,817,591 A | 4/1989 | Klaue |
| 4,822,224 A | 4/1989 | Carl et al. |
| 4,823,794 A | 4/1989 | Pierce |
| 4,832,025 A | 5/1989 | Coates |
| 4,832,026 A | 5/1989 | Jones |
| 4,834,752 A | 5/1989 | Van Kampen |
| 4,841,960 A | 6/1989 | Garner |
| 4,843,112 A | 6/1989 | Gerhart |
| 4,846,812 A | 7/1989 | Walker et al. |
| 4,862,882 A | 9/1989 | Venturi et al. |
| 4,869,242 A | 9/1989 | Galluzzo |
| 4,870,957 A | 10/1989 | Goble et al. |
| 4,883,048 A | 11/1989 | Purnell et al. |
| 4,890,612 A | 1/1990 | Kensey |
| 4,895,148 A | 1/1990 | Bays et al. |
| 4,898,156 A | 2/1990 | Gatturna et al. |
| 4,899,729 A | 2/1990 | Gill et al. |
| 4,899,744 A | 2/1990 | Fujitsuka et al. |
| 4,901,721 A | 2/1990 | Hakki |
| 4,921,479 A | 5/1990 | Grayzel |
| 4,922,897 A | 5/1990 | Sapega et al. |
| 4,924,866 A | 5/1990 | Yoon |
| 4,932,960 A | 6/1990 | Green et al. |
| 4,935,026 A | 6/1990 | McFadden |
| 4,935,028 A | 6/1990 | Drews |
| 4,945,625 A | 8/1990 | Winston |
| 4,946,468 A | 8/1990 | Li |
| 4,954,126 A | 9/1990 | Wallsten |
| 4,955,910 A | 9/1990 | Bolesky |
| 4,957,498 A | 9/1990 | Caspari et al. |
| 4,961,741 A | 10/1990 | Hayhurst |
| 4,963,151 A | 10/1990 | Ducheyne et al. |
| 4,966,583 A | 10/1990 | Debbas |
| 4,968,315 A | 11/1990 | Gatturna |
| 4,969,888 A | 11/1990 | Scholten et al. |
| 4,969,892 A | 11/1990 | Burton et al. |
| 4,990,161 A | 2/1991 | Kampner |
| 4,994,071 A | 2/1991 | MacGregor |
| 4,997,445 A | 3/1991 | Hodorek |
| 4,998,539 A | 3/1991 | Delsanti |
| 5,002,550 A | 3/1991 | Li |
| 5,002,563 A | 3/1991 | Pyka et al. |
| 5,009,652 A | 4/1991 | Morgan et al. |
| 5,009,663 A | 4/1991 | Broome |
| 5,009,664 A | 4/1991 | Sievers |
| 5,013,316 A | 5/1991 | Goble et al. |
| 5,019,090 A | 5/1991 | Pinchuk |
| 5,021,059 A | 6/1991 | Kensey et al. |
| 5,035,713 A | 7/1991 | Friis |
| 5,037,404 A | 8/1991 | Gold et al. |
| 5,037,422 A | 8/1991 | Hayhurst et al. |
| 5,041,093 A | 8/1991 | Chu |
| 5,041,114 A * | 8/1991 | Chapman et al. ............... 606/62 |
| 5,041,129 A | 8/1991 | Hayhurst et al. |
| 5,046,513 A | 9/1991 | Gatturna et al. |
| 5,047,055 A | 9/1991 | Bao et al. |
| 5,051,049 A | 9/1991 | Wills |
| 5,053,046 A | 10/1991 | Janese |
| 5,053,047 A | 10/1991 | Yoon |
| 5,059,193 A | 10/1991 | Kuslich |
| 5,059,206 A | 10/1991 | Winters |
| 5,061,274 A | 10/1991 | Kensey |
| 5,061,286 A | 10/1991 | Lyle |
| 5,069,674 A | 12/1991 | Fearnot et al. |
| 5,078,731 A | 1/1992 | Hayhurst |
| 5,078,744 A | 1/1992 | Chvapil |
| 5,078,745 A | 1/1992 | Rhenter et al. |
| 5,084,050 A | 1/1992 | Draenert |
| 5,084,051 A | 1/1992 | Tormala et al. |
| 5,085,660 A | 2/1992 | Lin |
| 5,085,661 A | 2/1992 | Moss |
| 5,098,433 A | 3/1992 | Freedland |
| 5,098,434 A | 3/1992 | Serbousek |
| 5,098,436 A | 3/1992 | Ferrante et al. |
| 5,100,405 A | 3/1992 | McLaren |
| 5,100,417 A | 3/1992 | Cerier et al. |
| 5,102,417 A | 4/1992 | Palmaz |
| 5,102,421 A | 4/1992 | Anspach, Jr. |
| 5,108,399 A | 4/1992 | Eitenmuller et al. |
| 5,120,175 A | 6/1992 | Arbegast et al. |
| 5,123,520 A | 6/1992 | Schmid et al. |
| 5,123,914 A | 6/1992 | Cope |
| 5,123,941 A | 6/1992 | Lauren et al. |
| 5,133,732 A | 7/1992 | Wiktor |
| RE34,021 E | 8/1992 | Mueller |
| 5,141,520 A | 8/1992 | Goble et al. |
| 5,147,362 A | 9/1992 | Goble |
| 5,154,720 A | 10/1992 | Trott et al. |
| 5,156,613 A | 10/1992 | Sawyer |
| 5,156,616 A | 10/1992 | Meadows et al. |
| 5,158,566 A | 10/1992 | Pianetti |
| 5,158,934 A | 10/1992 | Ammann et al. |
| 5,163,960 A | 11/1992 | Bonutti |
| 5,171,251 A | 12/1992 | Bregen et al. |
| 5,176,682 A | 1/1993 | Chow |
| 5,179,964 A | 1/1993 | Cook |
| 5,180,388 A | 1/1993 | DiCarlo |
| 5,183,464 A | 2/1993 | Dubrul et al. |
| 5,192,287 A | 3/1993 | Fournier et al. |
| 5,192,326 A | 3/1993 | Bao et al. |
| 5,197,166 A | 3/1993 | Meier et al. |

(56) References Cited

U.S. PATENT DOCUMENTS

| | | | |
|---|---|---|---|
| 5,197,971 | A | 3/1993 | Bonutti |
| 5,203,784 | A | 4/1993 | Ross et al. |
| 5,203,787 | A | 4/1993 | Noblitt et al. |
| 5,208,950 | A | 5/1993 | Merritt |
| 5,209,776 | A | 5/1993 | Bass et al. |
| 5,217,493 | A | 6/1993 | Raad et al. |
| 5,219,359 | A | 6/1993 | McQuilkin et al. |
| 5,226,899 | A | 7/1993 | Lee et al. |
| 5,234,006 | A | 8/1993 | Eaton et al. |
| 5,234,425 | A | 8/1993 | Fogarty et al. |
| 5,236,438 | A | 8/1993 | Wilk |
| 5,236,445 | A | 8/1993 | Hayhurst |
| 5,242,902 | A | 9/1993 | Murphy et al. |
| 5,254,113 | A | 10/1993 | Wilk |
| 5,258,007 | A | 11/1993 | Spetzler et al. |
| 5,258,015 | A | 11/1993 | Li et al. |
| 5,258,016 | A | 11/1993 | DiPoto et al. |
| 5,266,325 | A | 11/1993 | Kuzma et al. |
| 5,269,783 | A | 12/1993 | Sander |
| 5,269,785 | A | 12/1993 | Bonutti |
| 5,269,809 | A | 12/1993 | Hayhurst et al. |
| 5,281,235 | A | 1/1994 | Haber et al. |
| 5,282,832 | A | 2/1994 | Toso et al. |
| 5,290,281 | A * | 3/1994 | Tschakaloff ............ 606/28 |
| 5,304,119 | A | 4/1994 | Balaban et al. |
| 5,306,280 | A | 4/1994 | Bregen et al. |
| 5,306,301 | A | 4/1994 | Graf et al. |
| 5,315,741 | A | 5/1994 | Dubberke |
| 5,318,570 | A | 6/1994 | Hood |
| 5,318,588 | A | 6/1994 | Horzewski et al. |
| 5,320,611 | A | 6/1994 | Bonutti |
| 5,324,308 | A | 6/1994 | Pierce |
| 5,328,480 | A | 7/1994 | Melker et al. |
| 5,329,846 | A | 7/1994 | Bonutti |
| 5,329,924 | A | 7/1994 | Bonutti |
| 5,330,468 | A | 7/1994 | Burkhart |
| 5,330,476 | A | 7/1994 | Hiot et al. |
| 5,330,486 | A | 7/1994 | Wilk |
| 5,336,231 | A | 8/1994 | Adair |
| 5,336,240 | A | 8/1994 | Metzler et al. |
| 5,339,799 | A | 8/1994 | Kami et al. |
| 5,349,956 | A | 9/1994 | Bonutti |
| 5,352,229 | A | 10/1994 | Goble et al. |
| 5,354,298 | A | 10/1994 | Lee et al. |
| 5,354,302 | A | 10/1994 | Ko |
| 5,366,480 | A | 11/1994 | Corriveau et al. |
| 5,370,646 | A | 12/1994 | Reese et al. |
| 5,370,660 | A | 12/1994 | Weinstein et al. |
| 5,372,146 | A | 12/1994 | Branch |
| 5,374,235 | A | 12/1994 | Ahrens |
| 5,376,126 | A | 12/1994 | Lin |
| 5,382,254 | A | 1/1995 | McGarry et al. |
| 5,383,883 | A | 1/1995 | Wilk et al. |
| 5,383,905 | A | 1/1995 | Golds et al. |
| 5,391,173 | A | 2/1995 | Wilk |
| 5,395,308 | A | 3/1995 | Fox et al. |
| 5,397,311 | A | 3/1995 | Walker et al. |
| 5,400,805 | A | 3/1995 | Warren |
| 5,403,312 | A | 4/1995 | Yates et al. |
| 5,403,348 | A | 4/1995 | Bonutti |
| 5,405,359 | A | 4/1995 | Pierce |
| 5,411,523 | A | 5/1995 | Goble |
| 5,413,585 | A | 5/1995 | Pagedas |
| 5,417,691 | A | 5/1995 | Hayhurst |
| 5,417,701 | A | 5/1995 | Holmes |
| 5,417,712 | A | 5/1995 | Whittaker et al. |
| 5,423,796 | A | 6/1995 | Shikhman et al. |
| 5,431,670 | A | 7/1995 | Holmes |
| 5,439,470 | A | 8/1995 | Li |
| 5,441,538 | A | 8/1995 | Bonutti |
| 5,443,512 | A | 8/1995 | Parr et al. |
| 5,447,503 | A | 9/1995 | Miller |
| 5,449,372 | A | 9/1995 | Schmaltz et al. |
| 5,449,382 | A | 9/1995 | Dayton |
| 5,451,235 | A | 9/1995 | Lock |
| 5,453,090 | A | 9/1995 | Martinez et al. |
| 5,456,722 | A | 10/1995 | McLeod et al. |
| 5,458,653 | A | 10/1995 | Davison |
| 5,462,561 | A | 10/1995 | Voda |
| 5,464,424 | A | 11/1995 | O'Donnell, Jr. |
| 5,464,426 | A | 11/1995 | Bonutti |
| 5,464,427 | A | 11/1995 | Curtis et al. |
| 5,470,337 | A | 11/1995 | Moss |
| 5,472,444 | A | 12/1995 | Huebner et al. |
| 5,474,554 | A | 12/1995 | Ku |
| 5,478,351 | A | 12/1995 | Meade et al. |
| 5,478,353 | A | 12/1995 | Yoon |
| 5,480,403 | A | 1/1996 | Lee et al. |
| 5,486,197 | A | 1/1996 | Le et al. |
| 5,487,844 | A | 1/1996 | Fujita |
| 5,488,958 | A | 2/1996 | Topel et al. |
| 5,496,292 | A | 3/1996 | Burnham |
| 5,496,335 | A | 3/1996 | Thomason et al. |
| 5,496,348 | A | 3/1996 | Bonutti |
| 5,500,000 | A | 3/1996 | Feagin et al. |
| 5,501,700 | A | 3/1996 | Hirata |
| 5,504,977 | A | 4/1996 | Weppner |
| 5,505,735 | A | 4/1996 | Li |
| 5,507,754 | A | 4/1996 | Green et al. |
| 5,522,844 | A | 6/1996 | Johnson |
| 5,522,845 | A | 6/1996 | Wenstrom, Jr. |
| 5,522,846 | A | 6/1996 | Bonutti |
| 5,527,341 | A | 6/1996 | Gogolewski et al. |
| 5,527,342 | A | 6/1996 | Pietrzak et al. |
| 5,527,343 | A | 6/1996 | Bonutti |
| 5,529,075 | A | 6/1996 | Clark |
| 5,531,759 | A | 7/1996 | Kensey et al. |
| 5,534,012 | A | 7/1996 | Bonutti |
| 5,534,028 | A | 7/1996 | Bao et al. |
| 5,540,718 | A | 7/1996 | Bartlett |
| 5,542,423 | A | 8/1996 | Bonutti |
| 5,545,178 | A | 8/1996 | Kensey et al. |
| 5,545,180 | A | 8/1996 | Le et al. |
| 5,545,206 | A | 8/1996 | Carson |
| 5,549,630 | A | 8/1996 | Bonutti |
| 5,549,631 | A | 8/1996 | Bonutti |
| 5,556,402 | A | 9/1996 | Xu |
| 5,569,252 | A | 10/1996 | Justin et al. |
| 5,569,305 | A | 10/1996 | Bonutti |
| 5,569,306 | A | 10/1996 | Thal |
| 5,573,517 | A | 11/1996 | Bonutti et al. |
| 5,573,538 | A | 11/1996 | Laboureau |
| 5,573,542 | A | 11/1996 | Stevens |
| 5,575,801 | A | 11/1996 | Habermeyer |
| 5,580,344 | A | 12/1996 | Hasson |
| 5,584,835 | A | 12/1996 | Greenfield |
| 5,584,860 | A | 12/1996 | Goble et al. |
| 5,584,862 | A | 12/1996 | Bonutti |
| 5,591,206 | A | 1/1997 | Moufarrege |
| 5,593,422 | A | 1/1997 | Muijs Van De Moer et al. |
| 5,593,425 | A | 1/1997 | Bonutti et al. |
| 5,593,625 | A | 1/1997 | Riebel et al. |
| 5,601,557 | A | 2/1997 | Hayhurst |
| 5,601,558 | A | 2/1997 | Torrie et al. |
| 5,601,595 | A | 2/1997 | Smith |
| 5,607,427 | A | 3/1997 | Tschakaloff |
| 5,609,595 | A | 3/1997 | Pennig |
| 5,618,314 | A | 4/1997 | Harwin et al. |
| 5,620,461 | A | 4/1997 | Muijs Van De Moer et al. |
| 5,626,612 | A | 5/1997 | Bartlett |
| 5,626,614 | A | 5/1997 | Hart |
| 5,626,718 | A | 5/1997 | Philippe et al. |
| 5,628,751 | A | 5/1997 | Sander et al. |
| 5,630,824 | A | 5/1997 | Hart |
| 5,634,926 | A | 6/1997 | Jobe |
| 5,635,784 | A | 6/1997 | Seale |
| 5,643,274 | A | 7/1997 | Sander et al. |
| 5,643,293 | A | 7/1997 | Kogasaka et al. |
| 5,643,295 | A | 7/1997 | Yoon |
| 5,643,321 | A | 7/1997 | McDevitt |
| 5,645,553 | A | 7/1997 | Kolesa et al. |
| 5,645,597 | A | 7/1997 | Krapiva |
| 5,645,599 | A | 7/1997 | Samani |
| 5,649,955 | A | 7/1997 | Hashimoto et al. |

(56) References Cited

U.S. PATENT DOCUMENTS

| | | |
|---|---|---|
| 5,649,963 A | 7/1997 | McDevitt |
| 5,651,377 A | 7/1997 | O'Donnell, Jr. |
| 5,658,313 A | 8/1997 | Thal |
| 5,660,225 A | 8/1997 | Saffran |
| 5,662,658 A | 9/1997 | Wenstrom, Jr. |
| 5,665,089 A | 9/1997 | Dall et al. |
| 5,665,109 A | 9/1997 | Yoon |
| 5,667,513 A | 9/1997 | Torrie et al. |
| 5,669,917 A | 9/1997 | Sauer et al. |
| 5,674,240 A | 10/1997 | Bonutti |
| 5,681,310 A | 10/1997 | Yuan et al. |
| 5,681,333 A | 10/1997 | Burkhart et al. |
| 5,681,351 A | 10/1997 | Jamiolkowski et al. |
| 5,681,352 A | 10/1997 | Clancy, III et al. |
| 5,685,820 A | 11/1997 | Riek et al. |
| 5,688,283 A | 11/1997 | Knapp |
| 5,690,654 A | 11/1997 | Ovil |
| 5,690,655 A | 11/1997 | Hart et al. |
| 5,690,676 A | 11/1997 | DiPoto et al. |
| 5,693,055 A | 12/1997 | Zahiri et al. |
| 5,697,950 A | 12/1997 | Fucci et al. |
| 5,702,397 A | 12/1997 | Gonle et al. |
| 5,702,462 A | 12/1997 | Oberlander |
| 5,707,395 A | 1/1998 | Li |
| 5,713,903 A | 2/1998 | Sander et al. |
| 5,713,921 A | 2/1998 | Bonutti |
| 5,718,717 A | 2/1998 | Bonutti |
| 5,720,747 A | 2/1998 | Burke |
| 5,720,753 A | 2/1998 | Sander et al. |
| 5,725,541 A | 3/1998 | Anspach, III et al. |
| 5,725,556 A | 3/1998 | Moser et al. |
| 5,725,582 A | 3/1998 | Bevan |
| 5,730,747 A | 3/1998 | Ek et al. |
| 5,733,306 A | 3/1998 | Bonutti |
| 5,735,875 A | 4/1998 | Bonutti et al. |
| 5,735,877 A | 4/1998 | Pagedas |
| 5,735,899 A | 4/1998 | Schwartz et al. |
| 5,741,282 A | 4/1998 | Anspach, III et al. |
| 5,752,952 A | 5/1998 | Adamson |
| 5,752,974 A | 5/1998 | Rhee et al. |
| 5,755,809 A | 5/1998 | Cohen et al. |
| 5,762,458 A | 6/1998 | Wang et al. |
| 5,766,221 A | 6/1998 | Benderev et al. |
| 5,769,894 A | 6/1998 | Ferragamo |
| 5,772,672 A | 6/1998 | Toy et al. |
| 5,776,151 A | 7/1998 | Chan |
| 5,779,706 A * | 7/1998 | Tschakaloff ............ 606/281 |
| 5,782,862 A | 7/1998 | Bonutti |
| 5,785,713 A | 7/1998 | Jobe |
| 5,792,096 A | 8/1998 | Rentmeester et al. |
| 5,797,931 A | 8/1998 | Bito et al. |
| 5,800,537 A | 9/1998 | Bell |
| 5,807,403 A | 9/1998 | Beyar et al. |
| 5,810,849 A | 9/1998 | Kontos et al. |
| 5,810,853 A | 9/1998 | Yoon |
| 5,810,884 A | 9/1998 | Kim |
| 5,814,072 A | 9/1998 | Bonutti |
| 5,814,073 A | 9/1998 | Bonutti |
| 5,817,107 A | 10/1998 | Schaller |
| 5,823,994 A | 10/1998 | Sharkey et al. |
| 5,824,009 A | 10/1998 | Fukuda et al. |
| 5,830,125 A | 11/1998 | Scribner et al. |
| 5,836,897 A | 11/1998 | Sakural et al. |
| 5,839,899 A | 11/1998 | Robinson |
| 5,843,178 A | 12/1998 | Vanney et al. |
| 5,845,645 A | 12/1998 | Bonutti |
| 5,851,185 A | 12/1998 | Berns |
| 5,865,834 A | 2/1999 | McGuire |
| 5,866,634 A | 2/1999 | Tokushige et al. |
| 5,868,749 A | 2/1999 | Reed |
| 5,874,235 A | 2/1999 | Chan |
| 5,879,372 A | 3/1999 | Bartlett |
| 5,891,166 A | 4/1999 | Schervinsky |
| 5,891,168 A | 4/1999 | Thal |
| 5,893,880 A | 4/1999 | Egan et al. |
| 5,897,574 A | 4/1999 | Bonutti |
| 5,899,911 A | 5/1999 | Carter |
| 5,899,921 A | 5/1999 | Caspari et al. |
| 5,906,579 A | 5/1999 | Vander Salm et al. |
| 5,906,625 A | 5/1999 | Bito et al. |
| 5,908,429 A | 6/1999 | Yoon |
| 5,911,721 A | 6/1999 | Nicholson et al. |
| 5,918,604 A | 7/1999 | Whelan |
| 5,919,193 A | 7/1999 | Slavitt |
| 5,919,194 A | 7/1999 | Anderson |
| 5,919,208 A | 7/1999 | Valenti |
| 5,919,215 A | 7/1999 | Wiklund et al. |
| 5,921,986 A | 7/1999 | Bonutti |
| 5,925,064 A | 7/1999 | Meyers et al. |
| 5,928,244 A | 7/1999 | Tovey et al. |
| 5,928,267 A | 7/1999 | Bonutti et al. |
| 5,931,838 A | 8/1999 | Vito |
| 5,931,869 A | 8/1999 | Boucher et al. |
| 5,940,942 A | 8/1999 | Fong |
| 5,941,900 A | 8/1999 | Bonutti |
| 5,941,901 A | 8/1999 | Egan |
| 5,947,982 A | 9/1999 | Duran |
| 5,948,000 A | 9/1999 | Larsen et al. |
| 5,948,001 A | 9/1999 | Larsen |
| 5,948,002 A | 9/1999 | Bonutti |
| 5,951,590 A | 9/1999 | Goldfarb |
| 5,957,953 A | 9/1999 | DiPoto et al. |
| 5,961,499 A | 10/1999 | Bonutti |
| 5,961,521 A | 10/1999 | Roger |
| 5,961,554 A | 10/1999 | Janson et al. |
| 5,964,765 A | 10/1999 | Fenton, Jr. et al. |
| 5,964,769 A | 10/1999 | Wagner et al. |
| 5,968,046 A | 10/1999 | Castleman |
| 5,968,047 A | 10/1999 | Reed |
| 5,980,520 A | 11/1999 | Vancaillie |
| 5,980,559 A | 11/1999 | Bonutti |
| 5,984,929 A | 11/1999 | Bashiri et al. |
| 5,989,282 A | 11/1999 | Bonutti |
| 5,993,458 A | 11/1999 | Vaitekunas et al. |
| 5,993,477 A | 11/1999 | Vaitekunas et al. |
| 6,007,567 A | 12/1999 | Bonutti |
| 6,007,580 A | 12/1999 | Lehto et al. |
| 6,010,525 A | 1/2000 | Bonutti |
| 6,010,526 A | 1/2000 | Sandstrom et al. |
| 6,017,321 A | 1/2000 | Boone |
| 6,033,429 A | 3/2000 | Magovern |
| 6,033,430 A | 3/2000 | Bonutti |
| 6,045,551 A | 4/2000 | Bonutti |
| 6,050,998 A | 4/2000 | Fletcher et al. |
| 6,056,751 A | 5/2000 | Fenton, Jr. |
| 6,056,772 A | 5/2000 | Bonutti |
| 6,056,773 A | 5/2000 | Bonutti |
| 6,059,797 A | 5/2000 | Mears |
| 6,059,817 A | 5/2000 | Bonutti et al. |
| 6,059,827 A | 5/2000 | Fenton |
| 6,063,095 A | 5/2000 | Wang et al. |
| 6,066,151 A | 5/2000 | Miyawaki et al. |
| 6,066,160 A | 5/2000 | Colvin et al. |
| 6,066,166 A | 5/2000 | Bischoff et al. |
| 6,068,637 A | 5/2000 | Popov et al. |
| 6,077,277 A | 6/2000 | Mollenauer et al. |
| 6,077,292 A | 6/2000 | Bonutti |
| 6,080,161 A * | 6/2000 | Eaves et al. ............ 606/76 |
| 6,083,522 A | 7/2000 | Chu et al. |
| 6,086,593 A | 7/2000 | Bonutti |
| 6,086,608 A | 7/2000 | Ek et al. |
| 6,090,072 A | 7/2000 | Kratoska et al. |
| 6,099,531 A | 8/2000 | Bonutti |
| 6,099,537 A | 8/2000 | Sugai et al. |
| 6,099,550 A | 8/2000 | Yoon |
| 6,099,552 A | 8/2000 | Adams |
| 6,102,850 A | 8/2000 | Wang et al. |
| 6,106,545 A | 8/2000 | Egan |
| 6,117,160 A | 9/2000 | Bonutti |
| 6,120,536 A | 9/2000 | Ding et al. |
| 6,125,574 A | 10/2000 | Ganaja et al. |
| 6,126,677 A | 10/2000 | Ganaja et al. |
| 6,139,320 A | 10/2000 | Hahn |
| RE36,974 E | 11/2000 | Bonutti |

(56) References Cited

U.S. PATENT DOCUMENTS

| | | |
|---|---|---|
| 6,149,669 A | 11/2000 | Li |
| 6,152,949 A | 11/2000 | Bonutti |
| 6,155,756 A | 12/2000 | Mericle et al. |
| 6,159,224 A | 12/2000 | Yoon |
| 6,159,234 A | 12/2000 | Bonutti et al. |
| 6,171,307 B1 | 1/2001 | Orlich |
| 6,174,324 B1 | 1/2001 | Egan et al. |
| 6,179,840 B1 | 1/2001 | Bowman |
| 6,179,850 B1 | 1/2001 | Goradia |
| 6,187,008 B1 | 2/2001 | Hamman |
| 6,190,400 B1 | 2/2001 | Van De Moer et al. |
| 6,190,401 B1 | 2/2001 | Green |
| 6,200,322 B1 | 3/2001 | Branch et al. |
| 6,217,591 B1 | 4/2001 | Egan et al. |
| 6,224,593 B1 | 5/2001 | Ryan |
| 6,224,630 B1 | 5/2001 | Bao et al. |
| 6,228,086 B1 | 5/2001 | Wahl et al. |
| 6,231,592 B1 | 5/2001 | Bonutti et al. |
| 6,238,395 B1 | 5/2001 | Bonutti |
| 6,258,091 B1 | 7/2001 | Sevrain et al. |
| 6,264,675 B1 | 7/2001 | Brotz |
| 6,267,761 B1 | 7/2001 | Ryan |
| 6,273,717 B1 | 8/2001 | Hahn et al. |
| 6,280,474 B1 | 8/2001 | Cassidy et al. |
| 6,286,746 B1 | 9/2001 | Egan et al. |
| 6,287,325 B1 | 9/2001 | Bonutti |
| 6,293,961 B2 | 9/2001 | Schwartz et al. |
| 6,306,159 B1 | 10/2001 | Schwartz et al. |
| 6,309,405 B1 | 10/2001 | Bonutti |
| 6,312,448 B1 | 11/2001 | Bonutti |
| 6,338,730 B1 | 1/2002 | Bonutti |
| 6,340,365 B2 | 1/2002 | Dittrich et al. |
| 6,348,056 B1 | 2/2002 | Bates et al. |
| 6,358,271 B1 | 3/2002 | Egan et al. |
| 6,364,897 B1 | 4/2002 | Bonutti |
| 6,368,325 B1 | 4/2002 | McKinley et al. |
| 6,368,343 B1 | 4/2002 | Bonutti |
| 6,371,957 B1 | 4/2002 | Amrein et al. |
| 6,409,742 B1 | 6/2002 | Fulton, III |
| 6,409,743 B1 | 6/2002 | Fenton, Jr. |
| 6,419,704 B1 | 7/2002 | Ferree |
| 6,423,088 B1 | 7/2002 | Fenton |
| 6,425,919 B1 | 7/2002 | Lambrecht |
| 6,428,562 B2 | 8/2002 | Bonutti |
| 6,432,115 B1 | 8/2002 | Mollenauer et al. |
| 6,447,516 B1 | 9/2002 | Bonutti |
| 6,450,985 B1 | 9/2002 | Schoelling et al. |
| 6,461,360 B1 | 10/2002 | Adams |
| 6,468,293 B2 | 10/2002 | Bonutti |
| 6,475,230 B1 | 11/2002 | Bonutti |
| 6,488,196 B1 | 12/2002 | Fenton |
| 6,500,195 B2 | 12/2002 | Bonutti |
| 6,503,259 B2 | 1/2003 | Huxel et al. |
| 6,527,774 B2 | 3/2003 | Lieberman |
| 6,530,933 B1 | 3/2003 | Yeung et al. |
| 6,535,764 B2 | 3/2003 | Imran et al. |
| 6,544,267 B1 | 4/2003 | Cole et al. |
| 6,545,390 B1 | 4/2003 | Hahn et al. |
| 6,547,792 B1 | 4/2003 | Tsuji et al. |
| 6,551,304 B1 | 4/2003 | Whalen et al. |
| 6,554,852 B1 | 4/2003 | Oberlander |
| 6,557,426 B2 | 5/2003 | Reinemann et al. |
| 6,558,390 B2 | 5/2003 | Cragg |
| 6,568,313 B2 | 5/2003 | Fukui et al. |
| 6,569,187 B1 | 5/2003 | Bonutti |
| 6,572,635 B1 | 6/2003 | Bonutti |
| D477,776 S | 7/2003 | Pontaoe |
| 6,585,750 B2 | 7/2003 | Bonutti |
| 6,585,764 B2 | 7/2003 | Wright et al. |
| 6,592,609 B1 | 7/2003 | Bonutti |
| 6,594,517 B1 | 7/2003 | Nevo |
| 6,605,090 B1 * | 8/2003 | Trieu et al. ............... 606/281 |
| 6,610,080 B2 | 8/2003 | Morgan |
| 6,618,910 B1 | 9/2003 | Pontaoe |
| 6,623,486 B1 | 9/2003 | Weaver |
| 6,623,487 B1 * | 9/2003 | Goshert ............... 606/329 |
| 6,626,944 B1 | 9/2003 | Taylor |
| 6,632,245 B2 | 10/2003 | Kim |
| 6,635,073 B2 | 10/2003 | Bonutti |
| 6,638,279 B2 | 10/2003 | Bonutti |
| 6,641,592 B1 | 11/2003 | Sauer et al. |
| 6,645,227 B2 | 11/2003 | Fallin et al. |
| 6,666,877 B2 | 12/2003 | Morgan et al. |
| 6,669,705 B2 | 12/2003 | Westhaver et al. |
| 6,679,888 B2 | 1/2004 | Green et al. |
| 6,685,750 B1 | 2/2004 | Plos et al. |
| 6,699,240 B2 | 3/2004 | Francischelli |
| 6,702,821 B2 | 3/2004 | Bonutti |
| 6,705,179 B1 | 3/2004 | Mohtasham |
| 6,709,457 B1 | 3/2004 | Otte |
| 6,719,765 B2 | 4/2004 | Bonutti |
| 6,719,797 B1 | 4/2004 | Ferree |
| 6,722,552 B2 | 4/2004 | Fenton |
| 6,733,531 B1 | 5/2004 | Trieu |
| 6,764,514 B1 | 7/2004 | Li et al. |
| 6,770,078 B2 | 8/2004 | Bonutti |
| 6,780,198 B1 | 8/2004 | Gregoire et al. |
| 6,786,989 B2 | 9/2004 | Torriani et al. |
| 6,796,003 B1 | 9/2004 | Marvel |
| 6,818,010 B2 | 11/2004 | Eichhorn et al. |
| 6,823,871 B2 | 11/2004 | Schmieding |
| 6,860,885 B2 | 3/2005 | Bonutti |
| 6,878,167 B2 | 4/2005 | Ferree |
| 6,890,334 B2 | 5/2005 | Brace et al. |
| 6,893,434 B2 | 5/2005 | Fenton et al. |
| 6,899,722 B2 | 5/2005 | Bonutti |
| 6,913,666 B1 | 7/2005 | Aeschlimann et al. |
| 6,916,321 B2 | 7/2005 | TenHuisen |
| 6,921,264 B2 | 7/2005 | Mayer et al. |
| 6,923,824 B2 | 8/2005 | Morgan et al. |
| 6,932,835 B2 | 8/2005 | Bonutti |
| 6,942,684 B2 | 9/2005 | Bonutti |
| 6,944,111 B2 | 9/2005 | Nakamura et al. |
| 6,955,540 B2 | 10/2005 | Mayer et al. |
| 6,955,683 B2 | 10/2005 | Bonutti |
| 6,958,077 B2 | 10/2005 | Suddaby |
| 6,981,983 B1 | 1/2006 | Rosenblatt |
| 6,997,940 B2 | 2/2006 | Bonutti |
| 7,001,411 B1 | 2/2006 | Dean |
| 7,004,959 B2 | 2/2006 | Bonutti |
| 7,008,226 B2 | 3/2006 | Mayer et al. |
| 7,018,380 B2 | 3/2006 | Cole |
| 7,033,379 B2 | 4/2006 | Peterson |
| 7,048,755 B2 | 5/2006 | Bonutti |
| 7,066,960 B1 | 6/2006 | Dickman |
| 7,087,073 B2 | 8/2006 | Bonutti |
| 7,090,111 B2 | 8/2006 | Egan et al. |
| 7,094,251 B2 | 8/2006 | Bonutti |
| 7,104,996 B2 | 9/2006 | Bonutti |
| 7,128,763 B1 | 10/2006 | Blatt |
| 7,147,652 B2 | 12/2006 | Bonutti et al. |
| 7,160,405 B2 | 1/2007 | Aeschlimann et al. |
| 7,179,259 B1 * | 2/2007 | Gibbs ............... 606/64 |
| 7,192,448 B2 | 3/2007 | Ferree |
| 7,217,279 B2 | 5/2007 | Reese |
| 7,217,290 B2 | 5/2007 | Bonutti |
| 7,241,297 B2 | 7/2007 | Shaolian et al. |
| 7,250,051 B2 | 7/2007 | Francischelli |
| 7,252,685 B2 | 8/2007 | Bindseil et al. |
| 7,273,497 B2 | 9/2007 | Ferree |
| 7,329,263 B2 | 2/2008 | Bonutti |
| 7,335,205 B2 * | 2/2008 | Aeschlimann et al. ...... 606/232 |
| 7,429,266 B2 | 9/2008 | Bonutti |
| 7,445,634 B2 | 11/2008 | Trieu |
| 7,481,825 B2 | 1/2009 | Bonutti |
| 7,481,831 B2 | 1/2009 | Bonutti |
| 7,510,895 B2 * | 3/2009 | Raterman ............... 438/54 |
| 7,854,750 B2 | 12/2010 | Bonutti |
| 7,879,072 B2 | 2/2011 | Bonutti |
| 7,891,691 B2 | 2/2011 | Bearey |
| 7,967,820 B2 | 6/2011 | Bonutti |
| 8,128,669 B2 | 3/2012 | Bonutti |
| 8,140,982 B2 | 3/2012 | Hamilton, II et al. |
| 8,147,514 B2 | 4/2012 | Bonutti |

(56) References Cited

U.S. PATENT DOCUMENTS

| | | |
|---|---|---|
| 8,162,977 B2 | 4/2012 | Bonutti et al. |
| 2001/0002440 A1 | 5/2001 | Bonutti |
| 2001/0009250 A1 | 7/2001 | Herman et al. |
| 2001/0041916 A1 | 11/2001 | Bonutti |
| 2002/0016593 A1 | 2/2002 | Hearn et al. |
| 2002/0016633 A1 | 2/2002 | Lin et al. |
| 2002/0019649 A1 | 2/2002 | Sikora |
| 2002/0026244 A1 | 2/2002 | Trieu |
| 2002/0029083 A1 | 3/2002 | Zucherman et al. |
| 2002/0029084 A1 | 3/2002 | Paul et al. |
| 2002/0045902 A1 | 4/2002 | Bonutti |
| 2002/0062153 A1 | 5/2002 | Paul et al. |
| 2002/0103495 A1 | 8/2002 | Cole |
| 2002/0123750 A1 | 9/2002 | Eisermann et al. |
| 2002/0183762 A1 | 12/2002 | Anderson et al. |
| 2002/0188301 A1 | 12/2002 | Dallara et al. |
| 2003/0039196 A1 | 2/2003 | Nakamura et al. |
| 2003/0040758 A1 | 2/2003 | Wang et al. |
| 2003/0065361 A1 | 4/2003 | Dreyfuss |
| 2003/0105474 A1 | 6/2003 | Bonutti |
| 2003/0118518 A1 | 6/2003 | Hahn et al. |
| 2003/0158582 A1 | 8/2003 | Bonutti et al. |
| 2003/0167072 A1 | 9/2003 | Oberlander |
| 2003/0181800 A1 | 9/2003 | Bonutti |
| 2003/0195530 A1 | 10/2003 | Thill |
| 2003/0195565 A1 | 10/2003 | Bonutti |
| 2003/0204204 A1 | 10/2003 | Bonutti |
| 2003/0216742 A1 | 11/2003 | Wetzler et al. |
| 2003/0225438 A1 | 12/2003 | Bonutti et al. |
| 2003/0229361 A1 | 12/2003 | Jackson |
| 2004/0010287 A1 | 1/2004 | Bonutti |
| 2004/0030341 A1* | 2/2004 | Aeschlimann et al. ........ 606/72 |
| 2004/0034357 A1 | 2/2004 | Beane et al. |
| 2004/0097939 A1 | 5/2004 | Bonutti |
| 2004/0098050 A1 | 5/2004 | Foerster et al. |
| 2004/0138703 A1 | 7/2004 | Alleyne |
| 2004/0143334 A1 | 7/2004 | Ferree |
| 2004/0167548 A1 | 8/2004 | Bonutti |
| 2004/0220616 A1 | 11/2004 | Bonutti |
| 2004/0225325 A1 | 11/2004 | Bonutti |
| 2004/0230223 A1 | 11/2004 | Bonutti |
| 2004/0236374 A1 | 11/2004 | Bonutti et al. |
| 2005/0033366 A1 | 2/2005 | Cole |
| 2005/0038514 A1 | 2/2005 | Helm et al. |
| 2005/0043796 A1 | 2/2005 | Grant et al. |
| 2005/0071012 A1 | 3/2005 | Serhan et al. |
| 2005/0090827 A1 | 4/2005 | Gedebou |
| 2005/0096699 A1 | 5/2005 | Wixey et al. |
| 2005/0113928 A1 | 5/2005 | Cragg et al. |
| 2005/0126680 A1 | 6/2005 | Aeschlimann et al. |
| 2005/0143826 A1 | 6/2005 | Zucherman et al. |
| 2005/0149024 A1 | 7/2005 | Ferrante et al. |
| 2005/0149029 A1 | 7/2005 | Bonutti |
| 2005/0203521 A1 | 9/2005 | Bonutti |
| 2005/0216059 A1 | 9/2005 | Bonutti |
| 2005/0216087 A1 | 9/2005 | Zucherman et al. |
| 2005/0222620 A1 | 10/2005 | Bonutti |
| 2005/0240190 A1 | 10/2005 | Gall et al. |
| 2005/0240227 A1 | 10/2005 | Bonutti |
| 2005/0246021 A1 | 11/2005 | Ringeisen et al. |
| 2005/0261684 A1 | 11/2005 | Shaolian et al. |
| 2005/0267481 A1 | 12/2005 | Carl et al. |
| 2005/0267534 A1 | 12/2005 | Bonutti |
| 2006/0009855 A1 | 1/2006 | Goble et al. |
| 2006/0015101 A1 | 1/2006 | Warburton et al. |
| 2006/0015108 A1 | 1/2006 | Bonutti |
| 2006/0024357 A1 | 2/2006 | Carpenter et al. |
| 2006/0026244 A1 | 2/2006 | Watson |
| 2006/0064095 A1 | 3/2006 | Senn et al. |
| 2006/0089646 A1 | 4/2006 | Bonutti |
| 2006/0122600 A1 | 6/2006 | Cole |
| 2006/0122704 A1 | 6/2006 | Vresilovic et al. |
| 2006/0142799 A1 | 6/2006 | Bonutti |
| 2006/0167495 A1 | 7/2006 | Bonutti et al. |
| 2006/0200199 A1 | 9/2006 | Bonutti |
| 2006/0212073 A1 | 9/2006 | Bonutti |
| 2006/0217765 A1 | 9/2006 | Bonutti |
| 2006/0229623 A1 | 10/2006 | Bonutti et al. |
| 2006/0235470 A1 | 10/2006 | Bonutti et al. |
| 2006/0241695 A1 | 10/2006 | Bonutti et al. |
| 2006/0264950 A1* | 11/2006 | Nelson et al. ................ 606/72 |
| 2006/0265009 A1 | 11/2006 | Bonutti |
| 2006/0265011 A1 | 11/2006 | Bonutti |
| 2007/0032825 A1 | 2/2007 | Bonutti et al. |
| 2007/0088362 A1 | 4/2007 | Bonutti et al. |
| 2007/0118129 A1* | 5/2007 | Fraser et al. .................. 606/71 |
| 2007/0123878 A1* | 5/2007 | Shaver et al. ................. 606/64 |
| 2007/0198555 A1 | 8/2007 | Friedman et al. |
| 2007/0265561 A1 | 11/2007 | Yeung |
| 2007/0270833 A1 | 11/2007 | Bonutti |
| 2008/0021474 A1 | 1/2008 | Bonutti et al. |
| 2008/0039845 A1 | 2/2008 | Bonutti et al. |
| 2008/0039873 A1 | 2/2008 | Bonutti |
| 2008/0046090 A1 | 2/2008 | Paul et al. |
| 2008/0097448 A1 | 4/2008 | Binder et al. |
| 2008/0108897 A1 | 5/2008 | Bonutti et al. |
| 2008/0108916 A1 | 5/2008 | Bonutti |
| 2008/0114399 A1 | 5/2008 | Bonutti |
| 2008/0132950 A1* | 6/2008 | Lange .......................... 606/246 |
| 2008/0140116 A1 | 6/2008 | Bonutti |
| 2008/0140117 A1 | 6/2008 | Bonutti |
| 2008/0195145 A1 | 8/2008 | Bonutti et al. |
| 2008/0269753 A1* | 10/2008 | Cannestra ..................... 606/70 |
| 2008/0269808 A1* | 10/2008 | Gall et al. .................... 606/299 |
| 2009/0024161 A1 | 1/2009 | Bonutti |
| 2009/0093684 A1 | 4/2009 | Schorer |
| 2009/0138014 A1 | 5/2009 | Bonutti |
| 2009/0194969 A1 | 8/2009 | Bearey |
| 2010/0211120 A1 | 8/2010 | Bonutti et al. |
| 2011/0060375 A1 | 3/2011 | Bonutti |
| 2011/0295253 A1 | 12/2011 | Bonutti et al. |
| 2012/0165841 A1 | 6/2012 | Bonutti |
| 2012/0191140 A1 | 7/2012 | Bonutti |
| 2012/0197316 A1 | 8/2012 | Mayer et al. |
| 2012/0215233 A1 | 8/2012 | Bonutti et al. |

FOREIGN PATENT DOCUMENTS

| | | |
|---|---|---|
| CA | 2698057 | 3/2009 |
| DE | 1903016 | 10/1964 |
| DE | 1903316 | 10/1964 |
| DE | 1903016 | 8/1970 |
| DE | 3517204 | 11/1986 |
| DE | 3722538 | 1/1989 |
| DE | 9002844 U1 | 1/1991 |
| EP | 784454 | 5/1996 |
| EP | 773004 | 5/1997 |
| EP | 1614525 | 1/2006 |
| EP | 1988837 | 8/2007 |
| EP | 2134294 | 12/2009 |
| FR | 2717368 | 3/1994 |
| FR | 2696338 | 4/1994 |
| FR | 2728779 | 1/1995 |
| FR | 2736257 | 7/1995 |
| FR | 2750031 | 6/1996 |
| FR | 2771621 | 11/1997 |
| FR | 2785171 | 10/1998 |
| GB | 2093701 A | 9/1982 |
| GB | 2306110 A | 4/1997 |
| JP | 8140982 | 6/1996 |
| SU | 184396 | 7/1966 |
| WO | 91/12779 | 9/1991 |
| WO | 93/23094 | 11/1993 |
| WO | WO9408642 | 4/1994 |
| WO | 95/16398 | 6/1995 |
| WO | WO 95/31941 | 11/1995 |
| WO | WO9614802 | 5/1996 |
| WO | WO9712779 | 4/1997 |
| WO | 97/49347 | 12/1997 |
| WO | WO 97/49347 | 12/1997 |
| WO | WO9811838 | 3/1998 |
| WO | WO9826720 | 6/1998 |
| WO | WO02053011 | 7/2002 |
| WO | 2007/092869 | 8/2007 |

(56) References Cited

FOREIGN PATENT DOCUMENTS

| WO | 2007/092869 A2 | 8/2007 |
|---|---|---|
| WO | 2008/116203 | 9/2008 |
| WO | 2009/029908 | 3/2009 |
| WO | WO2010099222 | 2/2010 |

OTHER PUBLICATIONS

Copending U.S. Appl. No. 11/461,110, Response to Office Action Mar. 12, 2008.
Copending U.S. Appl. No. 11/461,110, Non-Final Rejection mailed Jun. 6, 2008.
Copending U.S. Appl. No. 11/461,110, Response to Office Action Oct. 6, 2008.
Copending U.S. Appl. No. 11/461,110, Non-Final Rejection mailed Apr. 22, 2009.
Copending U.S. Appl. No. 11/461,110, Response to Office Action Sep. 22, 2009.
Copending U.S. Appl. No. 11/461,110, Final Rejection mailed Dec. 8, 2009.
Copending U.S. Appl. No. 11/930,621.
Copending U.S. Appl. No. 11/930,621, Non-Final Rejection mailed Sep. 21, 2009.
Copending U.S. Appl. No. 11/930,621, Response to Office Action Mar. 22, 2010.
Copending U.S. Appl. No. 09/524,397.
Copending U.S. Appl. No. 09/524,397, Non-Final Rejection mailed Dec. 18, 2000.
Copending U.S. Appl. No. 09/524,397, Response to Office Action Mar. 19, 2001.
Copending U.S. Appl. No. 09/524,397, Final Rejection mailed Jun. 13, 2001.
Copending U.S. Appl. No. 09/524,397, Response to Office Action Oct. 15, 2001.
Copending U.S. Appl. No. 10/076,919.
Copending U.S. Appl. No. 10/458,117.
Copending U.S. Appl. No. 10/458,117, Non-Final Rejection mailed Mar. 22, 2005.
Copending U.S. Appl. No. 10/458,117, Response to Office Action Jun. 22, 2005.
Copending U.S. Appl. No. 10/458,117, Final Rejection mailed Sep. 6, 2005.
Copending U.S. Appl. No. 10/458,117, Response to Office Action Nov. 8, 2005.
Copending U.S. Appl. No. 10/458,117, Advisory Actiom Jan. 20, 2006.
Copending U.S. Appl. No. 10/458,117, Request for Continued Examination Feb. 21, 2006.
Copending U.S. Appl. No. 10/458,117, Non-Final Rejection mailed Nov. 15, 2006.
Copending U.S. Appl. No. 10/458,117, Response to Office Action Feb. 13, 2007.
Copending U.S. Appl. No. 10/458,117, Final Rejection mailed May 3, 2007.
Copending U.S. Appl. No. 10/458,117, Request for Continued Examination Aug. 3, 2007.
Copending U.S. Appl. No. 10/458,117, Response to Office Action Aug. 3, 2007.
Copending U.S. Appl. No. 10/458,117, Request for Conintiued Examination Feb. 26, 2008.
Copending U.S. Appl. No. 10/458,117, Examiner Interview Summary May 16, 2008.
Copending U.S. Appl. No. 11/456,132, filed Jul. 7, 2006.
Copending U.S. Appl. No. 11/456,132, Non-Final Rejection mailed Jun. 18, 2007.
Copending U.S. Appl. No. 11/456,132, Response to Office Action Nov. 19, 2007.
Copending U.S. Appl. No. 11/456,132, Final Rejection mailed Mar. 11, 2008.
Copending U.S. Appl. No. 11/456,132, Request for Continued Examination Jun. 11, 2008.
Copending U.S. Appl. No. 11/456,132, Response to Office Action Jun. 11, 2008.
Copending U.S. Appl. No. 11/456,132, Non-Final Rejection mailed Oct. 7, 2008.
Copending U.S. Appl. No. 11/456,132, Response to Office Action Jan. 7, 2009.
Copending U.S. Appl. No. 11/456,132, Non-Final Rejection mailed Mar. 13, 2009.
Copending U.S. Appl. No. 11/456,132, Response to Office Action Aug. 13, 2009.
Copending U.S. Appl. No. 11/456,132, Examiner Interview Summary mailed Aug. 28, 2009.
Copending U.S. Appl. No. 11/456,132, Final Rejection mailed Dec. 18, 2009.
Copending U.S. Appl. No. 11/456,132, Response to Office Action Apr. 19, 2010.
Copending U.S. Appl. No. 11/456,221, filed Jul. 10, 2006.
Copending U.S. Appl. No. 11/456,221, Non-Final Rejection mailed Jul. 9, 2007.
Copending U.S. Appl. No. 11/456,221, Response to Office Action Nov. 9, 2007.
Copending U.S. Appl. No. 11/456,221, Final Rejection mailed Feb. 22, 2008.
Copending U.S. Appl. No. 11/456,221, Response to Office Action May 22, 2008.
Copending U.S. Appl. No. 11/456,221, Request for Continued Examintation Jun. 19, 2008.
Copending U.S. Appl. No. 11/456,221, Non-Final Rejection mailed Oct. 29, 2008.
Copending U.S. Appl. No. 11/456,221, Response to Office Action Mar. 30, 2009.
Copending U.S. Appl. No. 11/456,221, Non-Final Rejection mailed Jul. 6, 2009.
Copending U.S. Appl. No. 11/456,221, Response to Office Action Jan. 6, 2010.
Copending U.S. Appl. No. 11/456,221, Final Rejection mailed Mar. 24, 2010.
Copending U.S. Appl. No. 11/932,051, filed Oct. 31, 2007.
Copending U.S. Appl. No. 11/932,051, Requirement for Restriction Jan. 22, 2010.
Copending U.S. Appl. No. 10/228,855, filed Aug. 27, 2002.
Copending U.S. Appl. No. 10/228,855, Non-Final Rejection mailed Sep. 28, 2005.
Copending U.S. Appl. No. 10/228,855, Response to Office Action Dec. 28, 2005.
Copending U.S. Appl. No. 11/465,199, filed Aug. 17, 2006.
Copending U.S. Appl. No. 11/465,199, Non-Final Rejecrion mailed Dec. 28, 2009.
Copending U.S. Appl. No. 11/932,602, filed Oct. 31, 2007.
Copending U.S. Appl. No. 10/780,444, filed Feb. 17, 2004.
Copending U.S. Appl. No. 10/780,444, Requirement for Restriction Apr. 10, 2007.
Copending U.S. Appl. No. 10/780,444, Response to Office Action May 10, 2007.
Copending U.S. Appl. No. 10/780,444, Requirement for Restriction Sep. 12, 2007.
Copending U.S. Appl. No. 10/780,444, Response to Office Action Oct. 12, 2007.
Copending U.S. Appl. No. 10/780,444, Non-Final Rejection mailed Mar. 11, 2008.
Copending U.S. Appl. No. 10/780,444, Response to Office Action Jul. 9, 2008.
Copending U.S. Appl. No. 10/780,444, Final Rejection mailed Dec. 23, 2008.
Copending U.S. Appl. No. 10/780,444, Response to Office Action Apr. 23, 2009.
Copending U.S. Appl. No. 10/780,444, Request for Continued Examination Apr. 23, 2009.
Copending U.S. Appl. No. 10/780,444, Non-Final Rejection mailed Jul. 7, 2009.

(56) References Cited

OTHER PUBLICATIONS

Copending U.S. Appl. No. 10/780,444, Examiner Interview Summary mailed Nov. 20, 2009.
Copending U.S. Appl. No. 10/780,444, Response to Office Action Dec. 4, 2009.
Copending U.S. Appl. No. 10/780,444, Final Rejection mailed Mar. 30, 2010.
Copending U.S. Appl. No. 10/779,978, filed Feb. 17, 2004.
Copending U.S. Appl. No. 10/779,978, Requirement for Restriction Apr. 20, 2007.
Copending U.S. Appl. No. 10/779,978, Response to Office Action May 21, 2007.
Copending U.S. Appl. No. 10/779,978, Non-Final Rejection mailed Aug. 3, 2007.
IPR—International Publication WO/2009/029908, published May 3, 2009 for PCT/US08/029908.
ISR—International Search Report, WO /2009/029908, published May 3, 2009 for PCT/US08/029908.
IPER—Internation Preliminary Report on Patentability, WO/2009/029908, published Mar. 2, 2010 for PCT/US08/029908.
Written Opinion WO/2009/029908 dated Feb. 28, 2010 for PCT/US08/029908.
Canadian Patent Application #2641580 equivalent to U.S. Appl. No. 11/671,556, P. Bonutti, Aug. 6, 2008.
Canadian Patent Application #2680827 equivalent to U.S. Appl. No. 11/689,670, P. Bonutti, Sep. 22, 2009.
Canadian Patent Application #2698057 equivalent to U.S. Appl. No. 12/202,210, P. Bonutti, Aug. 26, 2010.
European Patent Application #08828652 equivalent to U.S. Appl. No. 12/202,210, P. Bonutti, Aug. 29, 2008.
ISR—International Search Report PCT/US2010/025263 completed Apr. 13, 2010.
Copending U.S. Appl. No. 11/461,110, Request for Continued Examination Jun. 8, 2010.
Copending U.S. Appl. No. 11/461,110, Response to Office Action Jun. 8, 2010.
Copending U.S. Appl. No. 11/930,621, Final Rejection Jun. 22, 2010.
Copending U.S. Appl. No. 11/465,199, Response to Office Action Jun. 28, 2010.
Copending U.S. Appl. No. 10/779,978, Response to Office Action Dec. 3, 2007.
Copending U.S. Appl. No. 10/779,978, Response to Office Action Mar. 25, 2008.
Copending U.S. Appl. No. 10/779,978, Non-Final Rejection mailed Jun. 18, 2008.
Copending U.S. Appl. No. 10/779,978, Response to Office Action Oct. 20, 2008.
Copending U.S. Appl. No. 10/779,978, Final Rejection mailed Feb. 3, 2009.
Copending U.S. Appl. No. 10/779,978, Request for Continued Examination Jul. 6, 2009.
Copending U.S. Appl. No. 10/779,978, Response to Office Action Jul. 6, 2009.
Copending U.S. Appl. No. 10/779,978, Non-Final Rejection mailed Oct. 1, 2009.
Copending U.S. Appl. No. 10/779,978, Response to Office Action Feb. 1, 2010.
Copending U.S. Appl. No. 10/779,978, Final Rejection mailed May 14, 2010.
Copending U.S. Appl. No. 10/797,685, filed Mar. 9, 2004.
Copending U.S. Appl. No. 10/797,685, Non-Final Rejection mailed Nov. 17, 2006.
Copending U.S. Appl. No. 10/797,685, Response to Office Action Feb. 20, 2007.
Copending U.S. Appl. No. 10/797,685, Final Rejection mailed Apr. 25, 2007.
Copending U.S. Appl. No. 10/797,685, Response to Office Action Aug. 27, 2007.
Copending U.S. Appl. No. 10/797,685, Examiner Interview Summary mailed Sep. 11, 2007.
Copending U.S. Appl. No. 11/874,323, filed Oct. 18, 2007.
Copending U.S. Appl. No. 11/671,556, filed Feb. 6, 2007.
Copending U.S. Appl. No. 11/671,556, Requirement for Restriction Sep. 1, 2009.
Copending U.S. Appl. No. 11/671,556, Response to Office Action Nov. 2, 2009.
Copending U.S. Appl. No. 11/671,556, Non-Final Rejection mailed Feb. 22, 2010.
Copending U.S. Appl. No. 11/416,618, filed May 3, 2006.
Copending U.S. Appl. No. 11/416,618, Non-Final Rejection mailed Nov. 26, 2008.
Copending U.S. Appl. No. 11/416,618, Response to Office Action Mar. 26, 2009.
Copending U.S. Appl. No. 11/416,618, Final Rejection mailed Jun. 24, 2009.
Copending U.S. Appl. No. 11/416,618, Response to Office Action Sep. 24, 2009.
Copending U.S. Appl. No. 11/416,618, Non-Final Rejection mailed Oct. 13, 2009.
Copending U.S. Appl. No. 11/416,618, Response to Office Action Mar. 15, 2010.
Copending U.S. Appl. No. 11/416,618, Examiner Interview Summary mailed Apr. 15, 2010.
Copending U.S. Appl. No. 11/416,618, Response to Office Action Apr. 16, 2010.
Copending U.S. Appl. No. 11/689,670, filed Mar. 22, 2007.
Copending U.S. Appl. No. 11/689,670, Requirement for Restriction Mar. 15, 2010.
Copending U.S. Appl. No. 11/689,670, Response to Office Action Apr. 15, 2010.
The Search for the Holy Grail: A Centrury of Anterior Cruciate Ligament Reconstruction, R. John Naranja, American Journal of Orthopedics, Nov. 1997.
Femoral Bone Plug Recession in Endoscope Anterior Cruciate Ligament Reconstruction, David E. Taylor, Arthroscopy: The Journal of Arthroscopic and Related Surgery, Aug. 1996.
Meniscus Replacement with Bone Anchors: A Surgical Technique, Arthroscopy: The Journal of Arcioscopic and Related Surgery, 1994.
Problem Solving Report Question No. 1014984.066, Ultrasonic Welding, (c) 1999.
Guide to Ultrasound Plastic Assembly, Ultrasonic Division Publication, (c) 1995.
Branson, Polymers: Characteristics and Compatibility for Ultrasonic Assembly, Applied Technologies Group, Publication unknown.
Enabling Local Drug Delivery-Implant Device Combination Therapies, Surmodics, Inc., (c) 2003.
Stent Based Delivery of Sirolimus Reduces Neointimal Formation in a Porcine Coronary Model, Takeshi Suzuki, American Heart Association, Inc. (c) 2001.
Why Tie a Knot When You Can Use Y-Knot?, Innovasive Devices Inc., (c) 1998.
Ask Oxford projection, compact oxford english dicitionary: projection, Mar. 30, 2009.
Ask Oxford projection, compact oxford english dicitionary: slit, Mar. 30, 2009.
Textured Surface Technology, Branson Technolog, Branson Ultrasonics Copr., (c) 1992.
IPR—International Publication WO/2007/092869, published Aug. 16, 2007 for PCT/US2007/061730.
ISR—International Search Report WO/2007/092869, published Dec. 13, 2007 for PCT/US2007/061730.
IPER—Internation Preliminary Report on Patentability, WO/2007/092869, published Aug. 12, 2008 for PCT/US2007/061730.
Written Opinion WO/2007/092869 dated Aug. 7, 2008 for PCT/US2007/061730.
Copending U.S. Appl. No. 09/556,458, filed May 3, 2000.
Copending U.S. Appl. No. 09/556,458, Non-Final Rejection mailed Sep. 25, 2002.

(56) References Cited

OTHER PUBLICATIONS

Copending U.S. Appl. No. 09/556,458, Response to Office Action Dec. 26, 2002.
Copending U.S. Appl. No. 10/614,352, filed Jul. 7, 2003.
Copending U.S. Appl. No. 10/614,352, Non-Final Rejection mailed Dec. 1, 2005.
Copending U.S. Appl. No. 10/614,352, Response to Office Action Mar. 1, 2006.
Copending U.S. Appl. No. 10/614,352, Non-Final Rejection mailed Aug. 1, 2006.
Copending U.S. Appl. No. 10/614,352, Response to Office Action Nov. 1, 2006.
Copending U.S. Appl. No. 10/614,352, Final Rejection mailed Jan. 25, 2007.
Copending U.S. Appl. No. 10/614,352, Response to Office Action Mar. 26, 2007.
Copending U.S. Appl. No. 10/614,352, Non-Final Rejection mailed Apr. 17, 2007.
Copending U.S. Appl. No. 10/614,352, Response to Office Action Jul. 17, 2007.
Copending U.S. Appl. No. 10/614,352, Examiner Interview Summary Jul. 31, 2007.
Copending U.S. Appl. No. 10/614,352, Final Rejection mailed Oct. 2, 2007.
Copending U.S. Appl. No. 10/614,352, Request for Continued Examination Oct. 30, 2007.
Copending U.S. Appl. No. 10/614,352, Response to Office Action Oct. 30, 2007.
Copending U.S. Appl. No. 10/614,352, Non-Final Rejection mailed Jan. 15, 2008.
Copending U.S. Appl. No. 10/614,352, Response to Office Action May 15, 2008.
Copending U.S. Appl. No. 10/614,352, Non-Final Rejection mailed Aug. 21, 2008.
Copending U.S. Appl. No. 10/614,352, Response to Office Action Dec. 22, 2008.
Copending U.S. Appl. No. 10/614,352, Final Rejection mailed Apr. 14, 2009.
Copending U.S. Appl. No. 10/614,352, Request for Continued Examination Sep. 14, 2009.
Copending U.S. Appl. No. 10/614,352, Response to Office Action Sep. 14, 2009.
Copending U.S. Appl. No. 10/614,352, Non-Final Rejection mailed Nov. 24, 2009.
Copending U.S. Appl. No. 10/614,352, Response to Office Action Apr. 26, 2010.
Copending U.S. Appl. No. 11/931,823, filed Oct. 31, 2007.
Copending U.S. Appl. No. 09/789,621, filed Feb. 21, 2001.
Copending U.S. Appl. No. 10/413,696, filed Apr. 14, 2003.
Copending U.S. Appl. No. 10/413,696, Requirement for Restriction Jun. 8, 2005.
Copending U.S. Appl. No. 10/413,696, Response to Office Action Jul. 5, 2005.
Copending U.S. Appl. No. 10/413,696, Non-Final Rejection mailed Sep. 23, 2005.
Copending U.S. Appl. No. 10/413,696, Response to Office Action Dec. 20, 2005.
Copending U.S. Appl. No. 11/460,650, filed Jul. 28, 2006.
Copending U.S. Appl. No. 11/460,650, Non-Final Rejection mailed May 30, 2007.
Copending U.S. Appl. No. 11/460,650, Response to Office Action Oct. 1, 2007.
Copending U.S. Appl. No. 11/460,650, Non-Final Rejection mailed Dec. 28, 2007.
Copending U.S. Appl. No. 11/460,650, Response to Office Action Mar. 28, 2008.
Copending U.S. Appl. No. 11/460,650, Final Rejection mailed Aug. 29, 2008.
Copending U.S. Appl. No. 11/460,650, Request for Continued Examination Jan. 29, 2009.
Copending U.S. Appl. No. 11/460,650, Response to Office Action Jan. 29, 2009.
Copending U.S. Appl. No. 11/460,650, Non-Final Rejection mailed Mar. 10, 2009.
Copending U.S. Appl. No. 11/460,650, Response to Office Action Jun. 10, 2009.
Copending U.S. Appl. No. 11/460,650, Non-Final Rejection mailed Sep. 16, 2009.
Copending U.S. Appl. No. 11/460,650, Examiner Interview Summary mailed Dec. 23, 2009.
Copending U.S. Appl. No. 11/460,650, Response to Office Action Jan. 12, 2010.
Copending U.S. Appl. No. 11/460,650, Final Rejection mailed Apr. 20, 2010.
Copending U.S. Appl. No. 11/461,110, filed Jul. 31, 2006.
Copending U.S. Appl. No. 11/461,110, Non-Final Rejection mailed May 14, 2007.
Copending U.S. Appl. No. 11/461,110, Response to Office Action Oct. 15, 2007.
Copending U.S. Appl. No. 11/461,110, Final Rejection mailed Dec. 12, 2007.
IPR—International Publication WO/2008/116203, published Sep. 22, 2009 for PCT/US08/57948.
ISR—International Search Report WO/2008/116203, published Dec. 24, 2008 for PCT/US08/57948.
IPER—Internation Preliminary Report on Patentability, WO/2008/116203, published Sep. 22, 2009 for PCT/US08/57948.
Written Opinion WO/2008/116203 dated Oct. 23, 2008 for PCT/US08/57948.
IPR—International Publication W02009/029908, published May 3, 2009 for PCT/US08/74941.
ISR—International Search Report, WO2009/029908, published May 3, 2009 for PCT/US08/74941.
IPER—Internation Preliminary Report on Patentability, WO2009/029908, published Mar. 2, 2010 for PCT/US08/74941.
Written Opinion WO2009/029908 dated Feb. 28, 2010 for PCT/US08/74941.
International Search Report PCT/US2010/025263 completed Apr. 13, 2010.
Written Opinion for PCT/US2010/025263 completed Apr. 13, 2010.
Arthrex, Protect your graft, Am J Sports Med, vol. 22, No. 4, Jul.-Aug 1994.
Barrett et al, T-Fix endoscopic meniscal repair: technique and approach to different types of tears, Apr. 1995, Arthroscopy vol. 11 No. 2 p. 245-51.
Cope, Suture Anchor for Visceral Drainage, AJR, vol. 148 p. 160-162, Jan. 1986.
Gabriel, Arthroscopic Fixation Devices, Wiley Enc. of Biomed Eng., 2006.
Innovasive, We've got you covered, Am J Sports Med, vol. 26, No. 1, Jan.-Feb. 1998.
510k—TranSet Fracture Fixation System, Feb. 24, 2004, k033717.
510k—Linvatec Biomaterials modification of Duet and impact Suture Anchor, Nov. 19, 2004, k042966.
510k, arthrex pushlock, Jun. 29, 2005, K051219.
510k, mitek micro anchor, Nov. 6, 1996, K962511.
510k, Multitak Suture System, Jan. 10, 1997, K964324.
510k, Modified Mitek 3.5mm Absorbable Suture Anchor System, Jun. 9, 1997, K970896.
510K, Summary for Arthrex Inc.'s Bio-Interference Screw, Sep. 9, 1997, K971358.
510k, Surgicraft Bone Tie, Sep. 25, 1998, K982719.
Karlsson et al, Repair of Bankart lesions with a suture anchor in recurrent dislocation of the shoulder, Scand. j. of Med & Science in Sports, 1995, 5:170-174.
Madjar et al, Minimally Invasive Pervaginam Procedures, for the Treatment of Female Stress Incontinence . . . , Artificial Organs, 22 (10) 879-885, 1998.
Nowak et al, Comparative Study of Fixation Techniques in the Open Bankart Operation Using Either a Cannulated Screw or Suture-Anchors, Acta Orthopcedica Belgica, vol. 64—Feb. 1998.

(56) References Cited

OTHER PUBLICATIONS

Packer et al, Repair of Acute Scapho-Lunate Dissociation Facilitated by the "Tag"* Suture Anchor, Journal of Hand Surgery (British and European Volume, 1994) 19B: 5: 563-564.
Richmond, Modificatio of the Bankart reconstruction with a suture anchor, Am J Sports Med, vol. 19, No. 4, p. 343-346, 1991.
Shea et al, Technical Note: Arthroscopic Rotator Cuff Repair Using a Transhumeral Approach to Fixation, Arthroscopy: The Journal of Arthroscopic and Related Surgery, vol. 14, No. 1 (Jan.-Feb. 1998),: pp. 118-122.
Tfix, Acufex just tied the knot . . . , Am. J. Sports Med., vol. 22, No. 3, May-Jun. 1994.
Wong et al, Case Report: Proper Insertion Angle is Essential to Prevent Intra-Articular Protrusion of a Knotless Suture Anchor in Shoulder Rotator Cuff Repair, Arthroscopy: The Journal of Arthroscopic and Related Surgery, vol. 26, No. 2 (Feb. 2010),: pp. 286-290.
Cobb et al, Late Correction of Malunited Intercondylar Humeral Fractures Intra-Articular Osteotomy and Tricortical Bone Grafting, J BoneJointSurg [Br] 1994; 76-B:622-6.
Fellinger, et al, Radial avulsion of the triangular fibrocartilage complex in acute wrist trauma: a new technique for arthroscopic repair, Jun. 1997, Arthroscopy vol. 13 No. 3 p. 370-4.
Hecker et al , Pull-out strength of suture anchors for rotator cuff and Bankart lesion repairs, Nov.-Dec. 1993 , The American Journal of Sports Medicine, vol. 21 No. 6 p. 874-9.
Hernigou et al , Proximal Tibial Osteotomy for Osteoarthritis with Varus Deformity a Ten to Thirteen-Year Follow-Up Study, J Bone Joint Surg, vol. 69-A, No. 3. Mar. 1987, p. 332-354.
Ibarra et al, Glenoid Replacement in Total Shoulder Arthroplasty, The Orthopedic Clinics of Northamerica: Total Shoulder Arthroplasty, vol. 29 No. 3, Jul. 1998 p. 403-413.
Mosca et al, Calcaneal Lengthening for Valgus Deformity of the Hindfoot: Results in Children Who Had Severe, Symptomatic Flatfoot and Skewfoot, J Bone Joint Surg,, 1195—p. 499-512.
Murphycet al , Radial Opening Wedge Osteotomy in Madelung's Deformity, J. Hand Surg, vol. 21 A No. 6 Nov. 1996, p. 1035-44.
Biomet, Stanmore Modular Hip, J. Bone Joint Surg., vol. 76-B : No. Two, Mar. 1994.
Intl Prelim Rep on Patentability and Written Opinion for PCT/US10/25263 dated Aug. 30, 2011.
European Search Report dated Sep. 10, 2012 for EP08732724.3 (046).
Petition for Inter Partes Review of U.S. Pat. No. 5,980,559, IPR 2013-00603, Filing Date Sep. 24, 2013.
Declaration of David Kaplan, Ph.D. Regarding U.S. Pat. No. 5,980,559, IPR 2013-00603, Sep. 24, 2013.
Petition for Inter Partes Review of U.S. Pat. No. 7,087,073, IPR 2013-00604, Filing Date Sep. 24, 2013.
Declaration of Wayne J. Sebastianelli, MD Regarding U.S. Pat. No. 7,087,073, Sep. 24, 2013, IPR 2013-00604.
Petition for Inter Partes Review of U.S. Pat. No. 6,500,195, IPR 2013-00624, Filing Date Oct. 2, 2013.
Declaration of Dr. Philip Hardy in Support of Petition for Inter Partes Review of U.S. Pat. No. 6,500,195, IPR 2013-00624, Sep. 25, 2013.
Petition for Inter Partes Review of U.S. Pat. No. 5,527,343, IPR 2013-00628, Filing Date Sep. 26, 2013, Sep. 25, 2013.
Declaration of Dr. Philip Hardy in Support of Petition for Inter Partes Review of U.S. Pat. No. 5,527,343, IPR 2013-00628, Sep. 25, 2013.
Corrected Petition for Inter Partes Review of U.S. Pat. No. 5,921,986, IPR 2013-00631, Filing Date Sep. 27, 2013.
Expert Declaration of Steve E. Jordan, MD, For Inter Partes Review of U.S. Pat. No. 5,921,986, IPR 2013-00631, Sep. 24, 2013.
Corrected Petition for Inter Partes Review of U.S. Pat. No. 8,147,514, IPR 2013-00632, Filing Date Sep. 27, 2013.
Declaration of Steve Jordan for U.S. Pat. No. 8,147,514, from IPR 2013-00632, dated Sep. 23, 2013.
Corrected Petition for Inter Partes Review of U.S. Pat. No. 8,147,514, IPR 2013-00633, Filing Date Sep. 27, 2013.
Declaration of Steve Jordan for U.S. Pat. No. 8,147,514, from IPR 2013-00633, dated Sep. 23, 2013.
Flory, Principles of Polymer Chemistry, 1953, selected pages.
Grizzi, Hydrolytic degradation of devices based on poly(DL-lactic acid) size-dependence, Biomaterials, 1995, vol. 16, No. 4, p. 305-11 (IPR 2013-00603, exhibit 1006).
Gopferich, Mechanisms of polymer degradation and erosion, Biomaterials, 1996, vol. 17, No. 2, p. 103-114.
Gao et el, Swelling of Hydroxypropyl Methylcellulose Matrix Tablets . . . , J. of Pharmaceutical Sciences, vol. 85, No. 7, Jul. 1996, p. 732-740.
Linvatec, Impact Suture Anchor brochure, 2004.
Seitz et al, Repair of the Tibiofibular Syndesmosis with a Flexible Implant, J. of Orthopaedic Trauma, vol. 5, No. 1, p. 78-82, 1991.
Translation of FR2696338 with translator's certificate dated Sep. 17, 2013.
Translation of DE9002844.9 with translator's certificate dated Sep. 26, 2013.
Declaration of Steve Jordan for U.S. Pat. No. 5,921,986, from IPR 2013-00632, dated Sep. 24, 2013.
Declaration of Steve Jordan for U.S. Pat. No. 5,921,986, from IPR 2013-00633, dated Sep. 24, 2013.
Declaration of Dr. Steve E. Jordan for U.S. Pat. No. 8,147,514, from IPR 2013-00631, dated Sep. 23, 2013.
Copending U.S. Appl. No. 11/932,907—RCE Response Sep. 15, 2011.
Copending U.S. Appl. No. 11/258,795 Non-Final Office Action mailed Apr. 26, 2011.
Copending U.S. Appl. No. 11/689,670, RCE Response Sep. 19, 2011.
Copending U.S. Appl. No. 10/614,352, Final Office Action Jul. 12, 2010.
Copending U.S. Appl. No. 11/932,602 Final Response to Office Action Jun. 10, 2011.
Copending U.S. Appl. No. 11/671,556 Response filed Aug. 23, 2010.
Co-pending Appl. No. 11/438,537, Supplemental Final Rejection mailed Sep. 25, 2009.
Non-Final Office Action dated Jun. 25, 2015 relating to U.S. Appl. No. 11/671,556, 11 pages.
Final Office Action dated Aug. 7, 2015 relating to U.S. Appl. No. 13/953,652, 9 pgs.

* cited by examiner

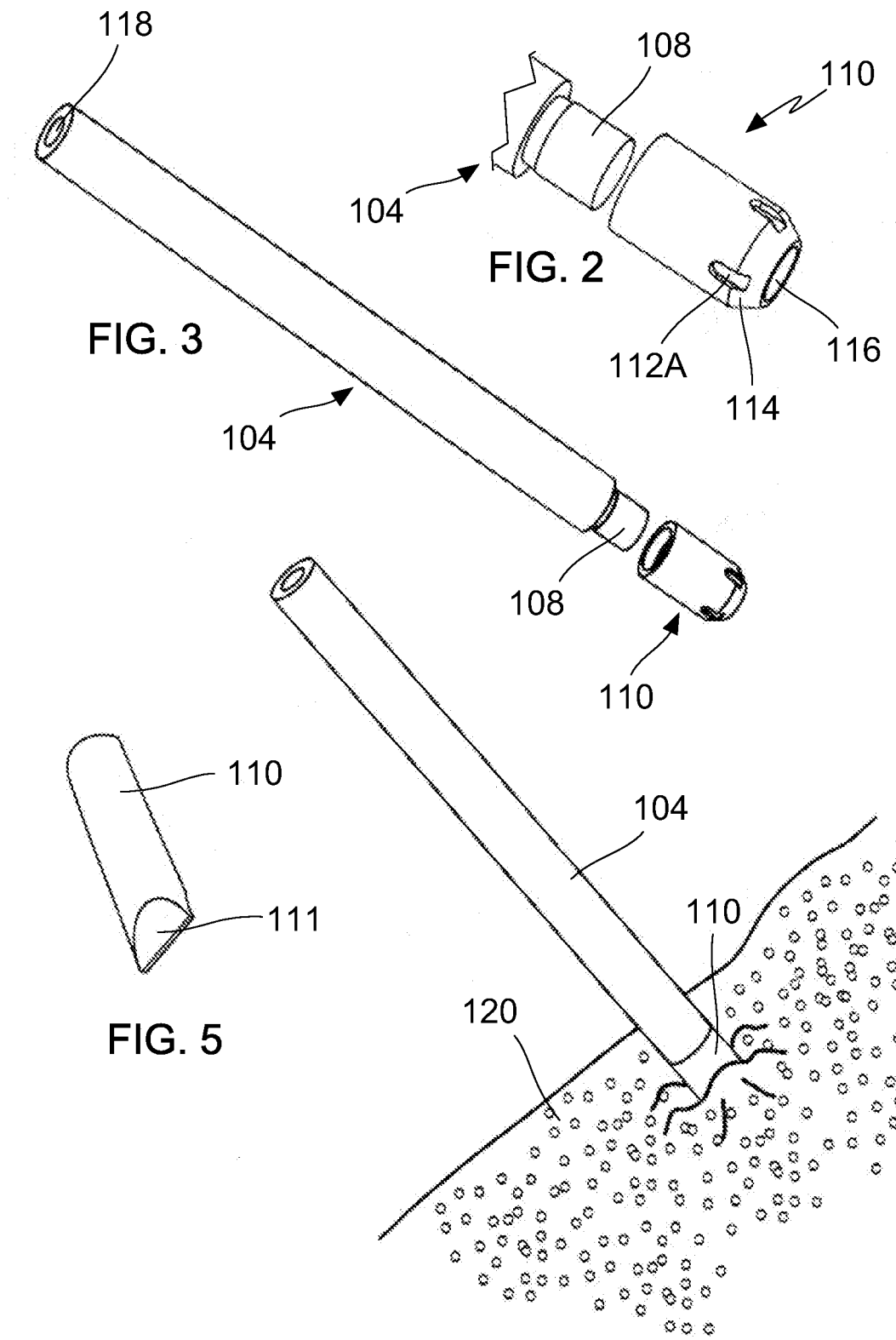

METHODS AND DEVICES FOR UTILIZING BONDABLE MATERIALS

CROSS REFERENCE TO RELATED APPLICATIONS

This non-provisional application is based upon and herein claims priority to U.S. Provisional No. 61/155,133 filed Feb. 24, 2009. This application is related to U.S. patent application Ser. No. 12/202,210 filed Aug. 28, 2008, U.S. patent application Ser. No. 11/689,670 filed Mar. 22, 2007, U.S. patent application Ser. No. 11/671,556 filed Feb. 6, 2007, and U.S. patent application Ser. No. 11/416,618 filed May 3, 2006, the entire contents of each are hereby expressly incorporated by reference into this disclosure as if set forth fully herein.

FIELD OF THE INVENTION

The invention relates to the fastening and stabilizing of tissues, implants, and bondable materials, such as the fastening of a tissue and/or implant to a bondable material, the fastening of an implant to tissue, and/or the fastening of an implant to another implant. This may involve using an energy source to bond and/or mechanically stabilize a tissue, an implant, a bondable material, and/or other biocompatible material. The present invention also relates to the use of an energy source to remove and/or install an implant and/or bondable material or to facilitate solidification and/or polymerization of bondable material.

BACKGROUND OF THE INVENTION

Body tissue often requires repair and stabilization to address weak or fractured bone, torn ligament or tendon, ripped muscle, or separation of soft tissue from bone. There are numerous methods to facilitate this repair and stabilization. For example, weak or fractured bones can be reinforced with bondable material, i.e. bone cement. Over time, these bondable materials may loosen due to tissue deterioration, improper installation of bondable materials, or deterioration of the bondable materials over time. Conventional procedures require removal of the bondable material, which is time consuming and potentially damaging to the tissue. After the bondable material is sufficiently removed using conventional methods, bondable material is reapplied to the tissue. Therefore, previous stabilization methods provided for the reapplication of bondable materials and did not utilize existing bondable materials. There is a need for an improved method to utilize existing bondable materials to stabilize tissue and implants.

In another example, bondable materials are used for the installation of implants, i.e. example bone cement. However, some implants loose stability over time. Previous stabilization methods require removal of the implant and the remaining bondable material left on the bone. After the bondable materials are removed, new bondable material is applied to the implant and/or bone. Again, this is a time consuming process, potentially damaging the surrounding tissue during the removal of the implant and remaining bondable material.

Bone plates may be positioned internal to the skin, i.e. positioned against the fractured bone, or may be positioned external to the skin with rods connecting the bone and plate. Conventional bone plates are particularly well-suited to promote healing of the fracture by compressing the fracture ends together and drawing the bone into close apposition with other fragments and the bone plate. However, one drawback with plates and screws is that with the dynamic loading placed on the plate, loosening of the screws, and loss of stored compression can result. There is a need for additional fixation devices and methods related to bone plates and other implants providing support to bone.

In addition to internal or external bone plates, surgeons sometimes use intramedullary rods to repair long bone fractures, such as fractures of the femur, radius, ulna, humerus, fibula, and tibia. The rod or nail is inserted into the medullary canal of the bone and affixed therein by screws or bolts. After complete healing of the bone at the fracture site, the rod may be removed through a hole drilled in the end of the bone. One problem associated with the use of today's intramedullary rods is that it is often difficult to treat fractures at the end of the long bone. Fastener members, such as bolts, are positioned through the cortical bone and into threaded openings in the rod. However, the number and positioning of the bolt/screw openings are limited at the tip of the rod because of the decreased surface area of the rod and the reduced strength at the tip of the rod. Fractured bone sections at the distal end of a femur, for example, may not be properly fastened to using conventional intramedullary rod stabilization techniques. Therefore, additional fixation devices and methods are required for use with intramedullary rods.

Other common methods to address weak or fractured bones use a combination of bone screws, bone plates, and intramedullary rods. Conventional methods of using bone screws required a sufficient depth within the bone to stabilize a bone plate. However, weak or fracture bones have limited purchase, as portions of the bone may be unfit for the use of bone screws. Furthermore, if a intramedullary rod has been used to stabilize the bone, the fixation area is further limited as surgeons generally avoid tapping into areas of bone with an underlying intramedullary rod. An improved method of stabilizing existing bone plates and intramedullary rods is needed.

Existing systems and techniques for repairing tissue, like the ones previously described, can be complex, time consuming, lack the characteristic of being employed with precision, be damaging to tissue, and/or fail to provide a robust fastening of tissue. Therefore, there is a need for an apparatus and method for the fastening of tissue that involves a reduction in completion time, greater strength and precision, utilization of previously implanted materials, and preservation of living tissue. There is a need for a system that utilizes of previously installed fixation devices and techniques.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIG. 2 illustrates an embedding implant and end effector of the invention;

FIG. 3 illustrates an alternative view of FIG. 2;

FIG. 4 illustrates an embedding implant connected to an end effector and embedded in a bondable material;

FIG. 5 illustrates an alternative welding horn or embedding implant of the invention;

SUMMARY

Figure 1:
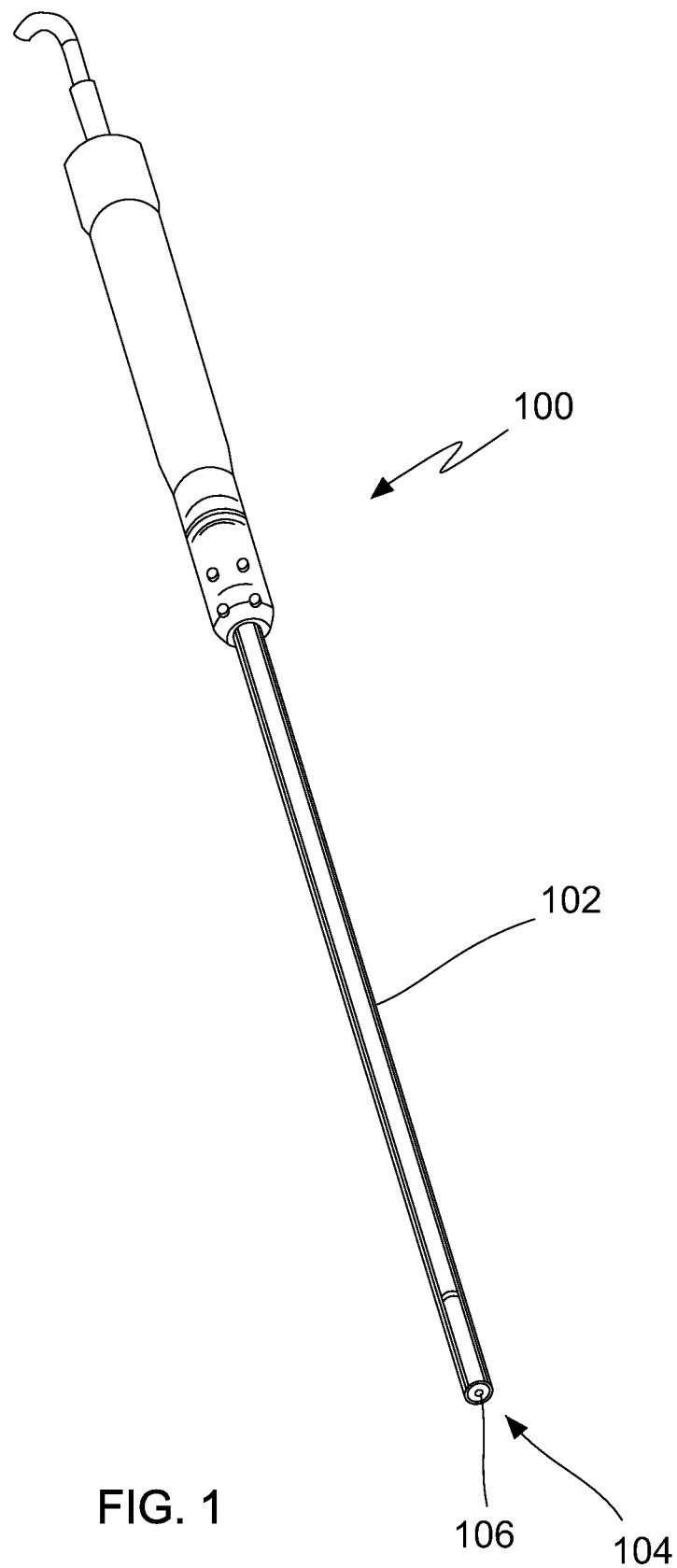
FIG. 1 is a perspective view of an exemplary vibratory energy device.
Figure 6:
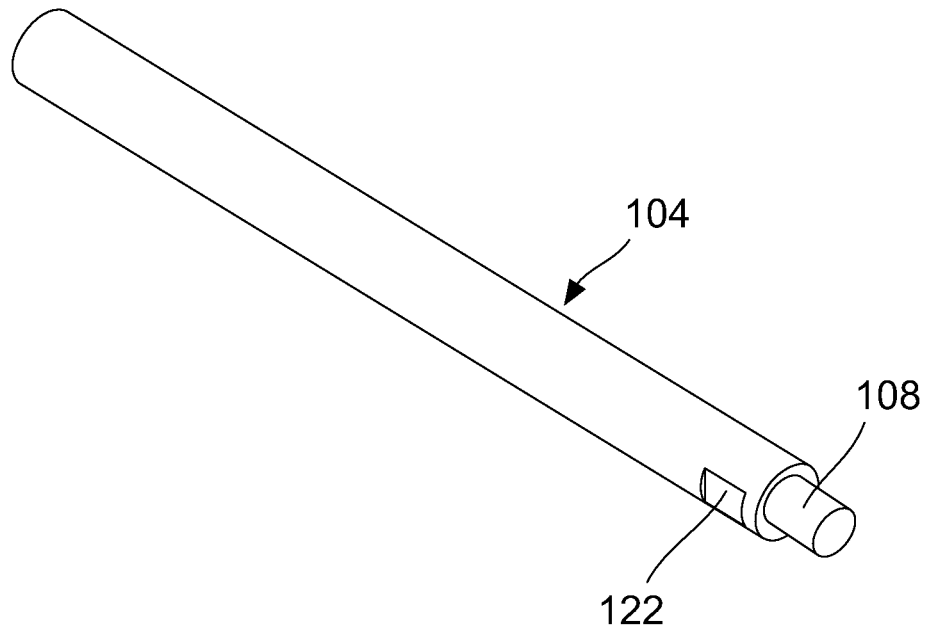
FIG. 6 illustrates an alternative configuration of the end effector of FIG. 3.
Figure 7:
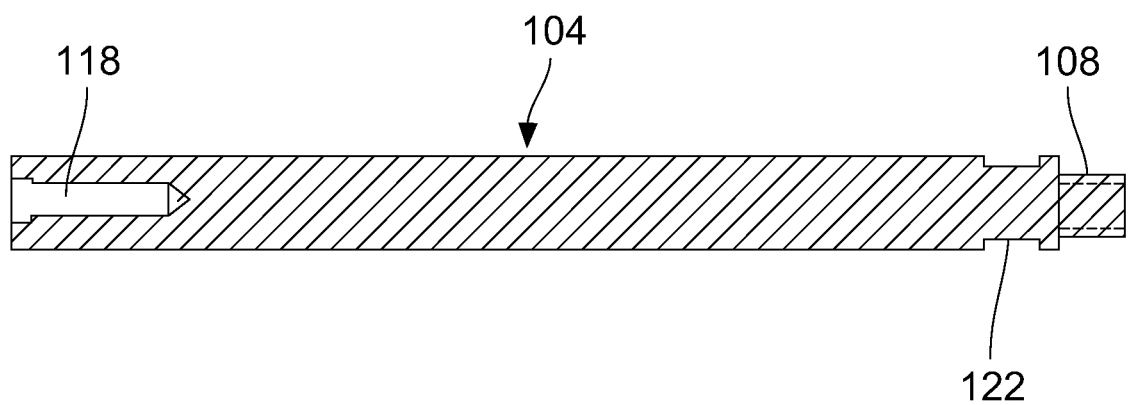
FIG. 7 illustrates a cross section through the center of a long axis of the end effector of FIG. 6.

As is described in further detail below, fasteners may be embedded within solidified bondable material, for example a grouting agent such as bone cement (PMMA) or other acrylic based material. In an embodiment in accordance with the invention, an embedding fastener may be connected to an end effector of a vibratory energy generator. The embedding fastener may be adapted to enter and engage the bondable material that has been locally melted by vibratory energy, and to be securely retained therein once the bondable material has cooled and hardened.

The end effector may be provided in any of a variety of shapes, one example being an elongated rod or shaft, connectable to a hand piece at a proximal end, and operative to transmit vibratory energy at a distal end. The fastener may be adapted to connect to the distal end of the end effector, for example by mechanical interlocking, threading, twist lock configurations, friction fitting, or adhesive attachment. The mechanical connection must be operative, however, to communicate the vibratory energy from the end effector to the fastener.

The fastener is adapted to be securely retained within the bondable material or adhesive, in one embodiment, by being provided with a shaped or contoured surface upon which the adhesive may grip once hardened. A roughened or porous surface may be provided alone or in combination with a shaped surface to increase purchase in bondable material and/or facilitate an interference fit.

The fastener may further be provided with a taper at a leading end which first enters the adhesive. The taper improves performance, at least, by promoting accurate tracking and movement of the fastener into the adhesive, piercing tissue, and facilitating initial melting by concentrating vibratory energy over a smaller surface region.

In a further embodiment of the invention, the embedded bone cement fastener (also referred to as an embedding fastener or embedding implant) described above is provided with one or more radial gaps, chambers, or ports, extending from a central bore. A polymeric fastener is inserted within the central bore, and vibratory energy is applied to the polymeric fastener, whereby polymer at the interface between the embedded fastener and the polymeric fastener melts. When the polymer melts, and particularly as pressure is applied to the polymeric fastener in the direction of insertion, polymer enters the ports, flowing in a direction away from the central bore. When vibratory energy is discontinued, the polymer solidifies, and the polymer fastener is thereafter secured within the embedding fastener.

The embodiments of the present invention may be utilized with limitless fixation techniques and in conjunction with other fasteners and implants. Furthermore, the embodiments herein may assist in the installation and removal of tissue and implants. Moreover, the embodiments of the present invention may assist in the delivery of therapeutic agents and employ methods that facilitate tissue growth and repair. In addition, the embodiments herein may be used to apply vibratory energy to remove and/or install an implant in bondable material or to facilitate solidification and/or polymerization of the bondable material.

DETAILED DESCRIPTION

The invention relates to the devices and methods for the utilization of bondable materials and bondable materials, fixation and fastening of tissue to tissue, an implant to tissue, and an implant to an implant both inside and outside the body. The invention additionally relates to removing and anchoring implants to bondable materials and/or other biocompatible materials, anchoring implants using previously implanted and hardened bondable materials, and fixation using vibratory energy, mixing, solidifying, bonding, and/or mechanical interlocking of materials. The present invention also relates to the use of an energy source to install and/or remove an implant or bondable material or to facilitate the solidification and/or polymerization of a bondable material The methods and devices disclosed herein may be used in conjunction with any medical procedure on the body. The stabilization, fastening, and/or repair of tissue or an implant may be performed in connection with any medical procedure related to a joint, bone, muscle, ligament, tendon, cartilage, capsule, organ, skin, nerve, vessel, or other body parts. For example, tissue may be stabilized during intervertebral disc surgery, kyphoplasty, knee surgery, hip surgery, organ transplant surgery, bariatric surgery, spinal surgery, a+nterior cruciate ligament (ACL) surgery, tendon-ligament surgery, rotator cuff surgery, capsule repair surgery, fractured bone surgery, pelvic fracture surgery, avulsion fragment surgery, shoulder surgery, hernia repair surgery, and surgery of an intrasubstance ligament tear, annulus fibrosis, fascia lata, flexor tendons, etc.

Also, an implant may be inserted within the body and fastened to tissue with the present invention. Such implant insertion procedures include, but are not limited to, partial or total knee replacement surgery, hip replacement surgery, shoulder replacement surgery, bone fastening surgery, etc. The implant may be an organ, partial organ grafts, tissue graft material (autogenic, allogenic, xenogenic, or synthetic), collagen, a malleable implant like a sponge, mesh, bag/sac/pouch, collagen, or gelatin, or a rigid implant made of metal (porous or nonporous), polymer, composite, or ceramic. Collagen may be provide the benefit of bolstering tissue growth. Additionally, a dessicated collogen may be used to absorb surrounding fluid, which may provide the additional benefit of applying pressure on the tissue being repaired. Other implants include breast implants, biodegradable plates, porcine or bovine patches, metallic fasteners, compliant bearing for medial compartment of the knee, nucleus pulposus prosthetic, stent, suture, suture anchor, tissue graft, tissue scaffold, biodegradable collagen scaffold, and polymeric or other biocompatible scaffold. The scaffold may include fetal cells, stem cells, embryonic cells, enzymes, and proteins.

In this application, the term "bondable" or "bondable material" is used to refer to the materials discussed herein, as well as any material, suitable for in vivo applications, which can be softened and made flowable by the application of heat (such as heat produced with vibratory energy such as ultrasonic energy), and which, when softened, may become tacky and will bond to other materials and will flow to fill available space. Thus, the material may be thermoplastic, but it may also exhibit tackiness or bonding ability when in its plastic form. Many materials suitable for in vivo applications are made of or incorporate such bondable materials. Generally speaking, the amount of heat needed to soften and make flowable should be within a temperature range that does not produce substantial thermal tissue necrosis. Alternatively stated, the amount of heat required to soften the bondable material during vibratory bonding is substantially confinable, due to the thermal properties of the bondable material, to an area of contact between the objects which are being bonded, thereby protecting living body tissue near the contact between the two objects from substantial thermal tissue necrosis. Any embodiment herein may be used with any of the materials and/or applications disclosed herein or known in the art.

The fixation and fastening system and other embodiments of the present invention contemplates the use any materials that may include or be used in conjunction with bondable materials for bonding and/or staking within the human body. Implants that may be used as fasteners may also be referred to as fastening implants. Bondable material used may include, but are not limited to, biocompatible, degradable, biodegradable, bioerodible, bioabsorbable, mechanically expandable, hydrophilic, bendable, deformable, malleable, riveting, threaded, toggling, barded, bubbled, laminated, coated, blocking, pneumatic, one-piece, multi-component, solid, hollow, polygon-shaped, pointed, self-introducing, and combinations thereof. Also, the devices may include, but are not limited to, metallic material, polymeric material, ceramic material, composite material, body tissue, synthetic tissue, hydrophilic material, expandable material, compressible material, bondable material, and combinations thereof. Bondable material may also include polymethyl methacrylate (known as "PMMA" or "bone cement"), glue, adhesive, and/or other grouting agents or acrylic materials used for fixation.

In this application, "bond", "bonded", and "bonding" includes, but is not limited to, attaching, engaging, connecting, binding, adhering, and/or fastening one or more materials through resistive heating, mechanical interlocking, application of force, application of grouting agents (i.e. bone cement), adhesives and/or solvents, spraying, radiofrequency, vibratory energy (i.e. ultrasound), microwave, laser, electromagnetic, electro shockwave therapy, plasma energy (hot or cold), and other suitable method described herein or known in the art.

Preferably, materials of the present invention can melt with the application of energy, becoming gel-like, tacky, and/or soft. The energy source and the technique used to bond and/or stake the material within the body can be selected to minimize or avoid damage to surrounding body tissue. Exemplary materials that may be used may include polymers, ceramics, composites, and metals, although other materials may also be suitable for use with the invention. While the present invention contemplates the use of any of these materials in any of the following embodiments, polymeric material is used in the following examples and description simply to illustrate how the invention may be used.

There are a limitless number of materials may be used for the present invention. Examples of amorphous polymers are polycarbonate (LEXAN), polystyrene, polysulfone (ULDALL), and acrylics polycarbonate (ABS and styrenes). Examples of semi-crystalline polymers include acetyl (DELRIN), nylon, polyester, polyethylene, polyether ether ketone, polypropylene, polyvinylchloride (PVC), and Caprolactam. Biodegradable semi-crystalline polymers may include polylactic acid and polyglycolic acid. Copolymers of PGA and PLA may also be used. Poly-l-lactide (PLLA) or other forms of PLA may also be used. Other polymers which may be used with the present invention, either as a thermoplastic or non-thermoplastic, are polyethylene glycol (PEG)-copolymers and D,L-lactide-co-glycolide polyesters. Some semi-crystalline materials are particularly suitable for surgical bonding and/or staking, especially vibratory bonding and staking. Examples of such materials include PAEK (polyaryletherketone), including PEEK (polyetheretherketone) and PEKK (polyetherketoneketone).

In addition to PEEK and the other polymers described herein, the implants, devices, and methods of the present invention may use keratin, a naturally occurring polymer. Keratin may be vibratory bonded or staked to itself, to other implants, or within tissue. This may be performed in the operating room or intracorporeally. Keratin may be bonded to collagen or to other known polymers. In an exemplary application, keratin may be used to fasten tissue to bone since keratin has BMP and tissue scaffold properties. It is contemplated that any of devices and methods disclosed herein may utilize keratin alone or in combination with PEEK, polylactic acid, or other polymer. Keratin may be used to make fasteners, disc replacements, joint replacement components, stents, cell scaffolds, drug reservoirs, etc. Also, joint bearing surfaces may include keratin with or without collagen or chondrocytes. The bearing surfaces may be fastened to a joint component using PEEK or PLA fasteners.

Another polymer that can be used with the present invention is a class of natural materials, called polyhydroxyalkanoates, or PHA polymers. These polymers are synthesized in nature by numerous microorganisms, and they have been recently recognized as the fifth class of naturally occurring biopolymers (along with the polyamino acids, polynucleic acids, polysaccharides, and polyisoprenoids). Unlike the other naturally occurring biological polymers, however, the PHA polymers are thermoplastic, i.e. they may be repeatedly softened with heat and hardened with cooling. As such, these polymers can be processed much like other plastics. A specific example of a PHA polymer that could be used is poly-4-hydroxybutyrate material. Such PHA polymers are available from Tepha Inc of Lexington, Mass.

Fasteners of the invention may utilize or be coated with polymethylmethacrylate (PMMA), in order to promote bonding with PMMA used in the body, or PMMA could be incorporated into polymer of the fastener, or deposited within cavities or shapes formed in the fastener surface, including threaded, roughened, porous, or nano textures. A fastener may be thus coated with PMMA, or formed entirely of PMMA, and may be heat bonded, advantageously using ultrasound, to another PMMA surface or other adhesive surface, otherwise as described herein with respect to bone cement. Although PMMA, known generally as bone cement, and other polymers may function more as a grouting agent than a cement or adhesive. The term "bondable material" is used throughout the specification for simplicity.

In accordance with the invention, metals are advantageously connected with fasteners incorporating polymeric materials. Any of a variety of metals may be used, either smooth or formed with at least portions formed of metal, or a roughened or porous surface, or formed with cavities or other shapes upon which polymeric material may mold, enter, adhere, or otherwise affix. The polymer is softened in accordance with the invention through the application of heat, including heat created using vibratory energy, to become tacky, or sufficiently softened in order to bond on a microscopic level, or a macroscopic level through adaptation to the surface structure of the metal. For use in vivo, biocompatible metals are used, including stainless steel, nitinol or other SMA (shape metal alloy), tantalum, porous tantalum, titanium, cobalt-chrome alloys, and other metals such as are known to those skilled in the art. Additional related information, including bonding polymers and metals, and polymer to polymer bonding of implant materials, may be found in U.S. Pat. No. 5,163,960 entitled "Surgical devices assembled using bondable materials", and U.S. Pat. No. 7,104,996 entitled "Method of performing surgery", the contents of each of which being incorporated herein by reference.

The fastening device of the present invention may include therapeutic substances to promote healing. These substances could include antibiotics, hydroxypatite, anti-inflammatory agents, steroids, antibiotics, analgesic agents, chemotherapeutic agents, bone morphogenetic protein (BMP), demineralized bone matrix, collagen, growth factors, autogenetic bone marrow, progenitor cells, calcium sulfate, immo suppressants, fibrin, osteoinductive materials, apatite compositions, germicides, fetal cells, stem cells, enzymes, proteins, hormones, cell therapy substances, gene therapy substances, and combinations thereof. These therapeutic substances may be combined with the materials used to make the device. Alternatively, the therapeutic substances may be impregnated or coated on the device. Time-released therapeutic substances and drugs may also be incorporated into or coated on the surface of the device. The therapeutic substances may also be placed in a bioabsorbable, degradable, or biodegradable polymer layer or layers.

The therapeutic agents may also be placed within one or more cavities disposed in a fastening device of the present invention. Different agents may be disposed in different cavities of the device to specifically tailor the implant for a particular patient. Dosages of the therapeutic agent may be the same or different within each of cavities as well. The cavities may include a cover which may release the agent in a controlled or timed manner. The cover may be biodegradable or bioerodible to allow the agent to release to surrounding tissue. Examples of suitable therapeutic agents include bone growth inducing material, bone morphogenic proteins, osteoinductive materials, apatite compositions with collagen, demineralized bone powder, or any agent previously listed. U.S. patent application Ser. No. 11/549,994 entitled "Drug Eluting Implant" discloses means for delivering therapeutic agents. The above-mentioned patent application is incorporated by reference herein in its entirety.

The fastening devices of this and other embodiments of the invention may be used in combination with fasteners in the prior art. Examples of fasteners, implants, and their methods of employment may be found in U.S. Pat. Nos. 5,163,960; 5,403,348; 5,441,538; 5,464,426; 5,549,630; 5,593,425; 5,713,921; 5,718,717; 5,782,862; 5,814,072; 5,814,073; 5,845,645; 5,921,986; 5,948,002; 6,010,525; 6,045,551; 6,086,593; 6,099,531; 6,159,234; 6,368,343; 6,447,516; 6,475,230; 6,592,609; 6,635,073; and 6,719,765. Other fastener types are disclosed in U.S. patent application Ser. Nos. 12/202,210; 10/102,413; 10/228,855; 10/779,978; 10/780,444; and 10/797,685. The above cited patents and patent applications are hereby incorporated by reference in their entirety.

With reference to FIG. 1, any known energy emitting instrument may be used with the surgical system of the present invention. Instrument 100 may produce energy such as resistive heating, radiofrequency, ultrasound (vibratory), microwave, laser, electromagnetic, electro shockwave therapy, plasma energy (hot or cold), and other suitable energy disclosed herein or known in the art. FIG. 1 illustrates an exemplary handpiece or instrument 100 that may be used with the present invention. The instrument 100 may be a vibratory energy generator with a sheath 102 to cover and protect the end effector 104 and engage a fastener/implant near engagement feature 106. As will be discussed below, the instrument may be used to bond and/or mechanically interlock fasteners and other embodiments the present invention. Additional embodiments of instrument 100 are disclosed in U.S. patent application Ser. No. 12/202,210 entitled "Methods and Devices for Utilizing Thermal Energy to Bond, Stake and/or Remove Implants", which is incorporated by reference herein.

With reference to FIGS. 2-7, end effector 104 may be utilized with anchor or embedding fastener 110. Embedding fastener 110 may also be referred to as an embedding implant. FIG. 2 illustrates end effector 104 that connects to embedding fastener 110 with distal end 108. The connection between distal end 108 and embedding fastener 110 may utilize threads, magnetism, friction, taper, ball and socket, linkage, adhesive, interlocking shapes, and other connections known in the art. Additionally, distal end 108 and embedding fastener 110 may be permanently or detachably connected.

As shown in FIG. 2, embedding fastener 110 may further be provided with a taper 114, which first enters bondable material 120 in FIG. 4. Taper 114 may improve performance, for example, by promoting accurate tracking and movement of embedding fastener 110 into bondable material 120, piercing body tissue, and facilitating initial melting by concentrating vibratory energy over a smaller surface region. Although embedding fastener 110 may be made of any material described herein or known in the art, it may be preferable to use titanium.

As discussed in further detail below, embedding fastener 110 may also have feature 112 and/or feature 116, either or both may be a surface feature, recess, or pass through a portion or the entirety of embedding fastener 110.

Referring to FIG. 3, an embodiment of end effector 104 may have proximal end 118 to the other components of instrument 100. The connection between instrument 100 and proximal end 118 may be threaded, magnetic, friction, hex, ball and socket, linkage, adhesive, and other methods disclosed herein or known in the art.

As shown in FIGS. 3-7, end effector 104 may be provided in any of a variety of shapes, one example being an elongated rod or shaft, connectable to a hand piece at a proximal end 118, and operative to transmit vibratory energy at a distal end 108. While a rod shape is shown and selected for reduced manufacturing cost, end effector 104 may have the form of box or hex channel, oval or other shape, provided it communicates vibratory energy to a distal end 108, an attached fastener, or embedding fastener 110. Additionally, feature 111 of FIG. 5 may be used on embedding fastener 110 or integrated into end effector 104 (not shown).

In an additional embodiment, embedding fastener 110 is adapted to connect to distal end 108 of end effector 104 by mechanical interlocking, as by a bore in embedding fastener 110, sized to receive distal end 108 of end effector 104, optionally provided with internal or external threading (not shown), wherein post 108 has mating threads. Additionally, the connection may be threaded, magnetic, friction, hex, ball and socket, linkage, adhesive, and other methods disclosed herein or known in the art. Similarly, a bore or aperture may be provided in end effector 104, mateable with a post or projection on embedding fastener 110. Other mechanical connections are contemplated, including twist lock configurations, friction fitting, or adhesive attachment. The mechanical connection should preferably be operative to communicate vibratory energy from end effector 104 to embedding fastener 110, as by a firm mechanical connection.

As shown in an embodiment of FIG. 4, embedding fastener 110 may be adapted to be securely retained within bondable material 120 by being provided with a shaped or contoured surface upon which the softened bondable may adhere. A roughened or porous surface may be provided alone or in combination with shaped surface thereby providing for increased purchase in bondable material 120.

With reference to FIG. 4, embedding fastener 110 may be embedded within solidified bone bondable material 120, for example PMMA, acrylic based adhesive, or other bondable materials. In the present invention, embedding fastener 110 is connected to end effector 104 of an embodiment of instrument 100, such as a vibratory energy generator as shown in FIG. 1. Embedding fastener 110 is adapted to enter and engage bondable material 120 or bondable material 120 that has been locally melted by vibratory energy (as shown in FIG. 4), through contact between embedding fastener 110 and bondable material 120 during operation of instrument 100. Embedding fastener 110 is securely retained by bondable material 120 once the latter has hardened. Although the embodiment in FIG. 4 may be used under a limitless number of configurations and settings, Table 1 is being set forth with operative examples:

TABLE 1

Titanium Embedding Fastener Bonded into PMMA

| Test Sample Number | Power (watts) | Time (sec) | Force Applied to Break (lbs.) | Deformation Depth (inches) |
|---|---|---|---|---|
| 1 | 63 | 2.56 | 46.7 | 0.116 |
| 2 | 48 | 2.01 | 61.9 | 0.119 |
| 3 | 48 | 1.58 | 32.5 | 0.109 |
| 4 | 48 | 1.47 | 31.5 | 0.098 |

Figure 8:
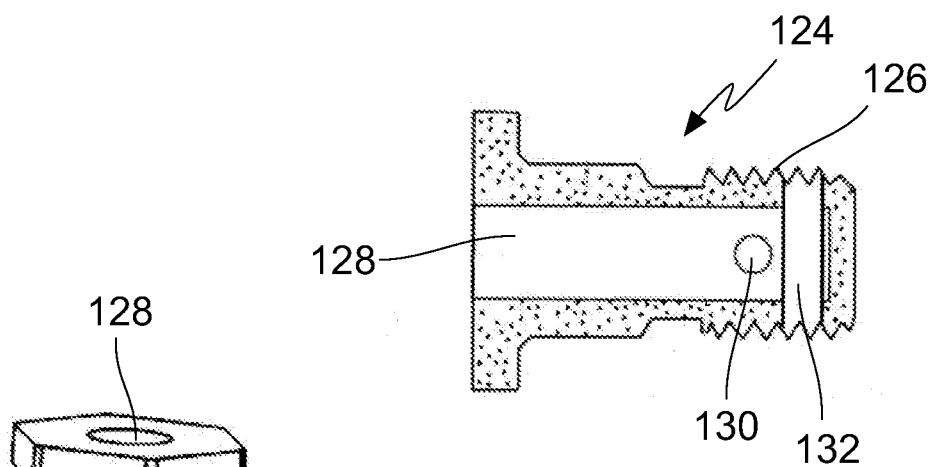
FIG. 8 illustrates a cross section through the center of a long axis of a fastening implant.
Figure 9:
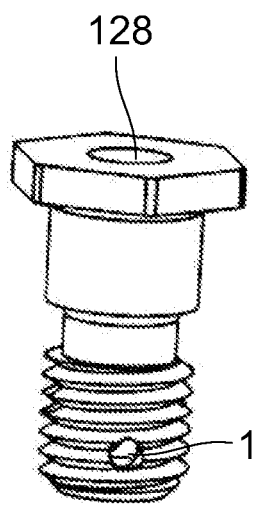
FIG. 9 illustrates an alternative view of FIG. 8.
Figure 10:
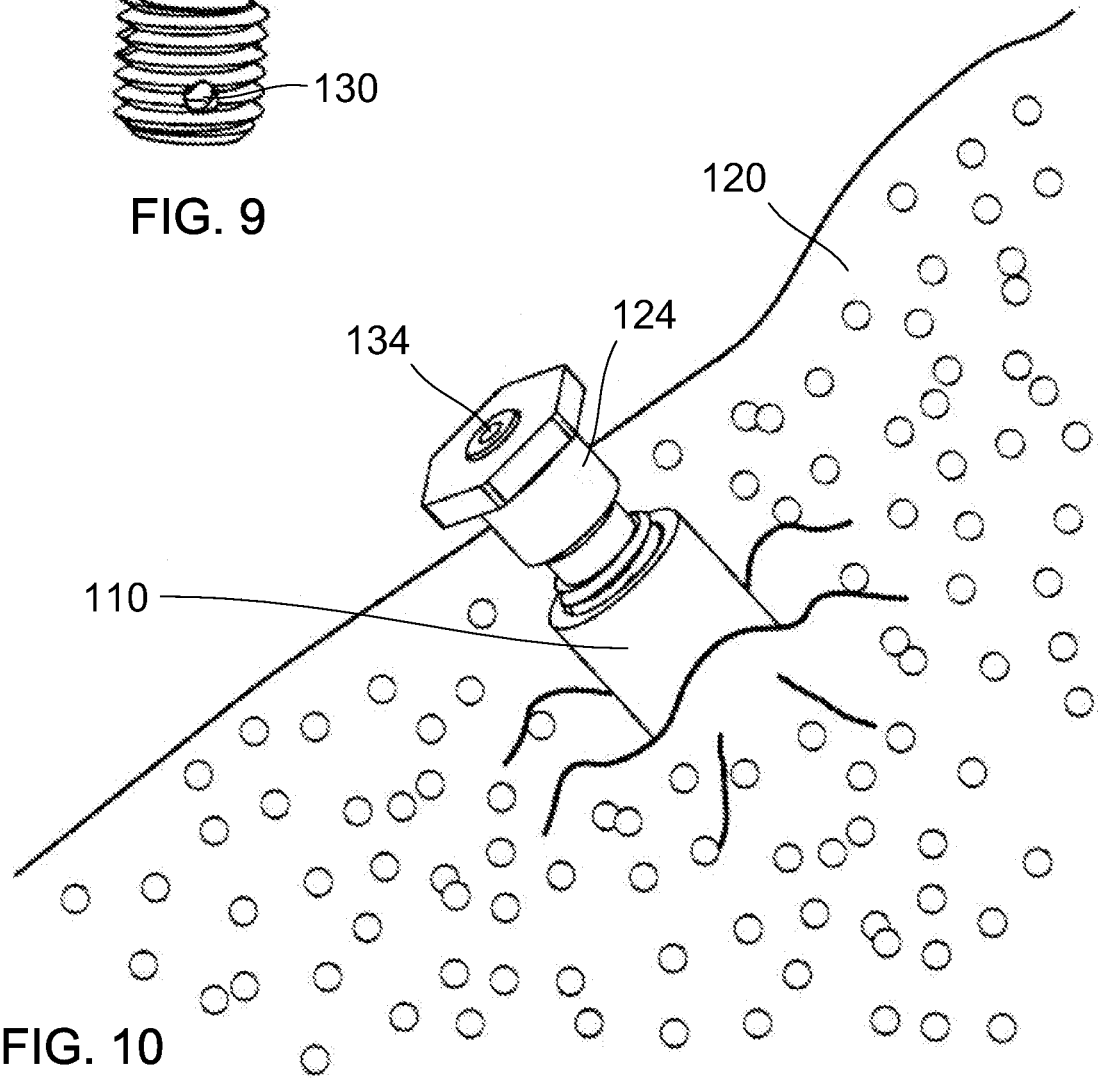
FIG. 10 illustrates the embedding implant embedded in bondable material and engaged with an fastening implant.
Figure 11:
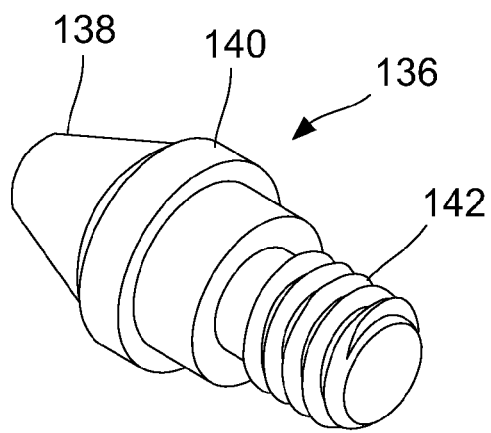
FIG. 11 illustrates an alternative configuration of the fastening implant of FIG. 9.
Figure 12:
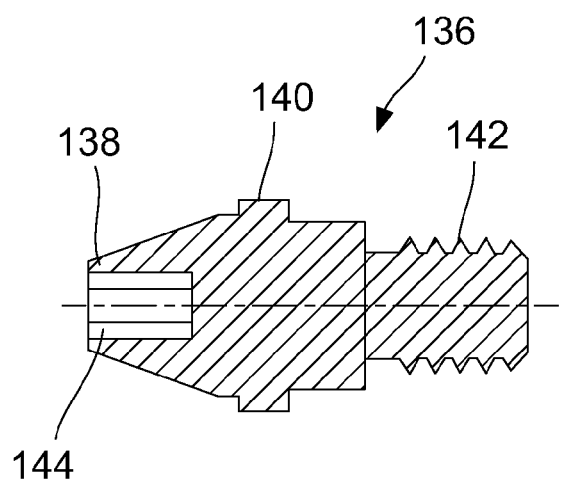
FIG. 12 illustrates a cross section through the center of a long axis of the fastening implant of FIG. 11.
Figure 20:
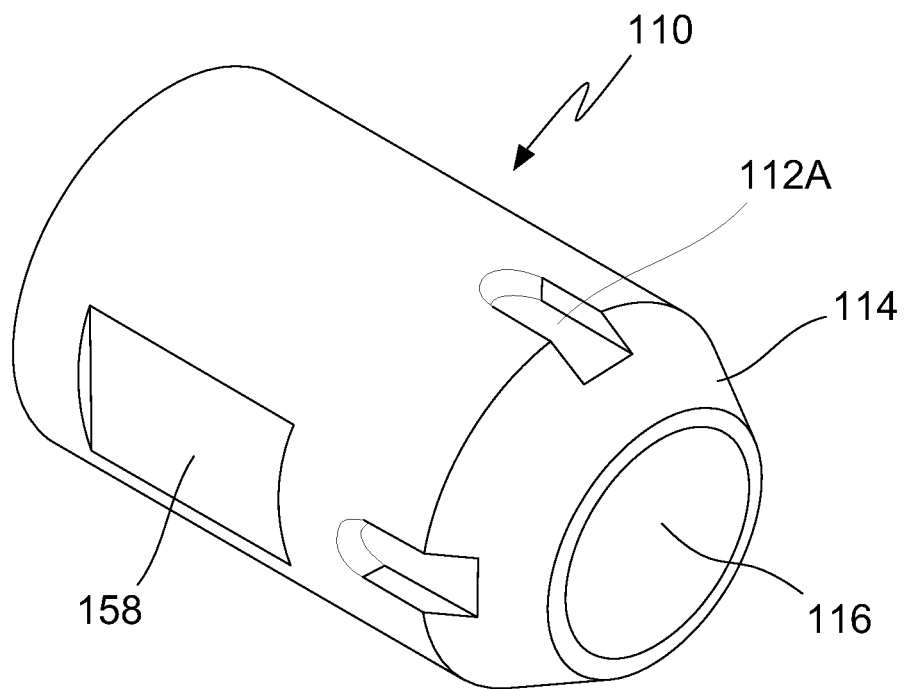
FIG. 20 illustrates an alternative configuration of an embedding implant.
Figure 21:
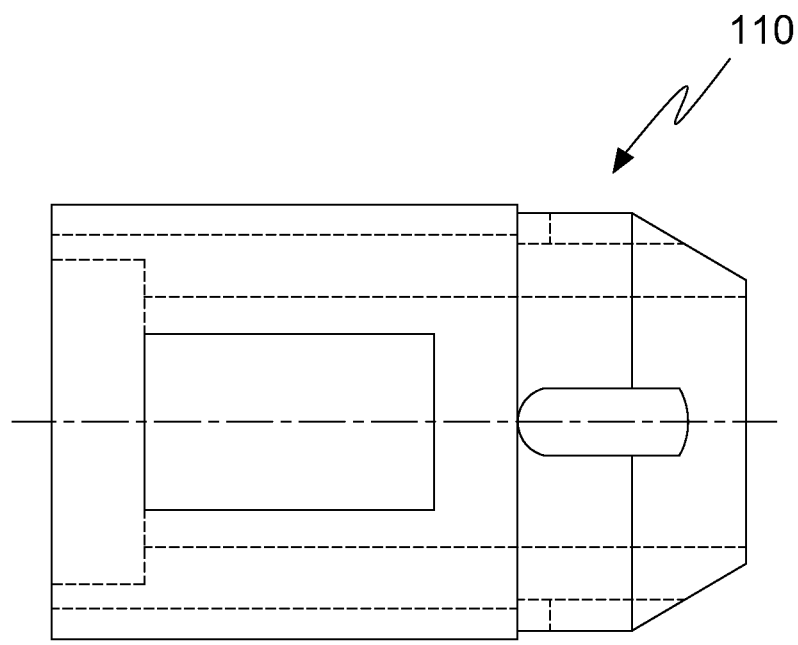
FIG. 21 illustrates a cross section through the center of a long axis of FIG. 20.
Figure 22:
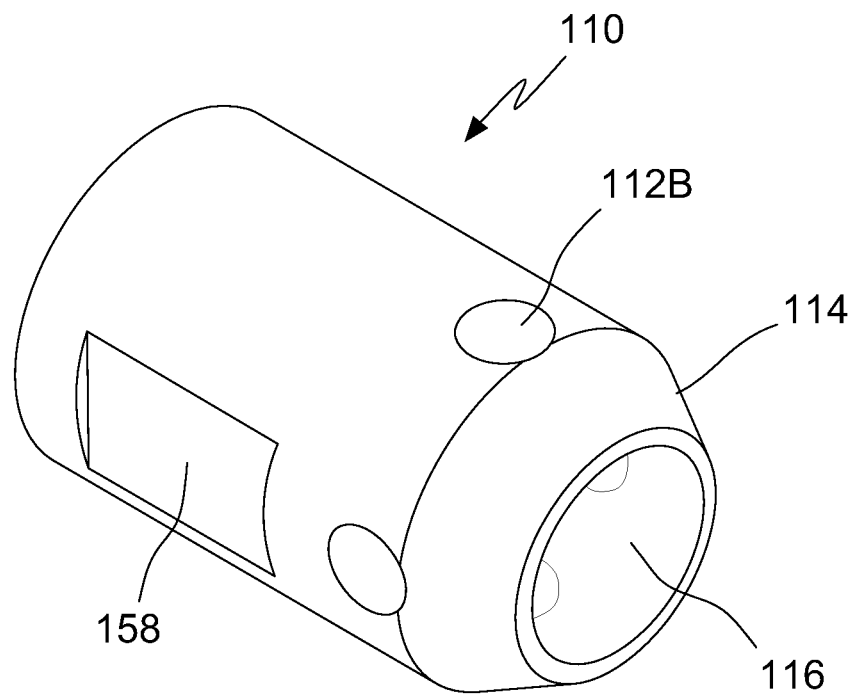
FIG. 22 illustrates an alternative configuration of the embedding implant of FIG. 2.
Figure 23:
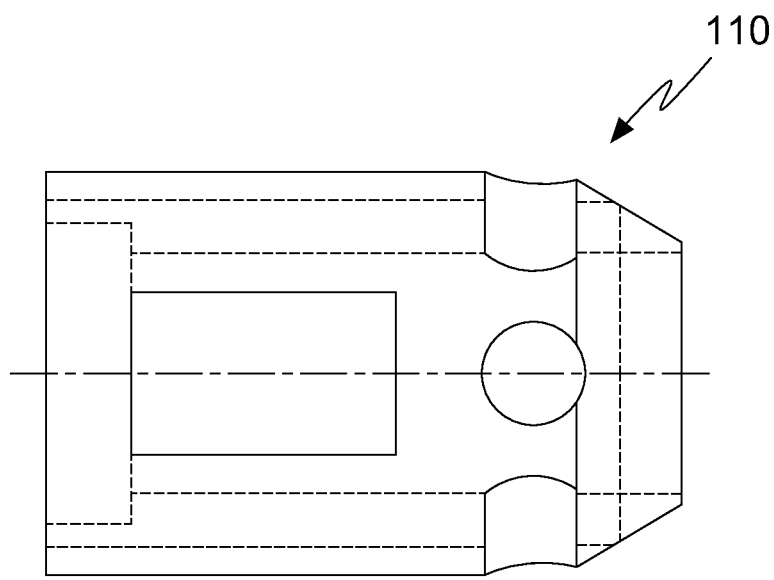
FIG. 23 illustrates a cross section through the center of a long axis of FIG. 22.
Figure 24:
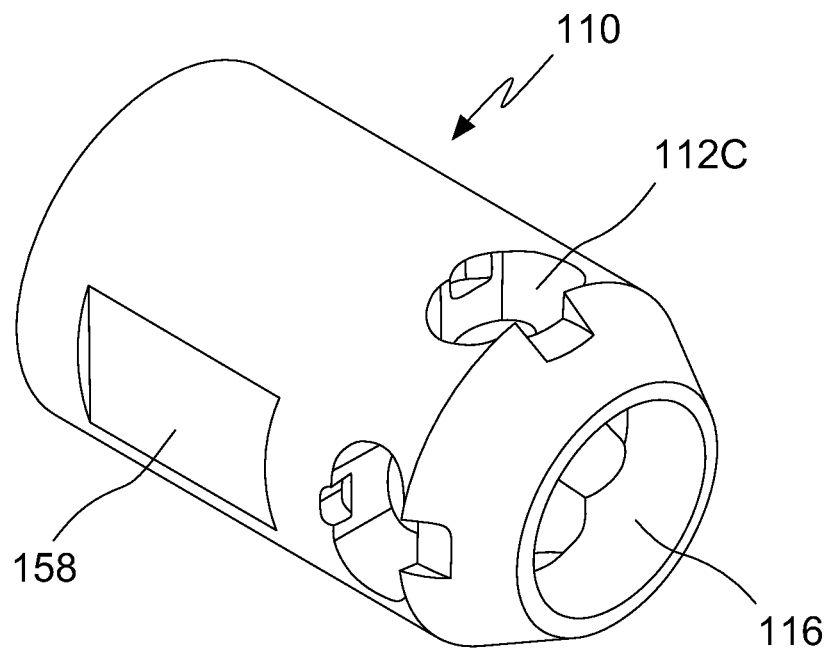
FIG. 24 illustrates an alternative configuration of the embedding implant of FIG. 2.
Figure 25:
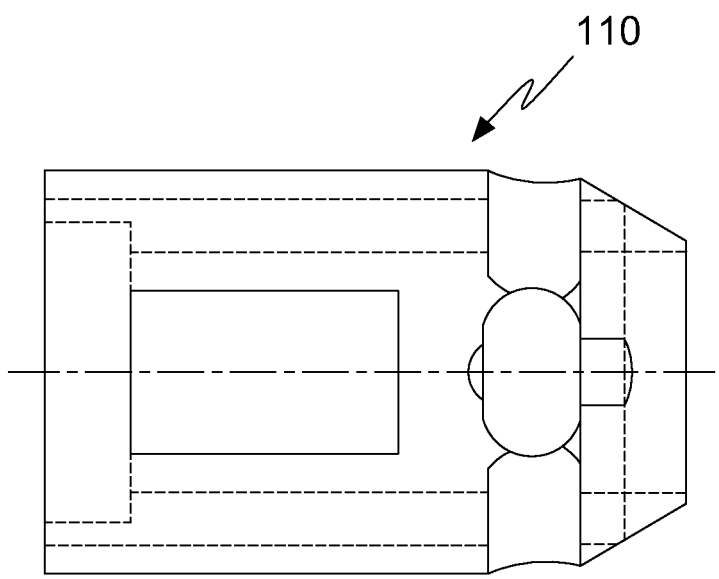
FIG. 25 illustrates a cross section through the center of a long axis of FIG. 24.

Embedding Fastener Type: Shown in FIG. 20
Instrument: Handpiece SN0105 with tuning of 39,000-45,000 Hz
System Settings:
Sample 1: 40,850 Hz, 100 W, 2.0 sec weld time
Sample 2: 40,750 Hz, 75 W, 1.5 sec weld time
Sample 3: 40,800 Hz, 75 W, 1.0 sec weld time
Sample 4: 40,750 Hz, 75 W, 1.0 sec weld time Once anchored, end effector 104 and embedding fastener 110, embedded in bondable material 120, may remain connected. Alternatively, end effector 104 may be removed and another fastener of a similar or different design may be connected to an implanted embedding fastener 110 as shown in FIGS. 8-10. In a further embodiment, fastener 124 such as described in the incorporated patents and applications may be fastened to an implanted or installed embedding fastener 110. Fastener 124 may have fastener bore 128 as shown in FIGS. 8-9. Referring to FIG. 10, a bondable insert 134 may be secured into fastener bore 128. Bondable insert 134 may be secured by press fitting, threading, or bonding to fastener bore 128 and/or embedding fastener 110. The fastener 124 may be utilized as detailed in U.S. patent application Ser. No. 12/202,210, which has been incorporated by reference herein. In further embodiments, any fastener described in the related references cited in paragraph [0001] or discussed herein may be fastened to the embedding fastener 110, then secured in its respective manner.

In an additional embodiment, embedding fastener 110 may be used to remove an implant and/or bondable material 120. For example, the ability of conventional medical tools to remove a previously installed implant or bone cement may be limited. Embedding fastener 110 may be used to obtain additional fixation. Once embedding fastener 100 is secured to the implant and/or bondable material 120, force and/or vibratory energy may be used to remove the implant and/or bondable material 120.

Figure 13:
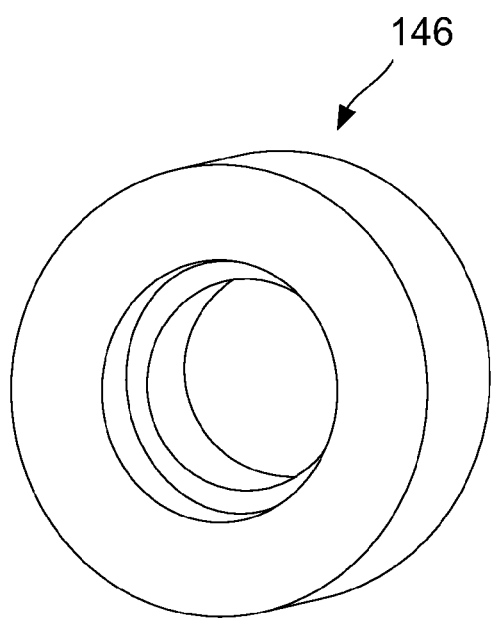
FIG. 13 illustrates a washer for use with implants of the invention.
Figure 14:
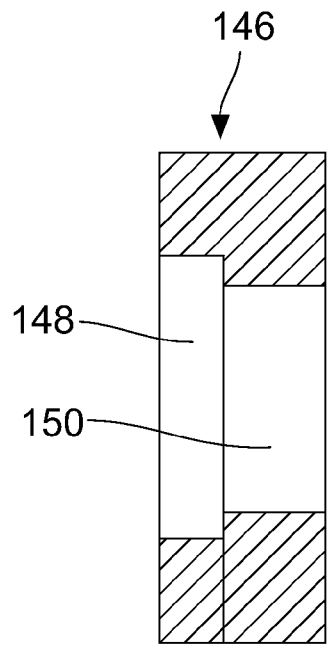
FIG. 14 illustrates a cross section through the center of a long axis of FIG. 13.
Figure 15:
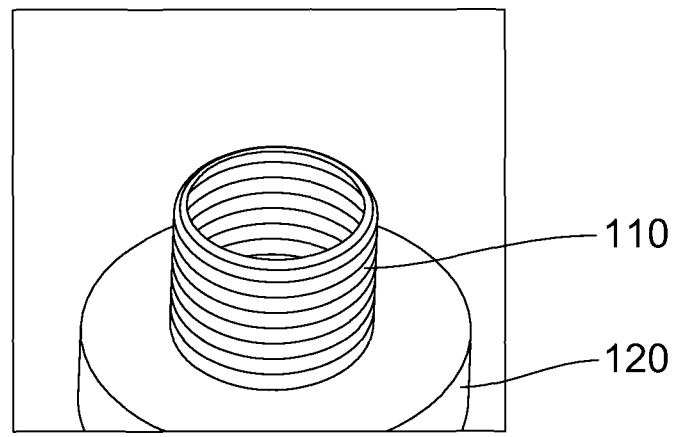
FIG. 15 illustrates embedding implant embedded in bondable material.
Figure 16:
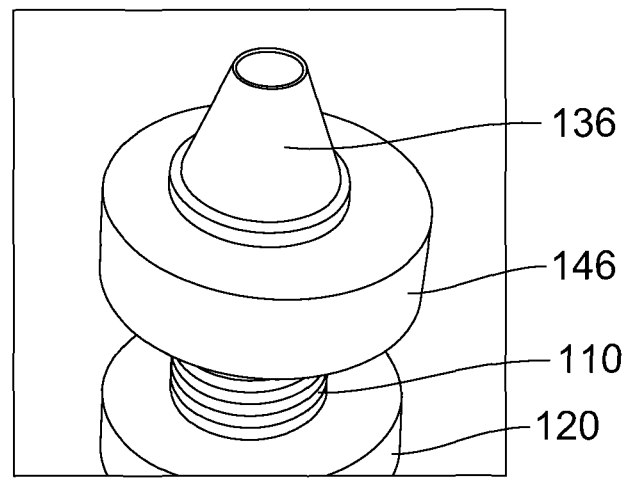
FIG. 16 illustrates the fastening implant of FIG. 11 disposed in the washer of FIG. 13 and engaged with the embedding implant of FIG. 15.
Figure 17:
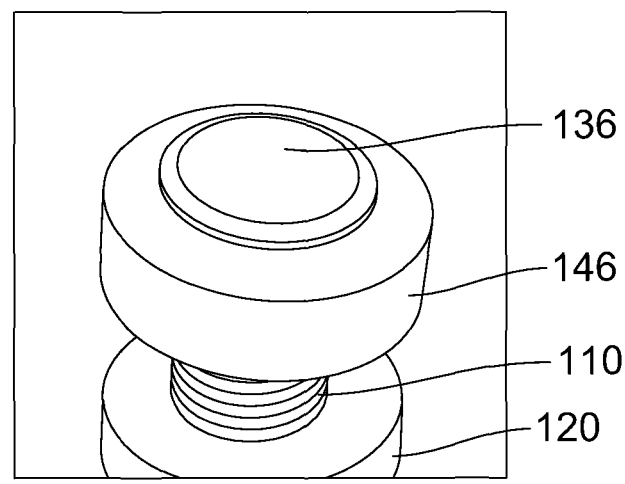
FIG. 17 illustrates the fastener of FIG. 11 bonded and/or staked to the washer of FIG. 13.

FIGS. 11-17 show an additional embodiment for use with an implanted embedding fastener 110. Fastener 136 is show in FIGS. 11-12 and washer 146 is shown in FIGS. 13-14. Although fastener 136 and washer 146 may be made of any material disclosed herein or known in the art, it may be preferable to use PEEK. After embedding fastener 110 has been secured with respect to bondable material 120, fastener 136 may be engaged into embedding fastener 110. In another embodiment, washer 146 may be used in conjunction with fastener 136 as shown in FIGS. 15-17. Additionally, fastener 136 may be bonded to embedding fastener 110 and/or washer 146.

Figure 18:
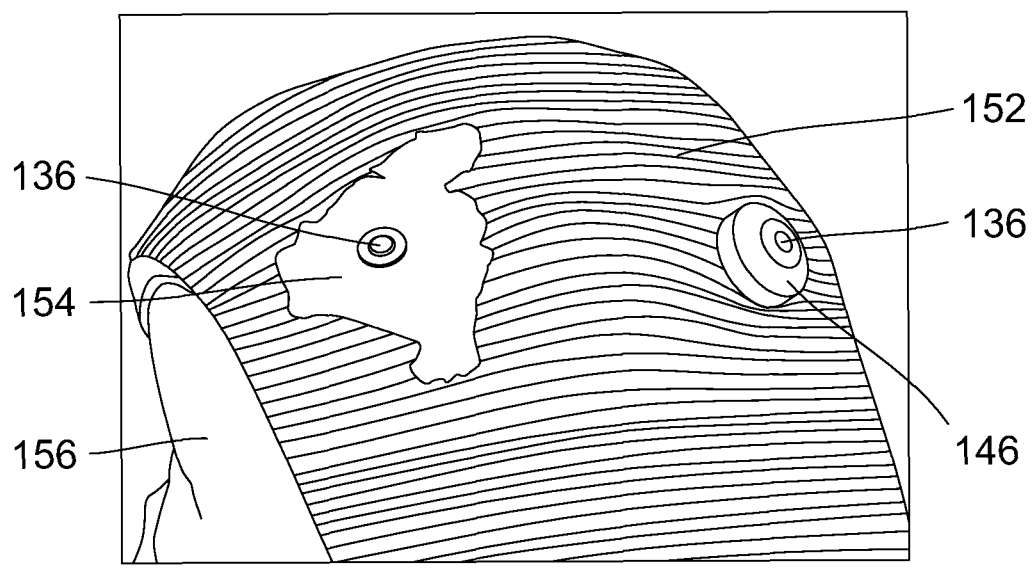
FIG. 18 illustrates alternative configurations of implant of the invention.
Figure 19:
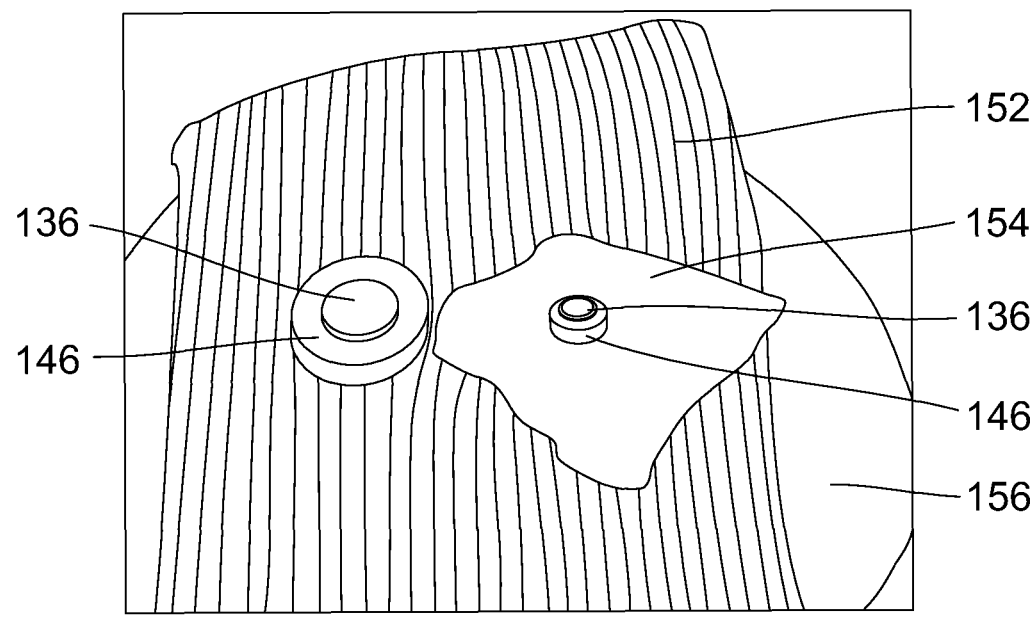
FIG. 19 illustrates alternative configurations of FIG. 18.

Referring to FIGS. 18-19, fastener 136, washer 146, and/or tissue implant 154 may be used to secure soft tissue 152 to hard tissue 156, for example to secure the rotator cuff tissue to the proximal humerus or for any other procedure disclosed herein. Additionally, washer 146 and/or tissue implant 154 could be made of collagen or other materials that promote tissue growth.

With reference to FIGS. 20-25, embedding fastener 110 may be provided with channel 112. For example, channel 112A, 112B, 112C, and/or 116 may be used. Channel 112 may extend through the surface of embedding fastener 110 to facilitate the bonding of embedding fastener 110 to bondable material 120, fastener 136, and/or any fastener disclosed herein. Channel 112 may provide a path for softened and/or molten bondable material to be displaced, providing room for entry of embedding fastener 110. Channel 116 may also include radial gaps, chambers, or ports. To accommodate for embedding fastener 110 displacing a substantial amount of material, channels may be extended along the entire length of embedding fastener 110, and may further extend along end effector 104. Channel 116 may be further operative to reduce the possibility of rotation of fastener 110 within bondable material 120. Channel 116 is thus disposed to extend into bondable material 120 after insertion, and may extend to the face of embedding fastener 110. Additionally, embedding fastener 110 may have feature 158 to help attach and remove it from end effector 104.

Figure 26:
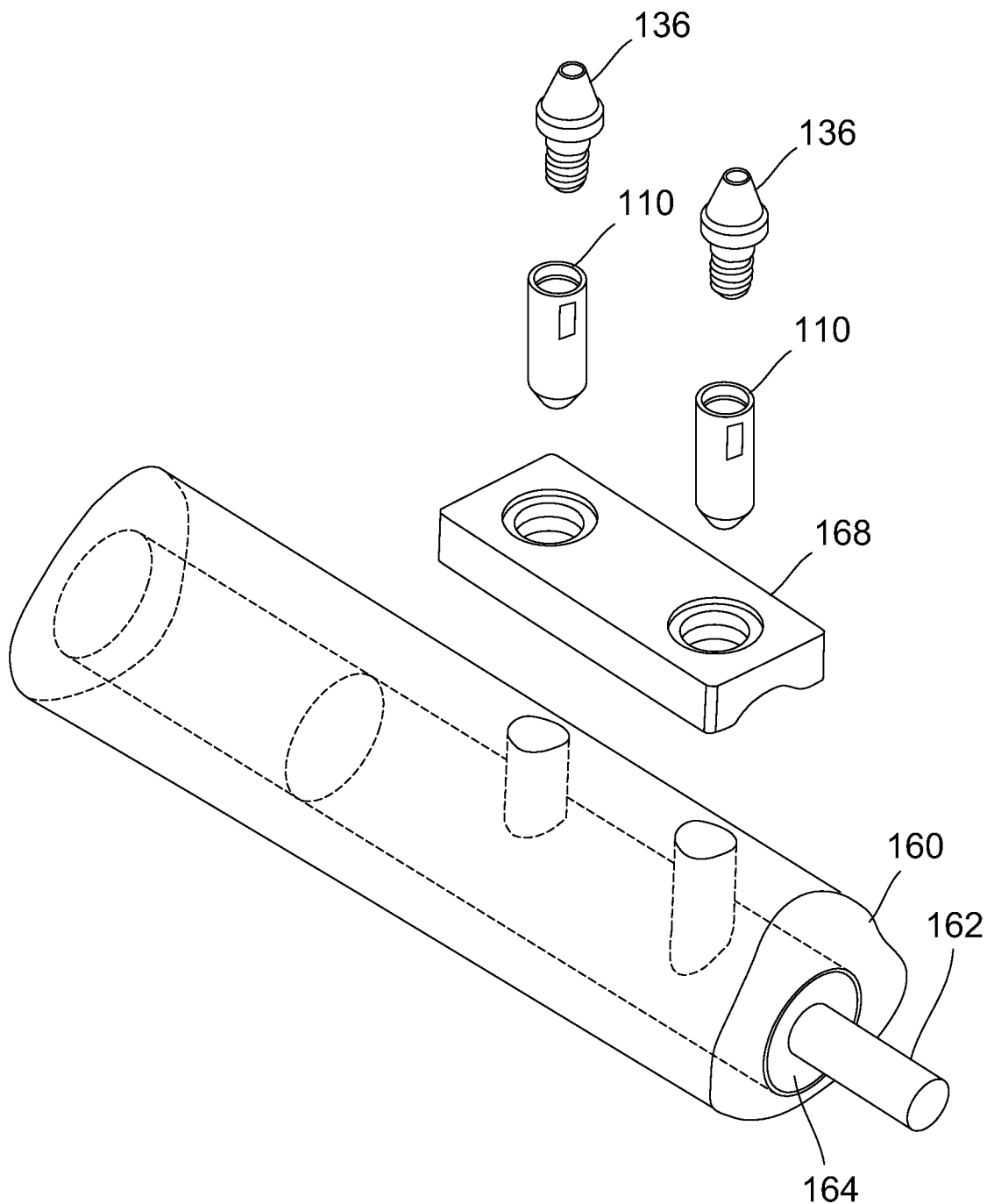
FIG. 26 illustrates the use of a fastening implant and an embedding implant to secure a supporting implant.
Figure 27:
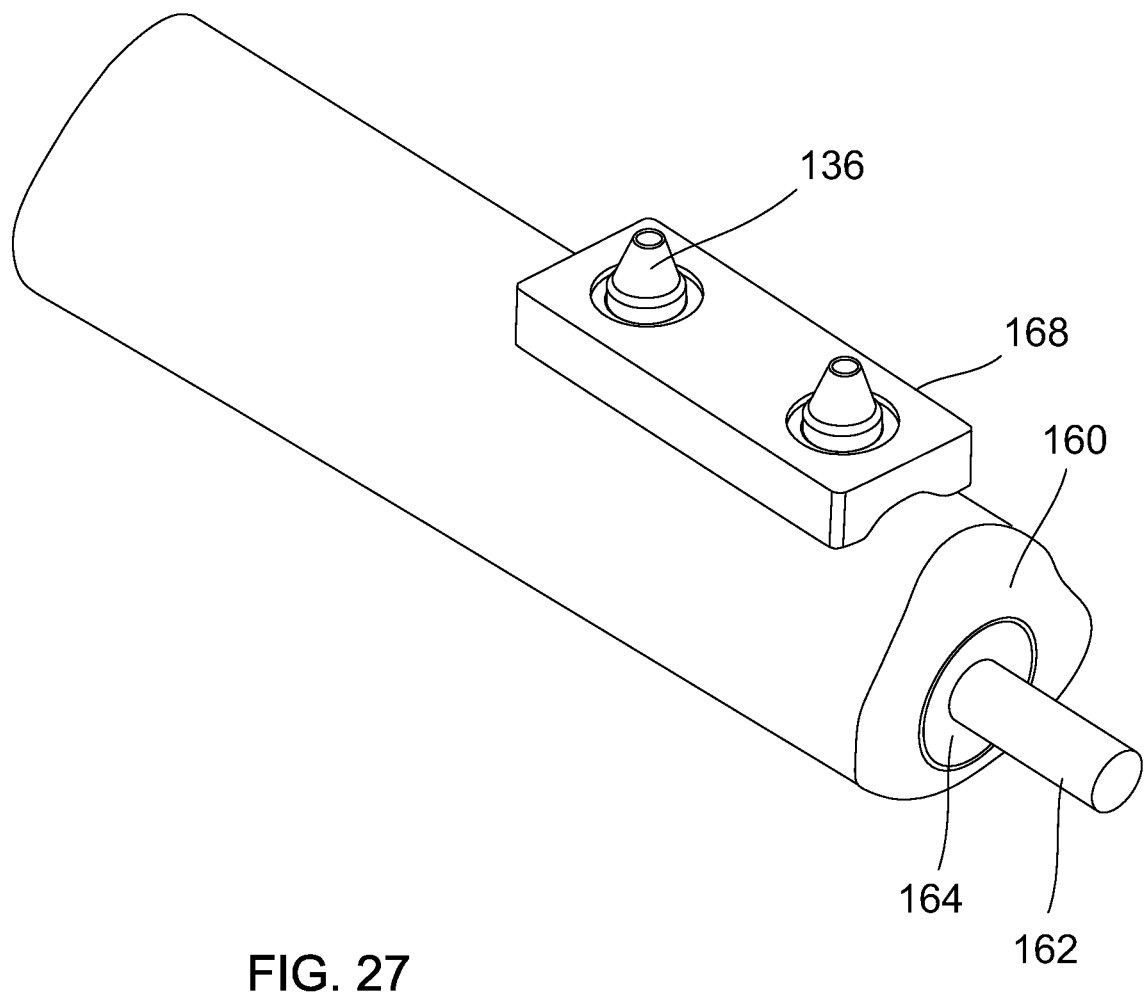
FIG. 27 illustrates the assembled configuration of FIG. 26.

In an embodiment shown in FIGS. 26-27, implant 162 may be coated in bondable material 164 and implanted in body tissue 160. For example, a metal rod coated with bone cement may be placed in the intramedullary canal of a bone. In an embodiment, support 168 may placed in a location to facilitate stabilization. Support 168 and/or washer 146 may be referred to as a supporting implant. One or more holes may be formed in body tissue 160 and up to or into bondable material 164 to coincide with the holes in support 168. Embedding fastener 110 may be placed through the holes in body tissue 160 and secured to and/or bonded to bondable material 164 as discussed herein. Then, one or more of fastener 136 are secured to and/or bonded to the one or more embedding fastener 110, thereby securing support 168 relative to body tissue 160.

Figure 28:
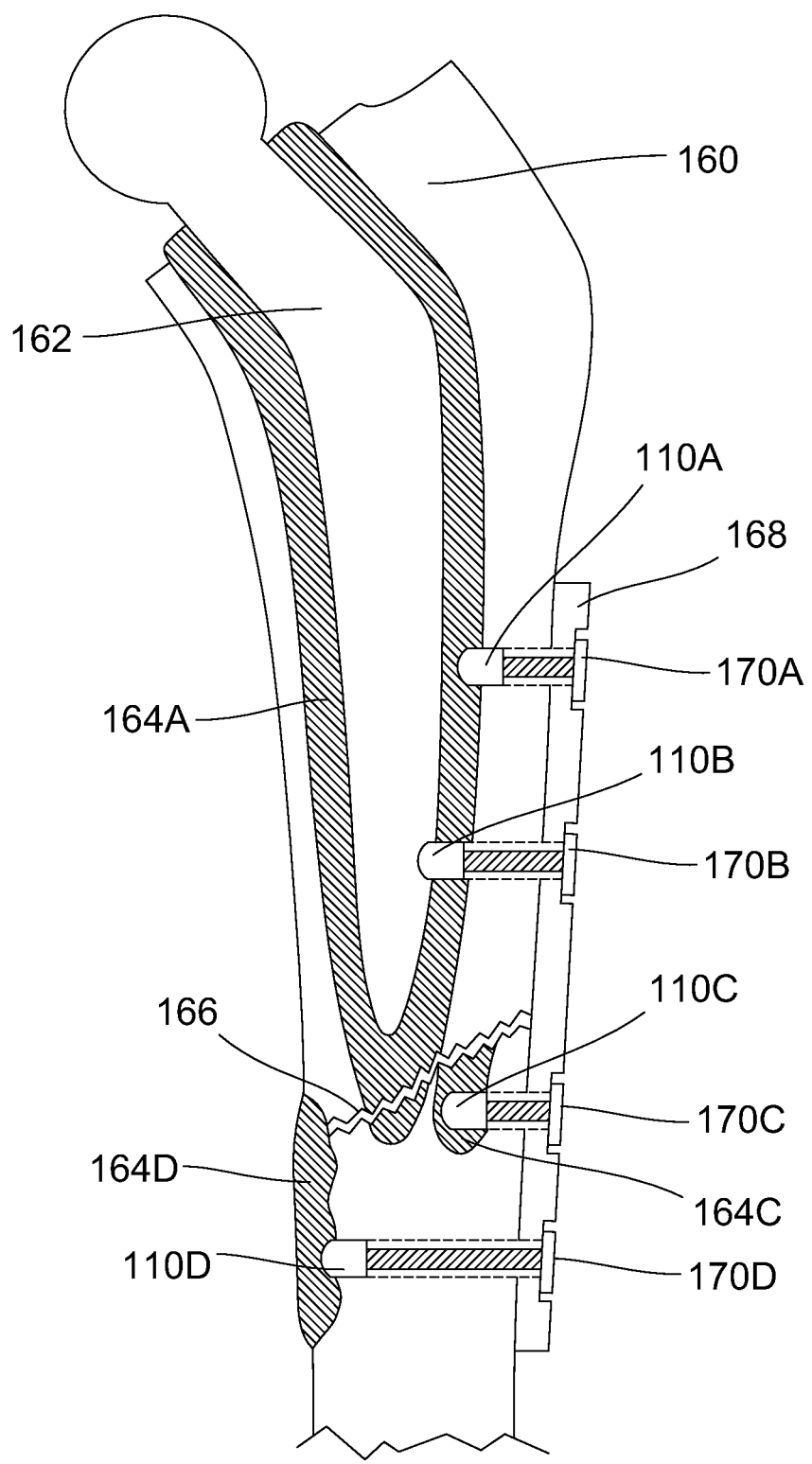
FIG. 28 illustrates devices and methods related to utilization of implants and bondable materials.

Referring to FIG. 28, implant 162 may be installed in a body tissue 160 with bondable material 164, for example bone cement. Bondable material 164 may be any material described herein or known in the art. Implant 162 may require stabilization because implant 162 has become loose and/or requires stabilization due to tissue defect 166, for example a periprosthetic fracture. Tissue defect 166 may include, but is not limited to, damaged, deformed, and/or diseased bone, muscle, ligament, tendon, cartilage, capsule, organ, skin, nerve, vessel, or other body part. For example, a femur may be fractured or contain osteoporosis. Support 168 is fixed to body tissue 160 with fastener 170 to provide stabilization. Support 168 may be an internal bone plate, an external bone plate, a spinal plate, a wedge, a cushion, a pad, or other biocompatible support used for stabilization of tissue and/or implants. Fastener 170 may be any fastener described herein or any other biocompatible fastener known in the art.

In an embodiment, implant 162 has been previously installed and requires stabilization. One or more holes are formed through body tissue 160 and up to or into bondable material 164. Embedding fastener 110 is inserted through a hole and bonded to bondable material 164 by utilizing instrument 100 described above. Fastener 170 engages embedding fastener 110 to secure support 168 to body tissue 160. The head of fastener 170 may be deformed and/or bonded to support 168 to reduce loosening of fastener 170.

Embedding fastener 110 can also be bonded to bondable material 164C/D that is within or on the surface of body tissue 160. For example, bondable material may have been used to repair tissue defect 166. Bondable material 164 may be within or on the surface of body tissue 160. A hole is formed up to or into the bondable material 164. Embedding fastener 110 is bonded into bondable material 164. Fastener 170 passes through support 168 and into engagement with embedding fastener 110 to secure support 168 relative to body tissue 160.

In another embodiment, embedding fastener 110A/B can be bonded to and/or into implant 162. The procedure is performed as described above, except the embedding fastener 110 may be bonded directly to implant 162.

In another embodiment, bondable material 164 may asymmetrically cover all or a portion of implant 162. The thickness of bondable material 164 could vary in the radial direction or along the length of implant 162. An asymmetrically coated implant 162 may provide additional purchase for fastener 136 or indication of orientation or position of implant 162.

In an additional embodiment, indirect visualization may be used to identify and/or change the orientation or position of implant 162 or fastener 136. Examples of indirect visualization may include endoscopic guidance, computer assisted navigation, magnetic resonance imaging (MRI), CT scan, ultrasound, fluoroscopy, X-ray, or other visualization technique disclosed in any of the references incorporated herein. Asymmetric coating, radiopaque markers, or other features identifiable with indirect visualization may be used to identify and/or adjust orientation or position. Indirect visualization may also be used to align fastener 136 with holes in implant 162 or bondable material 164. The holes may be predrilled in implant 162 or bondable material 164 or may be drilled after installation of 162. Indirect visualization may be used to create a hole or holes in tissue to align with holes in implant 162 or bondable material 164.

For example, an intramedullary rod could be asymmetrically coated with PEEK. The intramedullary rod could have predrilled holes in the PEEK coating. After the rod is installed in the intramedullary canal of the tibia, the orientation of the rod may be determined using indirect visualization to locate the area with a thicker coating. The orientation of the rod may be adjusted to the appropriate location for holes to be made through the tissue.

Figure 29:
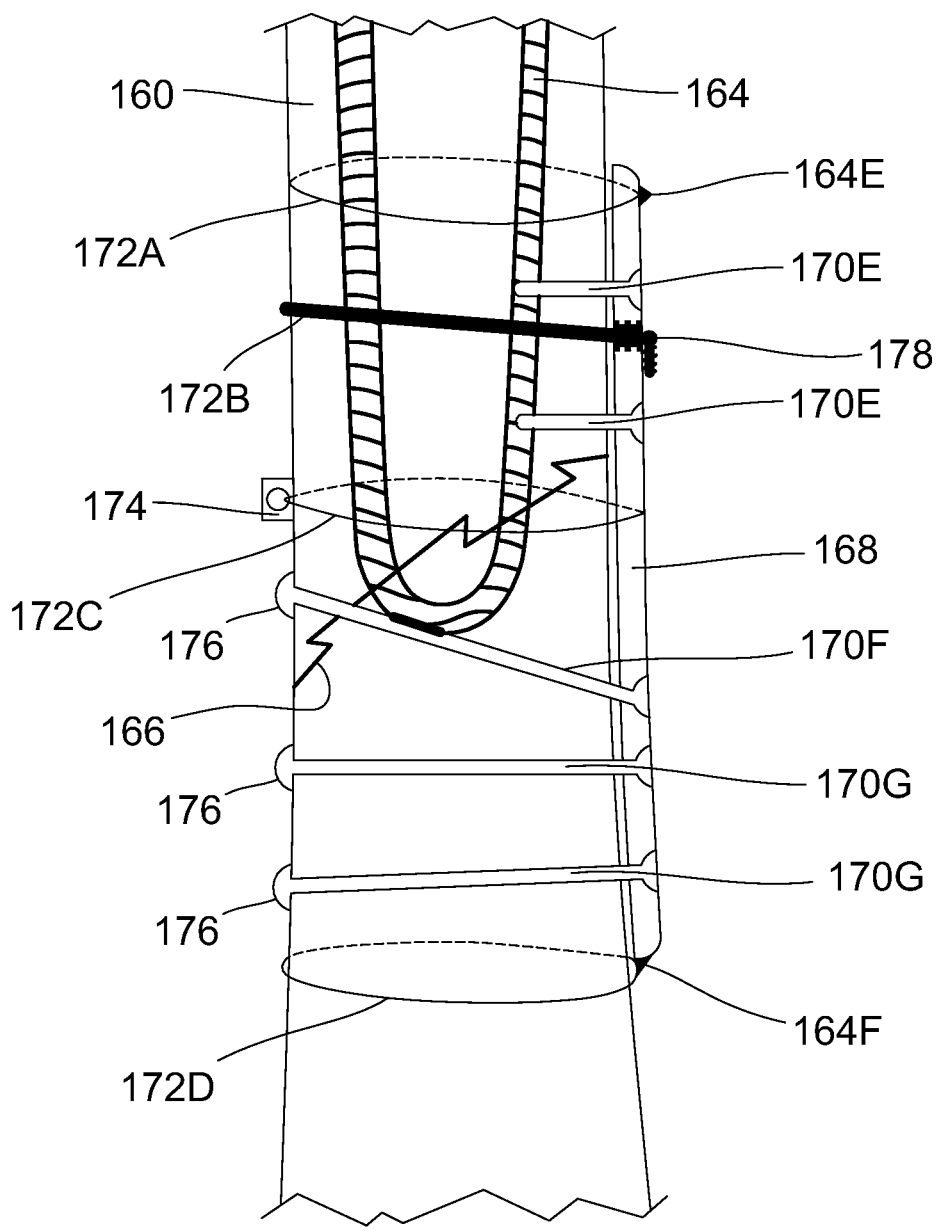
FIG. 29 illustrates alternatives for the devices and methods of FIG. 28.

With further reference to FIG. 28-29, various types of fastening devices are used to position support 168 along body tissue 160. Alternatively, support 168 may be positioned upon the surface of the skin, or at any point between the tissue surface and the skin, according to the requirements of the surgical procedure. Further, support 168 may be placed within the bone, for example in an intramedullary canal.

Referring to FIG. 29, fastener 170 may be used in intramedullary, percutaneous, and/or retrograde approaches. Fastener 170 may be bonded to bondable material 164, or a surface of implant 162. The head of fastener 170 may be provided, or may be formed using vibratory energy. A head may also be formed on the distal end of fastener 170. Fasteners 170E are shown to be bonded into the bondable material 164. Fastener 170F is shown to be bonded at the distal end and/or to bondable material 164 within the body tissue and is placed through tissue defect 166. Fasteners 170G are shown passing directly through body tissue 160, which may be fastener 170T and sleeve 171T in FIGS. 52-53 and as described below. Additional embodiments of fastener 170 are disclosed in U.S. patent application Ser. No. 12/202,210 entitled "Methods and Devices for Utilizing Thermal Energy to Bond, Stake and/or Remove Implants", which is incorporated by reference herein.

Additionally, cerclage wire 172 may be employed as known in the art, to provide further stabilization, in combination with fastener 170. For example, cerclage wire 172A may be bonded to support 168. Bondable material 164E could be used to affix cerclage wire 172A to support 168. In another example, cerclage wire 172B may be tied around support 168. Also, cerclage wire 172C may be fastened using a mechanical or bonded crimp 174. In additional example, cerclage wire 172D may fastened to the side of support 168 or between support 168 and body tissue 160.

Figure 30:
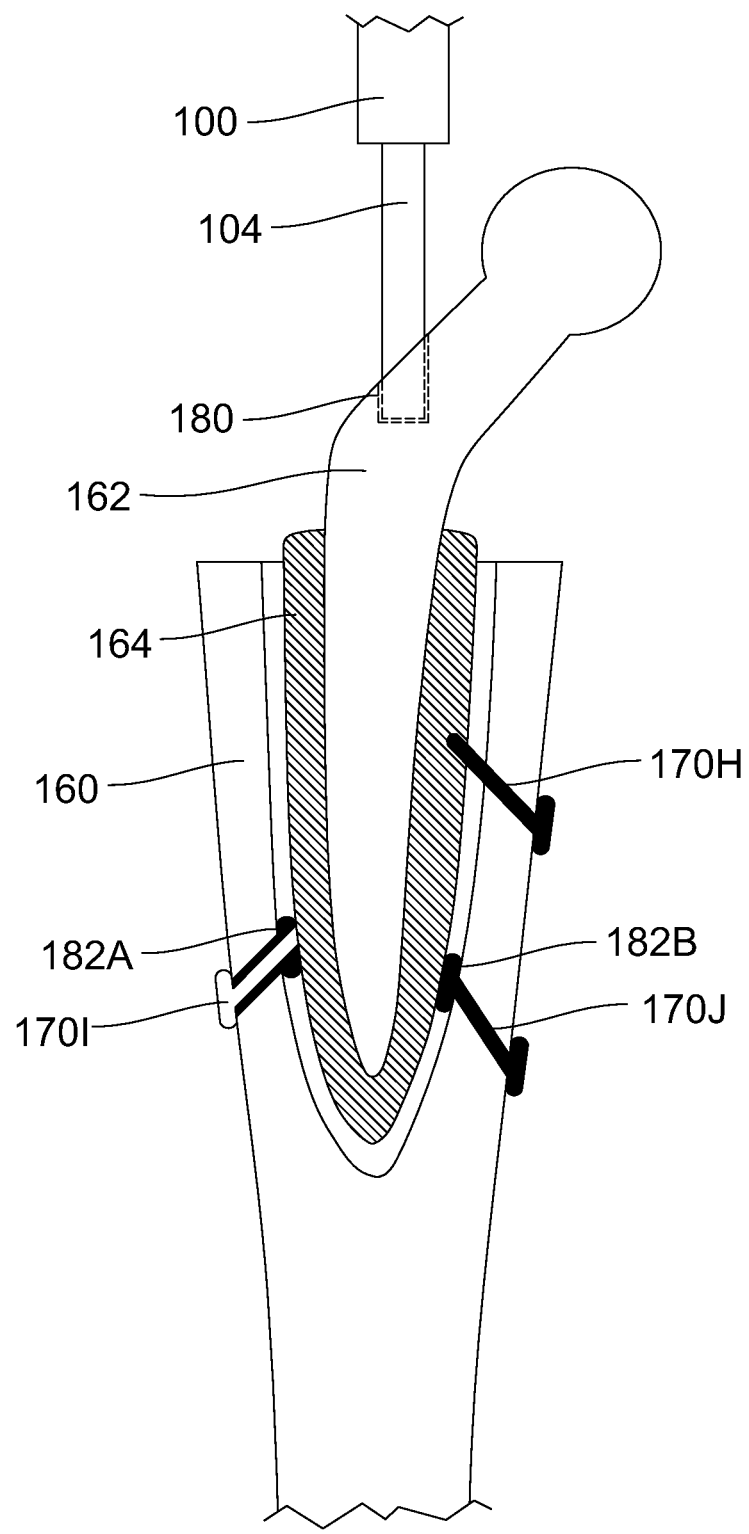
FIG. 30 illustrates alternatives for the devices and methods of FIG. 29 and illustrates a method of connecting an instrument to an implant.

Referring to FIG. 30, end effector 104 of instrument 100 may be connected into implant 162 at recess 180. This connection may be threaded, magnetic, friction, hex, ball and socket, linkage, adhesive, and other connections suitable for transferring vibratory energy as disclosed herein or known in the art. Also, other vibratory energy devices as disclosed herein or known in the art may be utilized.

FIG. 30 also shows additional methods of stabilizing a loose implant and/or facilitating the solidification and/or polymerization of bondable material 164. For example, fastener 170H may be a metal and/or polymer fastener, which may be affixed to the bondable material 164 and/or implant 162 to stabilize implant 162. In another example, fastener 170I may be metal coated with bondable material. Upon the application of vibratory energy and/or heat, distal end 182A deforms thereby stabilizing the gap between implant 162 and body tissue 160. In an additional example, fastener 170J may be made of bondable material. Upon the application of vibratory energy and/or heat, distal end 182B deforms, thereby stabilizing the gap between implant 162 and body tissue 160.

Figure 31:
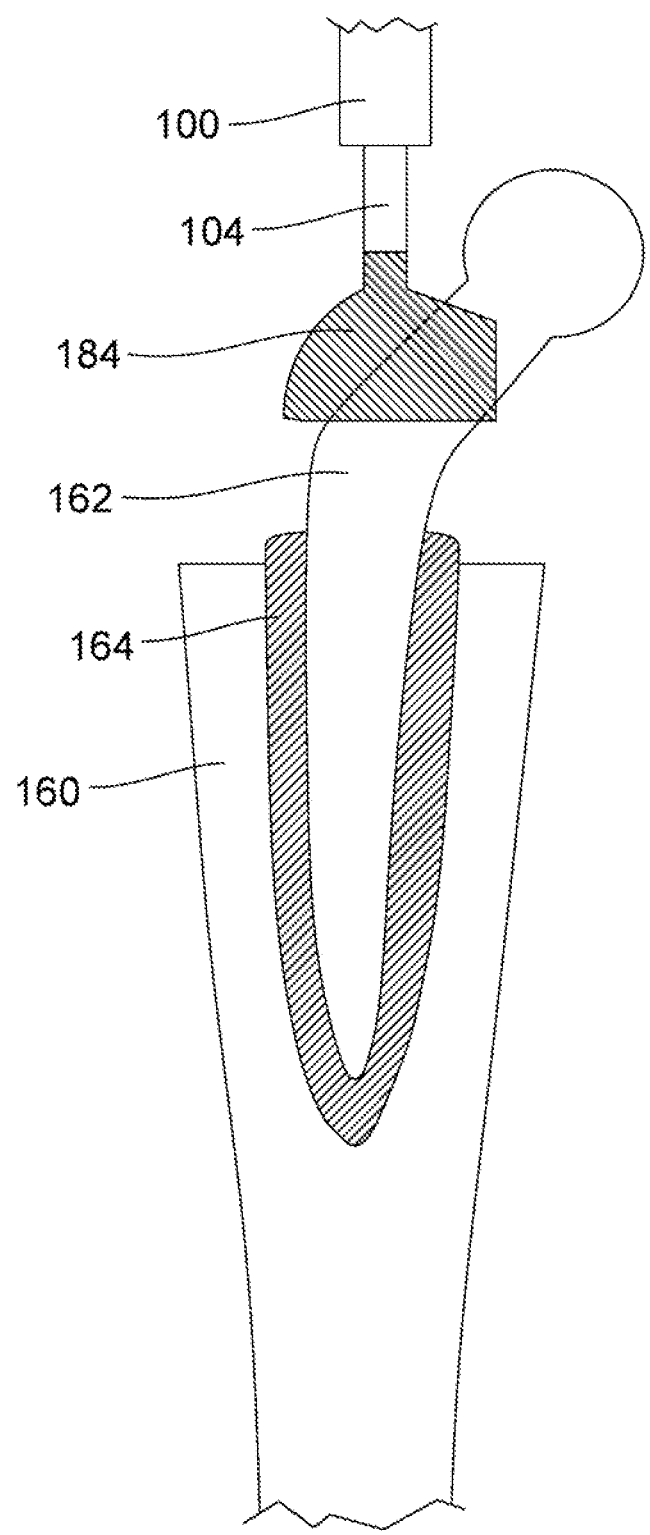
FIG. 31 illustrates an alternative method of connecting an instrument to an implant.

Referring to FIG. 31, end effector 104 of instrument 100 may be connected into implant 162 with coupler 184 to stabilize previously hardened and/or polymerized bondable material 164 or to facilitate solidification and/or polymerization of bondable material 164. This connection may be threaded, magnetic, friction, hex, ball and socket, linkage, adhesive, and other connections suitable for transferring vibratory energy as disclosed herein or known in the art. Also, other vibratory energy devices disclosed herein or known in the art may be utilized.

Figure 32:
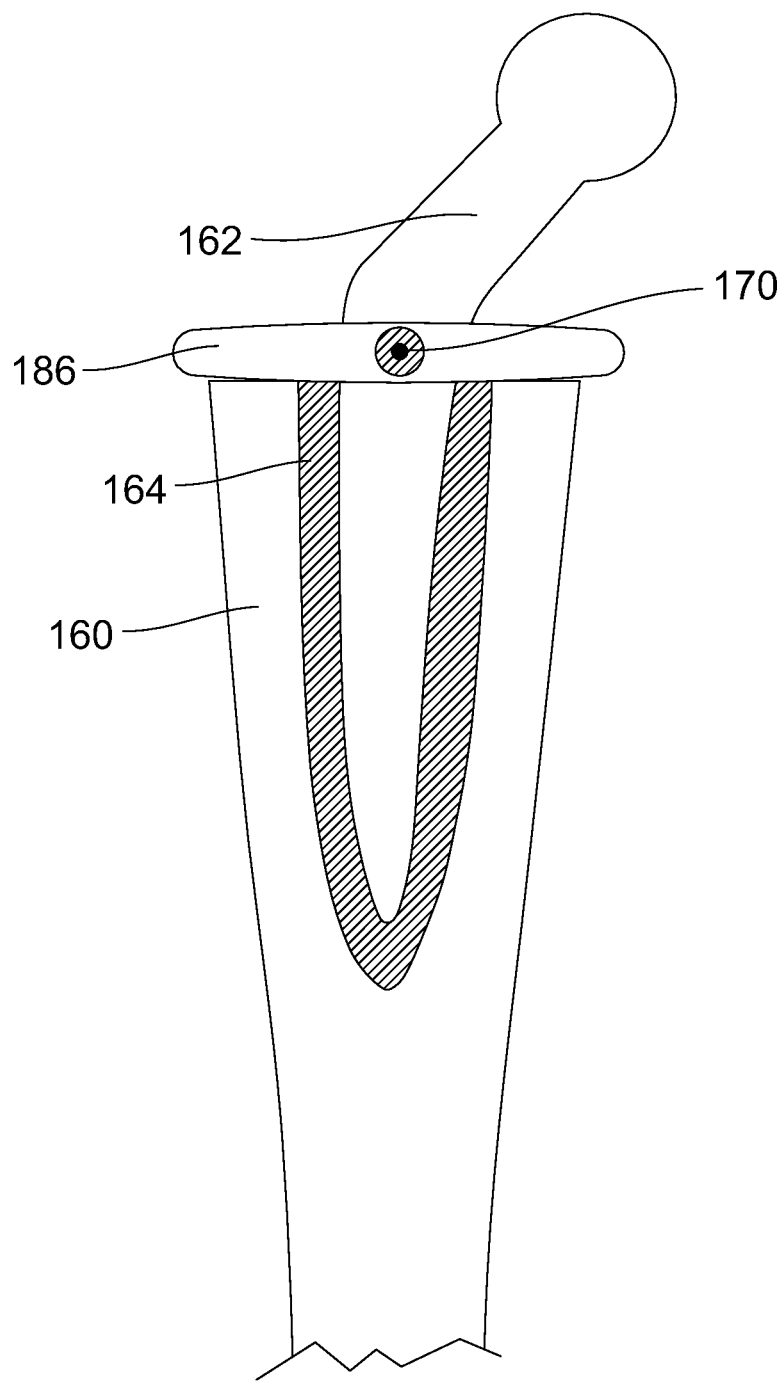
FIG. 32 illustrates the affixing an attachment to an implant.

Referring to FIG. 32, attachment 186 may be attached and/or bonded to implant 162. Attachment 186 may be made from any material described herein (i.e. collagen, graft, or growth promoter) or any other material known in the art, preferably to promote healing and/or contain bondable material 164. For example, vibratory energy may be used to bond attachment 186 to implant 162. In another example, fastener 170 may secure attachment 186 to implant 162. In an additional example, vibratory energy may be used to bond fastener 170 to attachment 186.

Figure 33:
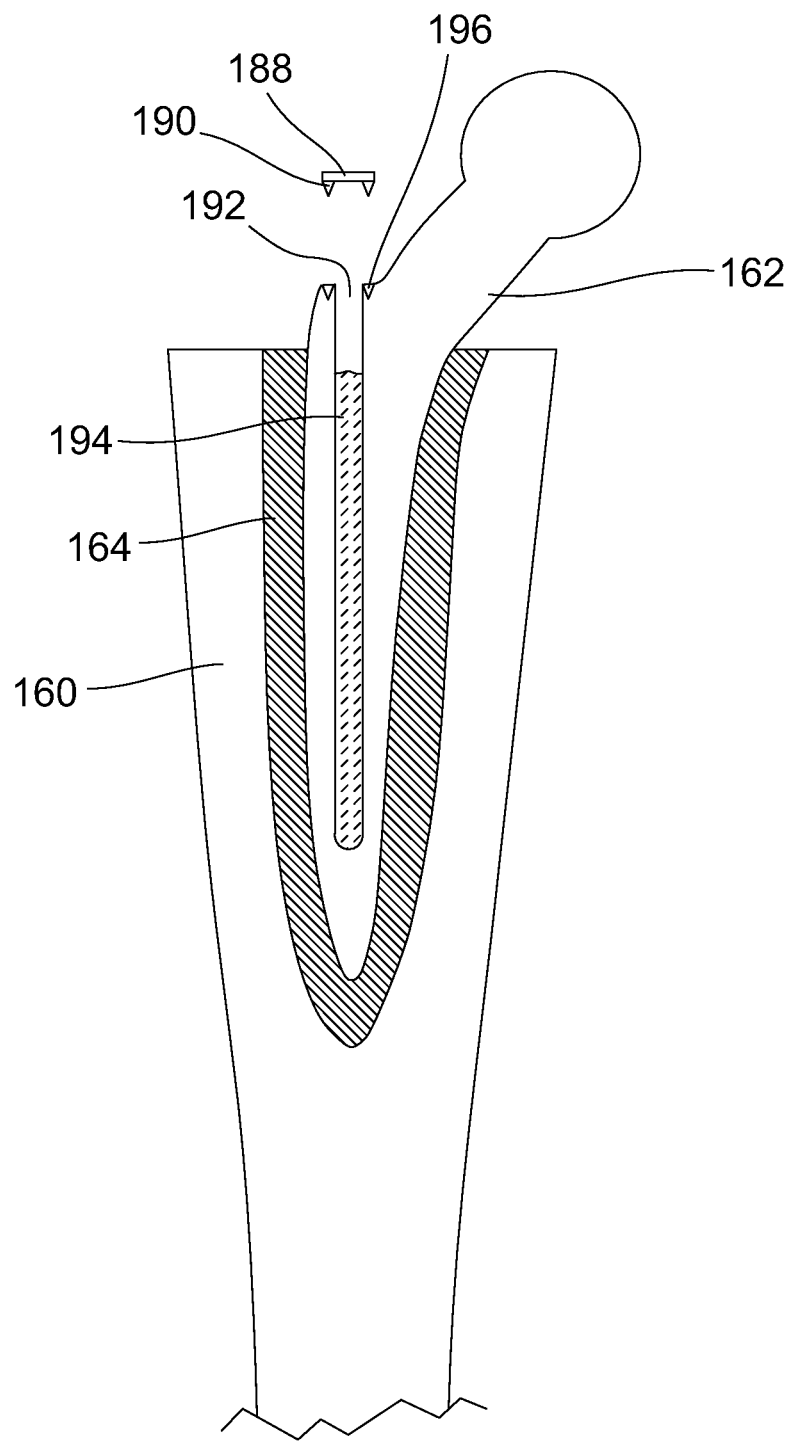
FIG. 33 illustrates the use of a reservoir.
Figure 34:
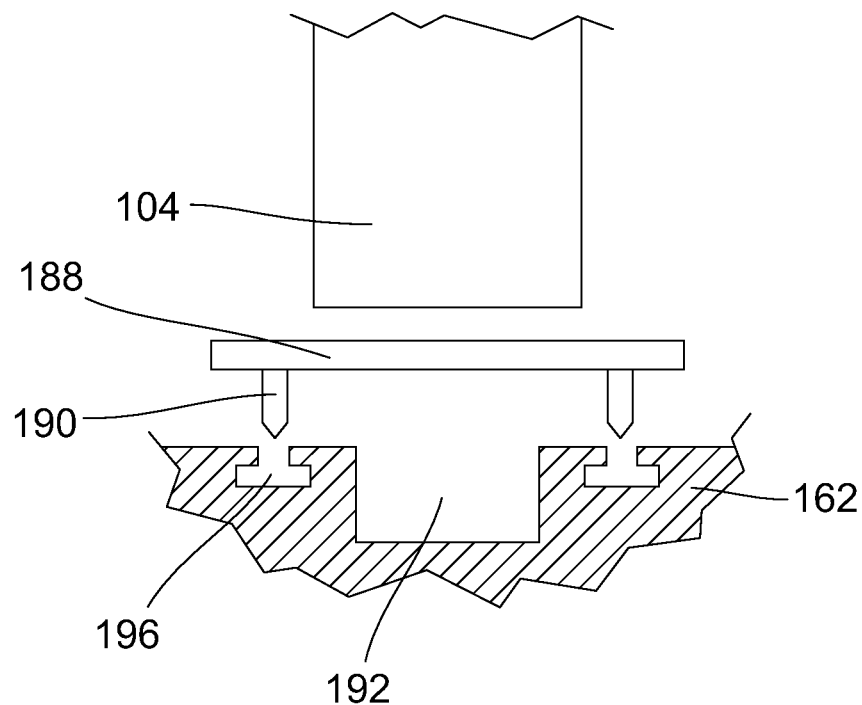
FIG. 34 illustrates an alternative configuration of FIG. 33.

Referring to FIGS. 33-34, implant 162 may be manufactured with reservoir 192 or reservoir 192 may be formed during or after implantation. Additionally, therapeutic substance 194 may be incorporated in reservoir 192 of implant 162, impregnated in implant 162, or coated on or in implant 162. As shown in FIG. 33, reservoir 192 may be located in implant 162. Alternatively, reservoir 194 may be formed in body tissue 160, as shown in FIG. 34. Cap 188 may be made of bondable material. Additionally, cap 188 may be attached and/or bonded to enclose reservoir 192. Implant 162, cap 188, and/or body tissue 160 may contain attachment feature 190 and/or attachment recess 196 to facilitate mechanical attachment and/or bonding with end effector 104. Additionally, implant 162, cap 188, and/or bondable material 164 may be porous to facilitate the delivery of therapeutic substance 194.

Figure 35:
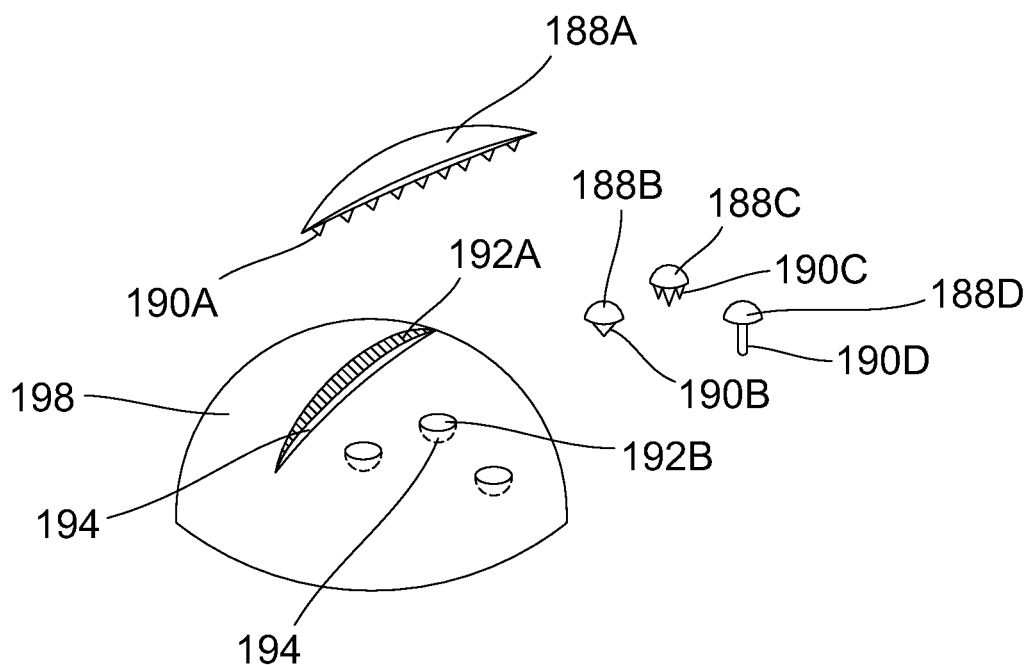
FIG. 35 illustrates alternative types of reservoirs in an alternative type of implant.

Referring to FIG. 35, therapeutic substance 194 may be contained in implant 198, for example drugs or antibiotics contained in an acetabular cup. Implant 198 may be manufactured with reservoir 192A and/or reservoir 192B or the reservoirs may be formed during implantation. Any combination of one or more reservoir 192A and/or reservoir 192 may be used. Cap 188 may be coated with bondable material. Additionally, any of caps 188A-D may be attached and/or bonded to enclose reservoir 192A or 192B, which may provide the potential benefit of multiple release times for therapeutic substance 194 Caps 188A-D may contain attachment features 190A-D to facilitate mechanical attachment and/or bonding. Additionally, implant 198 and/or any of caps 188A-D may be porous to facilitate the delivery of therapeutic substance 194.

Figure 36:
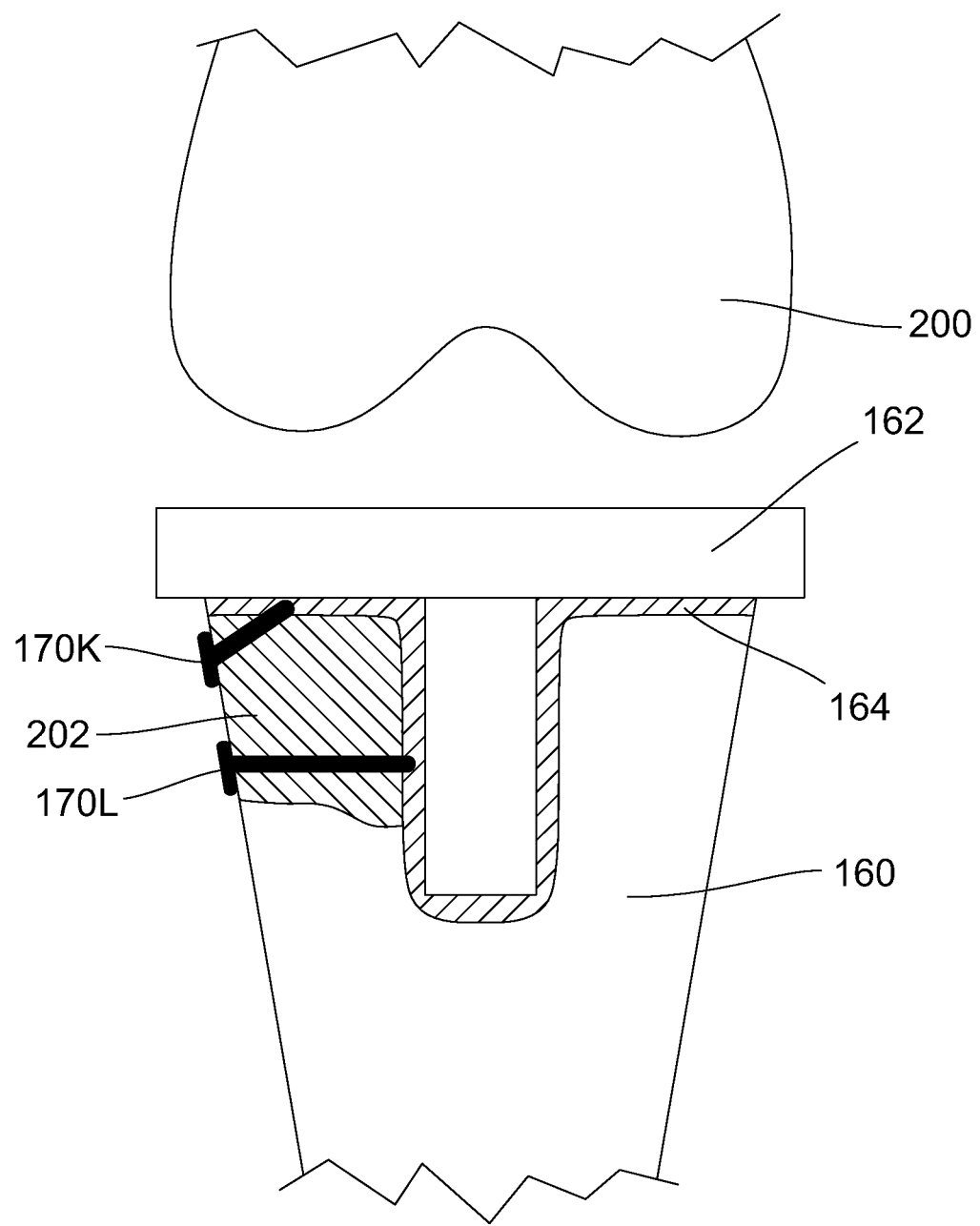
FIG. 36 illustrates an additional alternative type of implant.

Referring to FIG. 36, fastener 170 may be used to stabilize implant 162, for example a tibial component of a total knee arthroplasty (TKA). In an embodiment, fastener 170K may be bonded to bondable material 164 on the underside of the implant or bonded directly to implant 164. In another embodiment, fastener 170L may be bonded to the portion of implant 162 that is within body tissue 160. In an additional embodiment, fastener 170 may be used to secure tissue graft 202 to implant 162 and/or body tissue 160. For example, tissue graft 202 may be an allograft. Any embodiment of fastener 170 that has been described herein or known in the art may be used.

Figure 37:
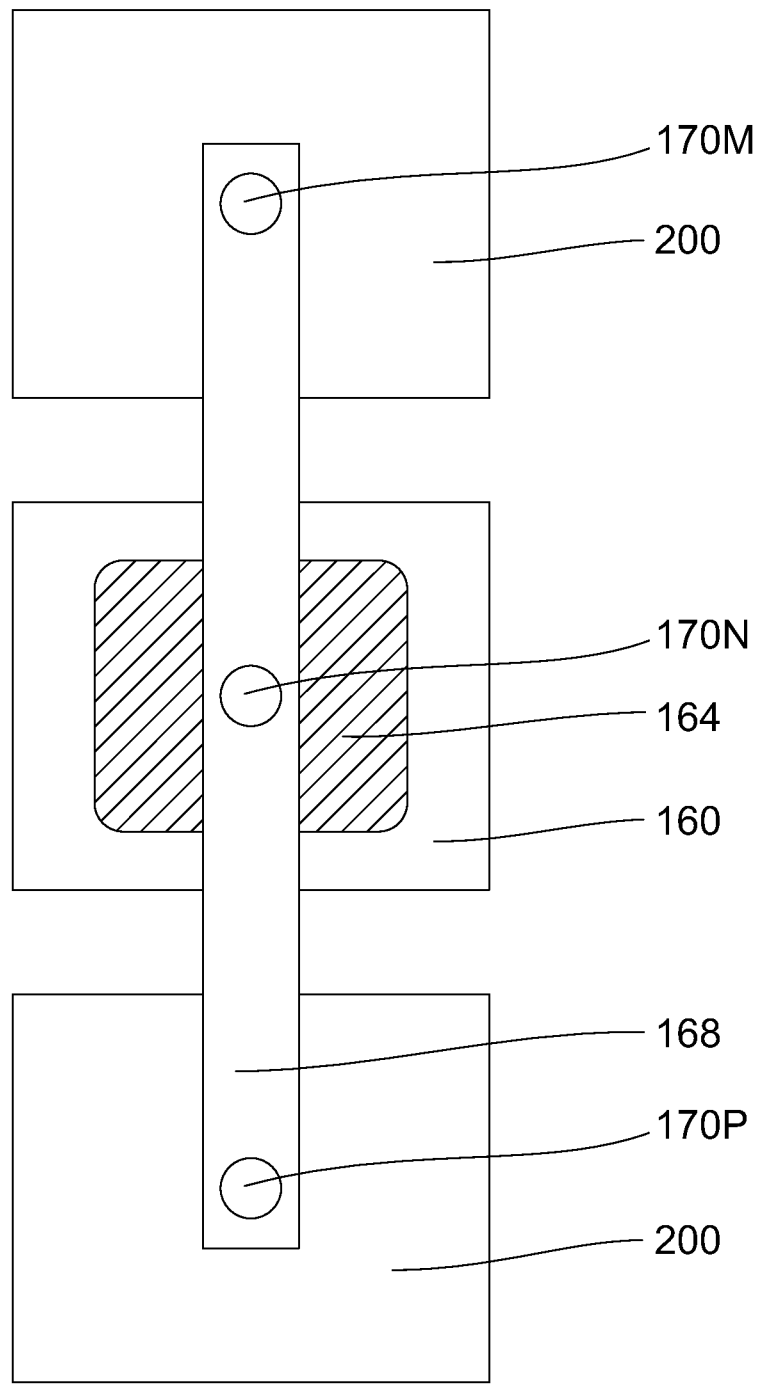
FIG. 37 illustrates fixation to previously implanted bondable material.
Figure 38:
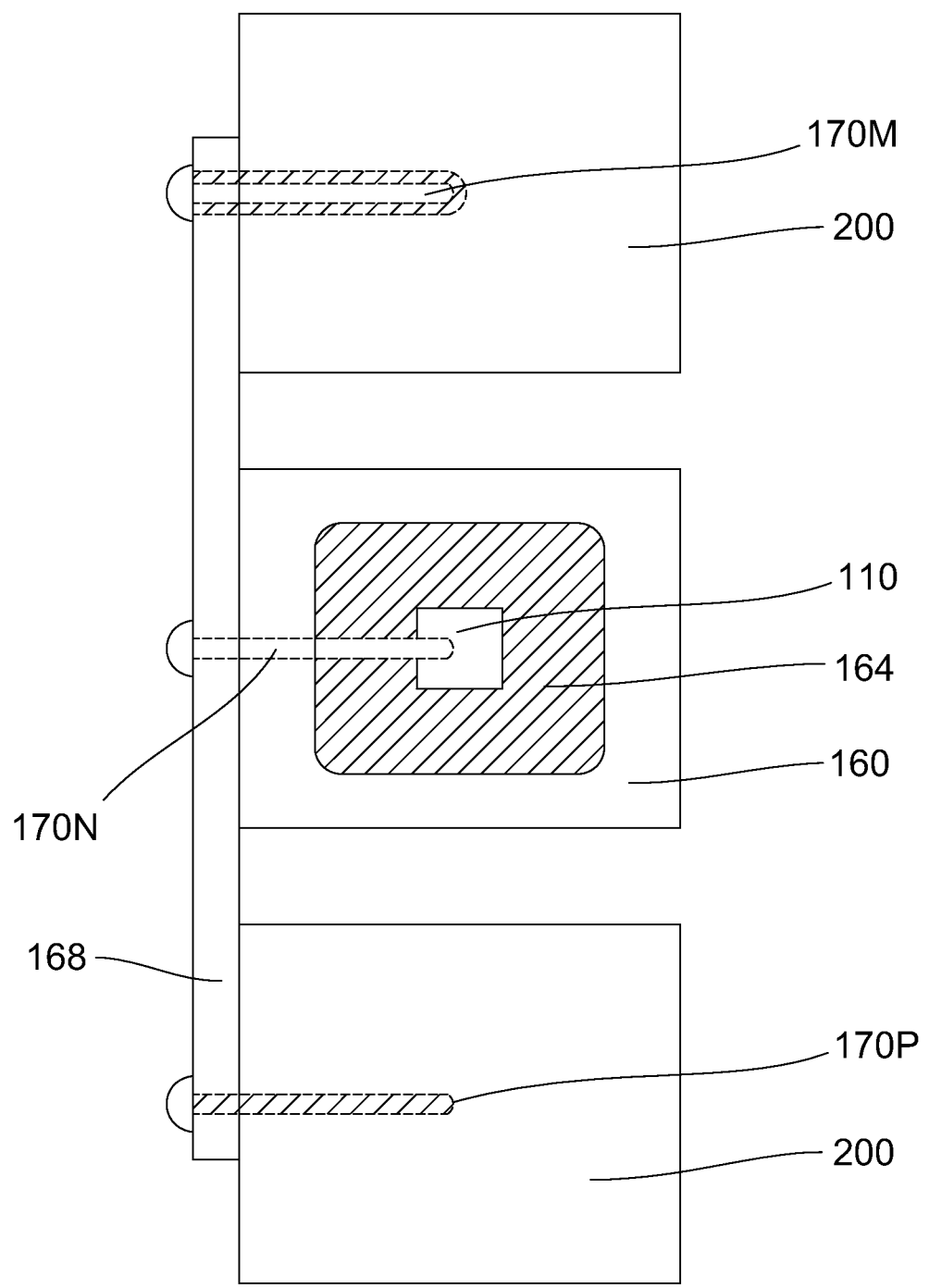
FIG. 38 illustrates an alternative view of FIG. 37.
Figure 39:
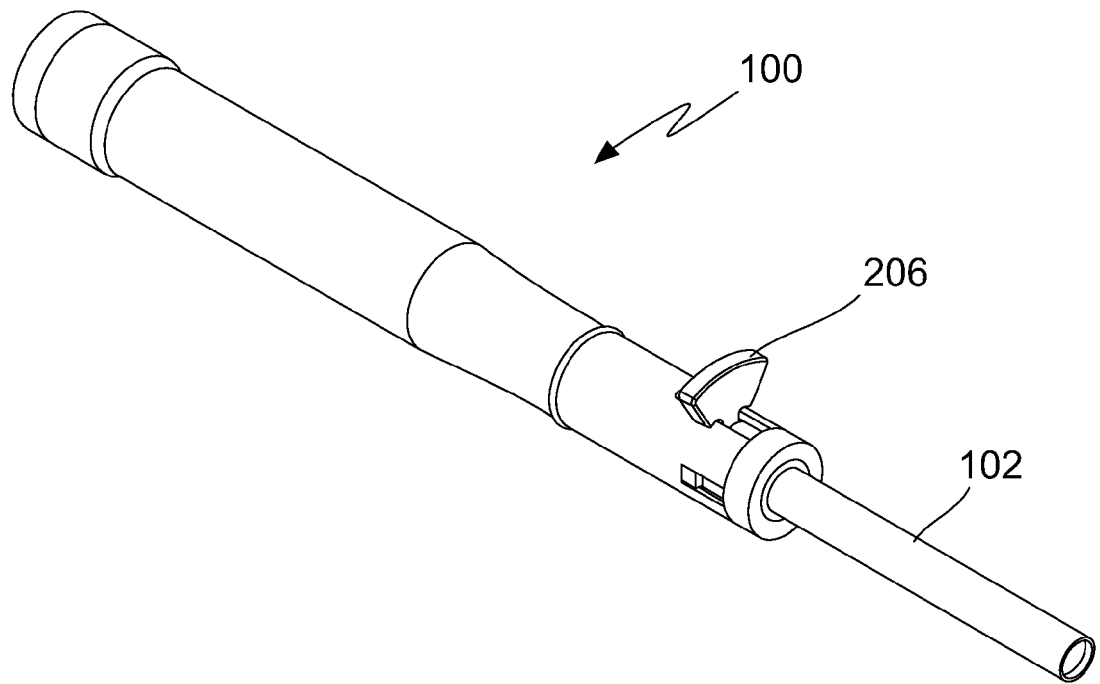
FIG. 39 illustrates an alternative configuration of the instrument of FIG. 1.
Figure 40:
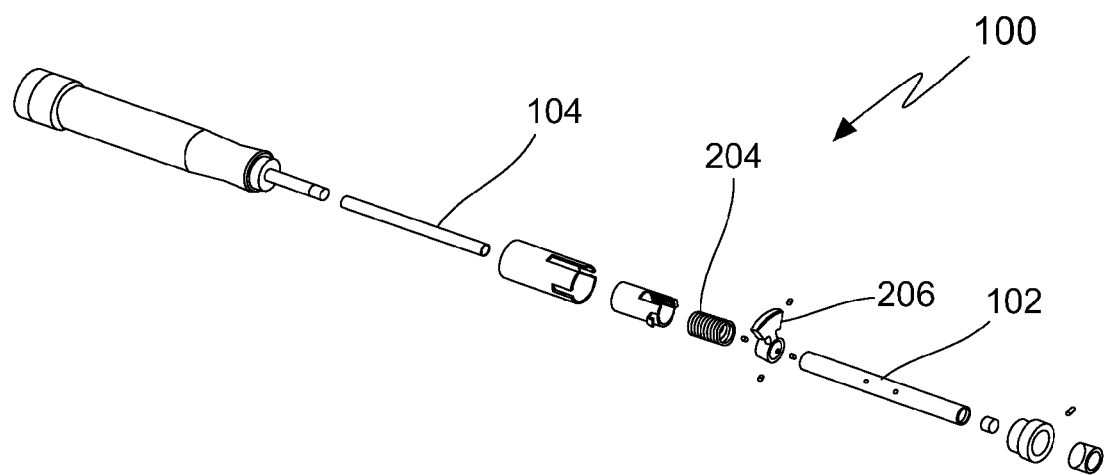
FIG. 40 illustrates an exploded view of the instrument of FIG. 39.
Figure 41:
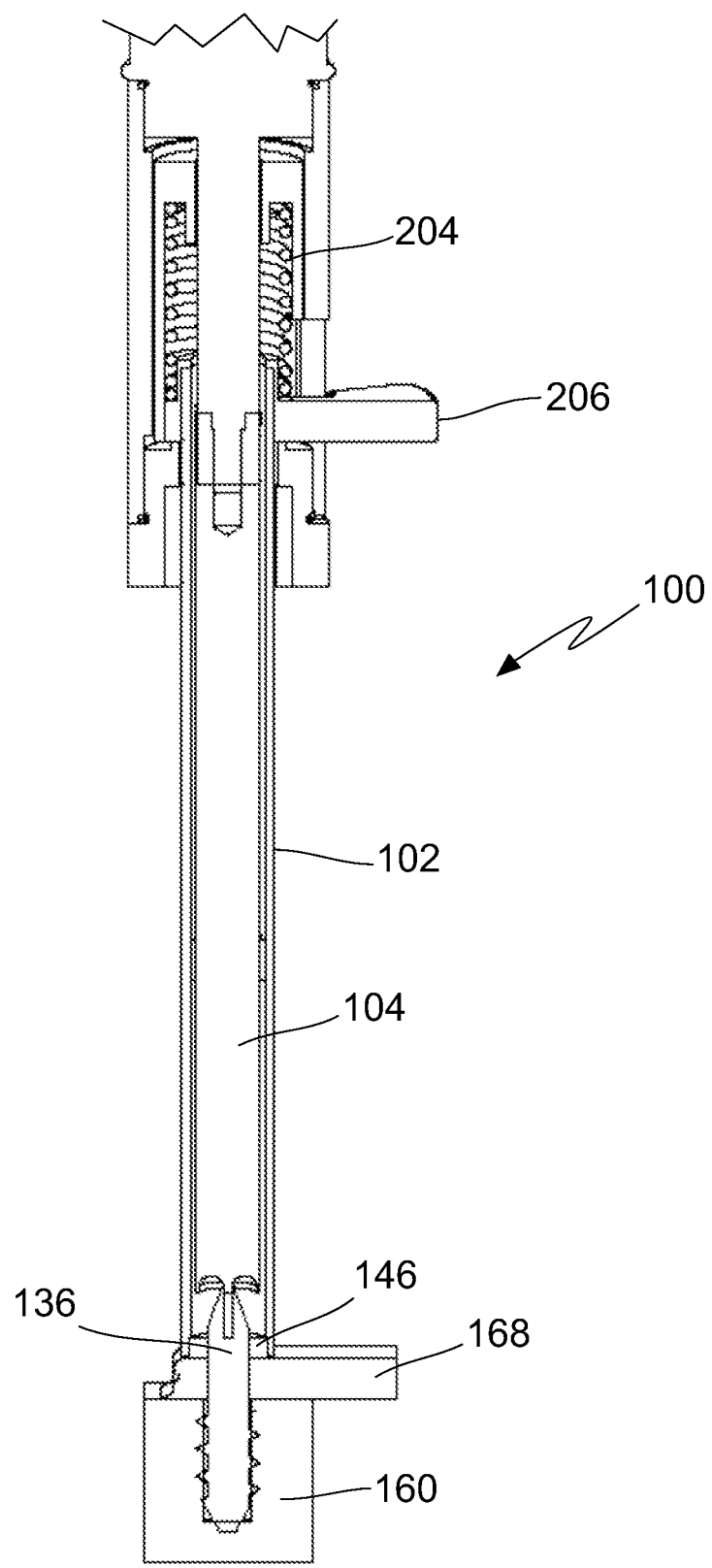
FIG. 41 illustrates a method of utilization for the instrument of FIG. 39.

Referring to FIGS. 37-38, bondable material 164 may be utilized to stabilize body tissue 160. For example, bone cement in previously performed kyphoplasty may become loose and require additional stabilization. In this example, the fasteners may utilize the previously implanted bone cement to stabilize the spine instead of removing and reapplying bone cement. In an embodiment, body tissue 160 has been previously implanted with bondable material 164. Fastener 170N is passed through support 168 and bonded to bondable material 164. As shown in FIG. 37, one or more fastener 170 is passed through support 168 and secured and/or bonded to surrounding tissue 200. Fasteners 170M, 170N, and 170P may be any embodiment disclosed herein or known in the art. Additionally, fasteners 170M, 170N, and 170P may be used with embedding fastener 110 as described above. Also in these embodiments, vibratory energy may be used to stabilize previously hardened and/or polymerized bondable material or to facilitate the solidification and/or polymerization of bondable material.

Referring to FIGS. 39-41 and 50-51, an additional embodiment of instrument 100 includes guide sheath 102, spring 204, and/or force regulator 206. In an embodiment in FIG. 41, guide sheath 102 may align washer 146 when the tip of end effector 104 is placed in contact with fastener 136. As fastener 138 is staked and the tip of fastener 136 is shaped with the application of vibratory energy, such as ultrasonic energy, guide sheath 102 may allow end effector 104 to advance while applying force to washer 146, support 168, body tissue 160, and/or bondable material 164 (not shown in FIG. 41). In a further embodiment in FIG. 41, guide sheath 102 may hold, guide, align, and/or deliver washer 146, fastener 136, or other fasteners referenced herein or known in the art. In an additional embodiment, regulating sheath 206 may have a spring 204, for example any spring, cushion, or other material or device known in the art for spring/damping applications. Additionally, instrument 100 may have regulating tab 206 for manually applying and/or regulating the movement of guide sheath 102. Although the embodiment in FIG. 41 may be used under a limitless number of configurations and settings, Table 2 is being set forth with operative examples:

TABLE 2

Polycarbonate Fastener Bonding

| Test Sample Number | Power (watts) | Energy Application Time (sec) | Force Applied to Break (lbs.) | Deformation Depth (inches) |
| --- | --- | --- | --- | --- |
| 1 | 30 | 1.69 | 93.2 | 0.115 |
| 2 | 28 | 1.68 | 86.4 | 0.110 |
| 3 | 31 | 1.78 | 98.2 | 0.111 |
| 4 | 27 | 1.80 | 91.3 | 0.108 |
| 5 | 31 | 1.69 | 109.2 | 0.109 |

Instrument: Handpiece P05 with tuning of 39,000-45,000 Hz
System Settings: 39,500 Hz, 50 W, 1.0 sec weld time In additional embodiments, frequency may preferably be between 20 to 80 khz, power may preferably be between 5 to 200 watts, and energy application time may be preferably between from 0.1 to 5 seconds.

In an embodiment, a sensor may be included in instrument 100. For example, a force, pressure, or temperature sensor may be used to measure bonding and/or staking. In another example, a visual and/or audio indicator may be operatively connected to the sensor, which may be used to indicate a proper bond/stake. In another embodiment, a visual and/or audio indicator may be connected to instrument 100 or the energy generator, which may be used to illustrate and/or teach proper technique during bonding and/or surgery. In another example, the visual and/or audio indicator may indicate completion of a proper bond/stake, over/under application of force, or expiration of desired energy application time.

In another embodiment, a vacuum may be operatively connected to 100. For example, the vacuum may be communicatively connected between the guide sheath 102 and end effector 104, which may be used for the removal of debris from instrument 100.

Figure 42:
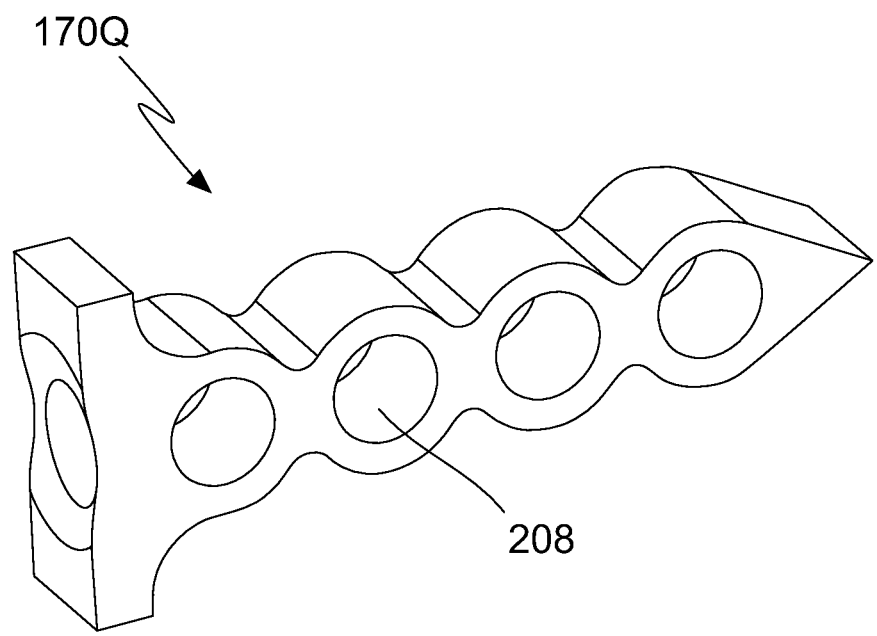
FIG. 42 illustrates an alternative configuration of a fastening implant.
Figure 43:
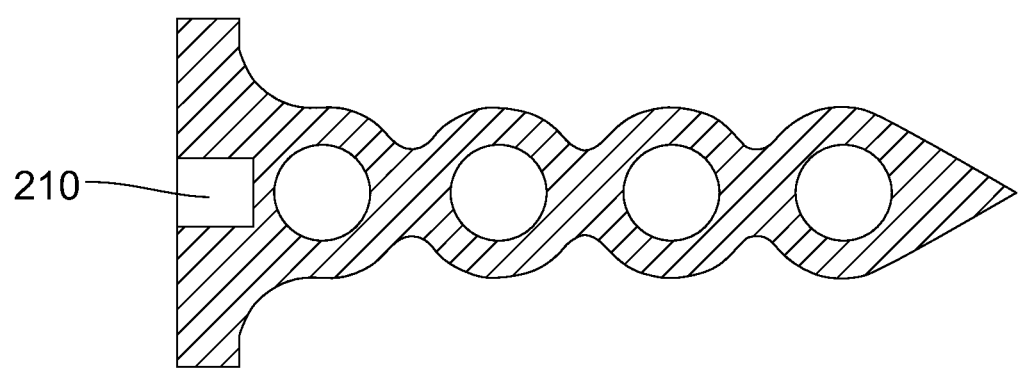
FIG. 43 illustrates an alternative view of FIG. 42.

Referring to FIGS. 42-43, an additional embodiment of fastener 170 may include one or more feature 208. Feature 208 may increase or decrease the transfer of energy across fastener 170. Feature 208 may pass into the surface or through fastener 170. Feature 208 may be on any surface or surfaces of fastener 170 and/or contain therapeutic substances. Fastener 170 may include effector interface 210, preferably for engagement with end effector 104.

Figure 44:
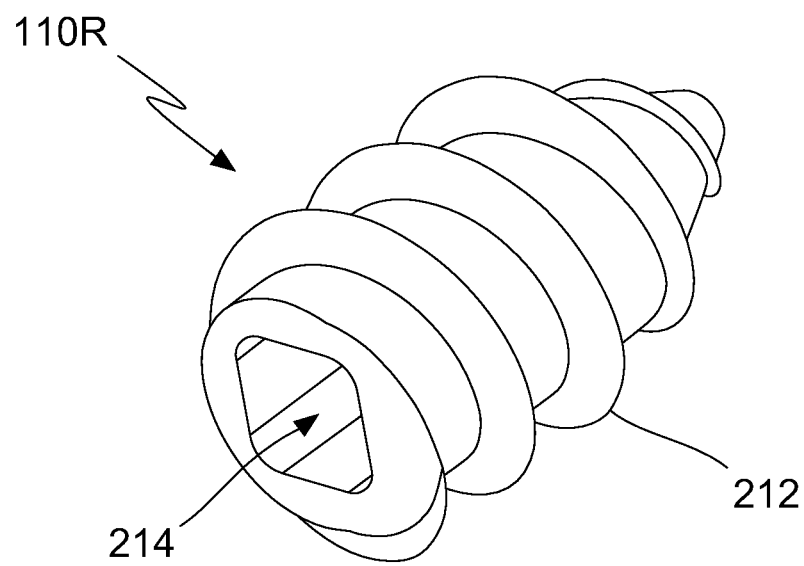
FIG. 44 illustrates an alternative configuration of an embedding implant.
Figure 45:
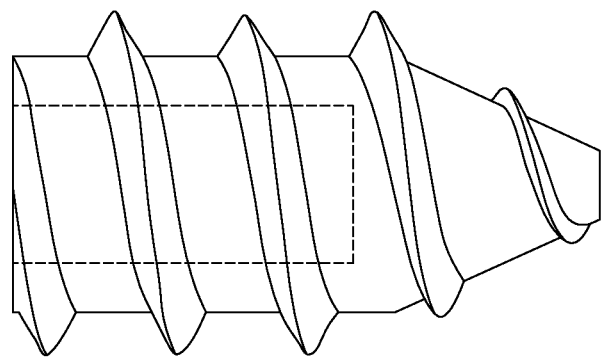
FIG. 45 illustrates an alternative view of FIG. 44.

Referring to FIGS. 44-45, embedding fastener 110 may also include thread 212. Embedding fastener 110 may be screwed and/or engaged into bondable material, tissue, and/or any other material disclosed herein, preferably by engaging interface 214 with a screw driver or other tool. Embedding fastener 110 may include an interface 214 which may be radiused, chamfered, funnel-shaped, threaded, or any other shape, for example square, rectangular, circular, elliptical, triangular, hexagonal, or asymmetrical shape. Embedding fastener 110 may be made of any metal, polymer, or other material disclosed herein.

Figure 46:
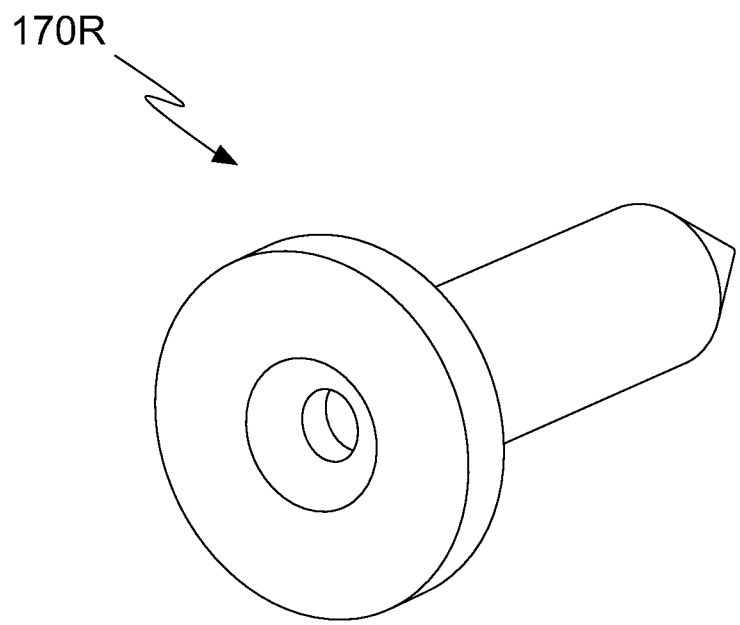
FIG. 46 illustrates an alternative configuration of a fastening implant.
Figure 47:
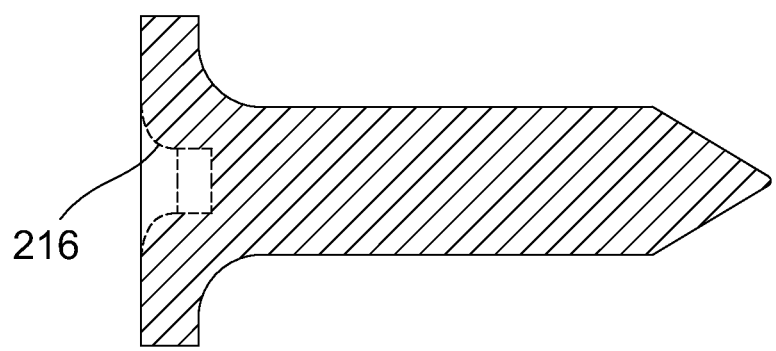
FIG. 47 illustrates an alternative view of FIG. 46.

Referring to FIGS. 46-47, fastener 170 may include effector interface 216. Preferably for engagement with end effector 104, effector interface 216 may be radiused, chamfered, funnel-shaped, threaded, or any other shape, for example square, rectangular, circular, elliptical, triangular, hexagonal, or asymmetrical shape.

Figure 48:
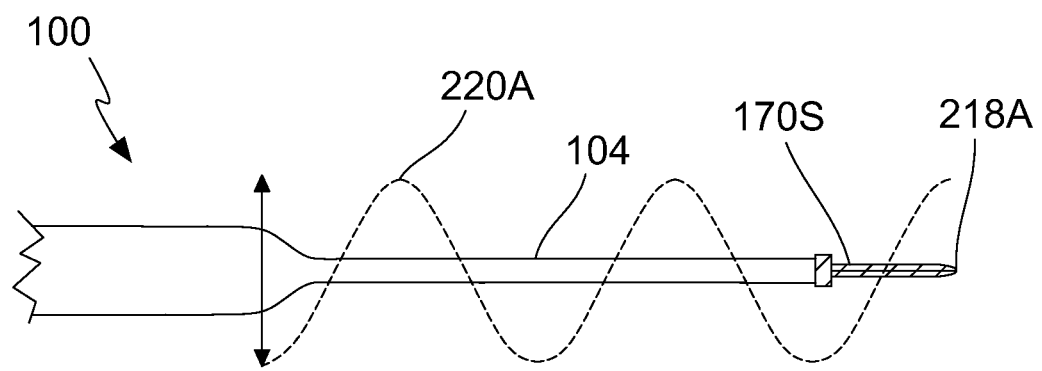
FIG. 48 illustrates an energy signal through an end effector and implant.
Figure 49:
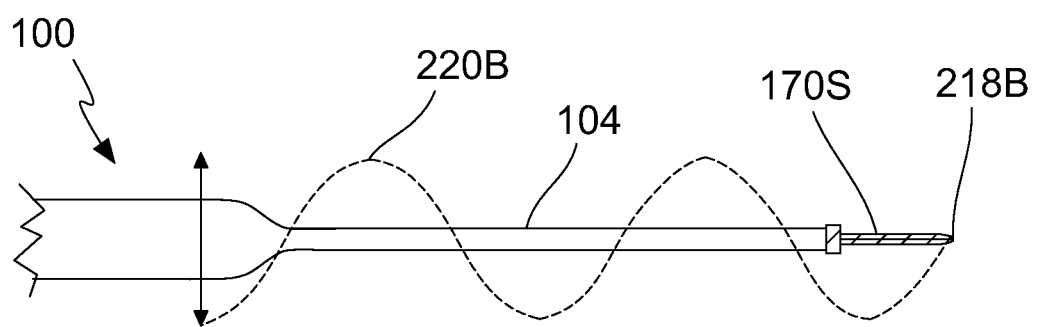
FIG. 49 illustrates an alternative configuration of an energy signal through an end effector and implant.
Figure 50:
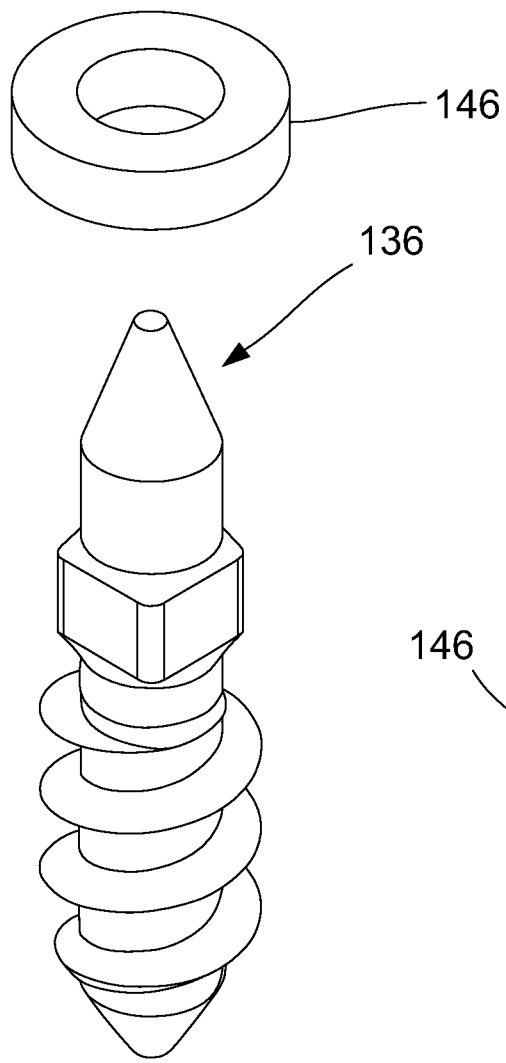
FIG. 50 illustrates an exploded view of the fastening implant of FIG. 41.
Figure 51:
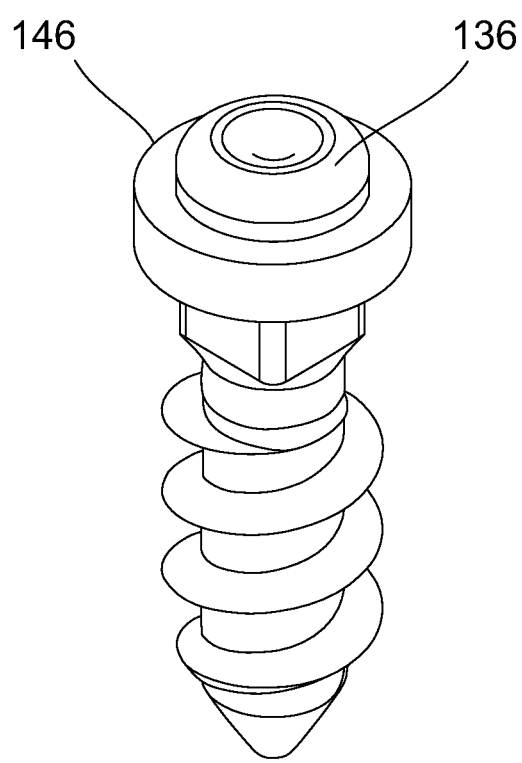
FIG. 51 illustrates the fastening implant of FIG. 50 after staking.

Referring to FIGS. 48-49, instrument 100 may include end effector 104 dimensioned and configured for a point of maximum displacement at or near the middle of fastener 170 at or near point 218B (FIG. 49). In another embodiment, it may be preferable for instrument 100 to include end effector 104 dimensioned and configured for a point of maximum displacement at or near the end of fastener 170 at or near point 218A (FIG. 48). For most applications, a point of maximum displacement at or near point 218B is preferred. Fastener 170 may be threaded or have an interference fit with end effector 104.

A point of maximum displacement along end effector 104 may occur at increments of about half its wavelength, which may be determined by the ratio of the speed of sound through the material of end effector 104 to the frequency of the wave propagated through end effector 104. The end effector 104 may be made of titanium or any material disclosed herein. For example, at a frequency of 20 khz, points of maximum displacement along end effector 104 made of titanium may be in increments of about 4 to 6 inches, preferably 4.8 to 5.1 inches. For example, at a frequency of 40 khz, points of maximum displacement along end effector 104 made of titanium may be in increments of about 2 to 3 inches, preferably 2.4 to 2.5 inches A point of maximum displacement along fastener 170 may also occur at increments of about half its wavelength. Fastener 170 may be made of PEEK, PLLA, or any material disclosed herein. As an example for PEEK, at a frequency of 20 khz, points of maximum displacement along end effector 104 may be in increments of about 1 to 2 inches, preferably 1.6 to 1.7 inches. As another example for PEEK, at a frequency of 40 khz, points of maximum displacement along end effector 104 may be in increments of about 0.5 to 1 inch, preferably 0.8 inches. As an example for PLLA, as an example at a frequency of 20 khz, points of maximum displacement along end effector 104 may be in increments of about 1 to 2 inches, preferably 1.3 to 1.4 inches. As an example for PLLA, as an example at a frequency of 40 khz, points of maximum displacement along end effector 104 may be in increments of about 0.5 to 1 inch, preferably 0.7 inches.

To optimize bonding and/or reduce the stress applied, the desired point of bonding on fastener 170 should be at or near a point of maximum displacement. For example, the desired point of bonding on fastener 170 may be along half its length or at its tip (see 218A of FIG. 48). If the desired point of bonding is at a point of minimal or zero displacement (see 218B of FIG. 49), bonding may be difficult. To facilitate bonding, it may be preferable to increase power or amplitude of the signal, thereby increasing energy applied to fastener 170.

Figure 52:
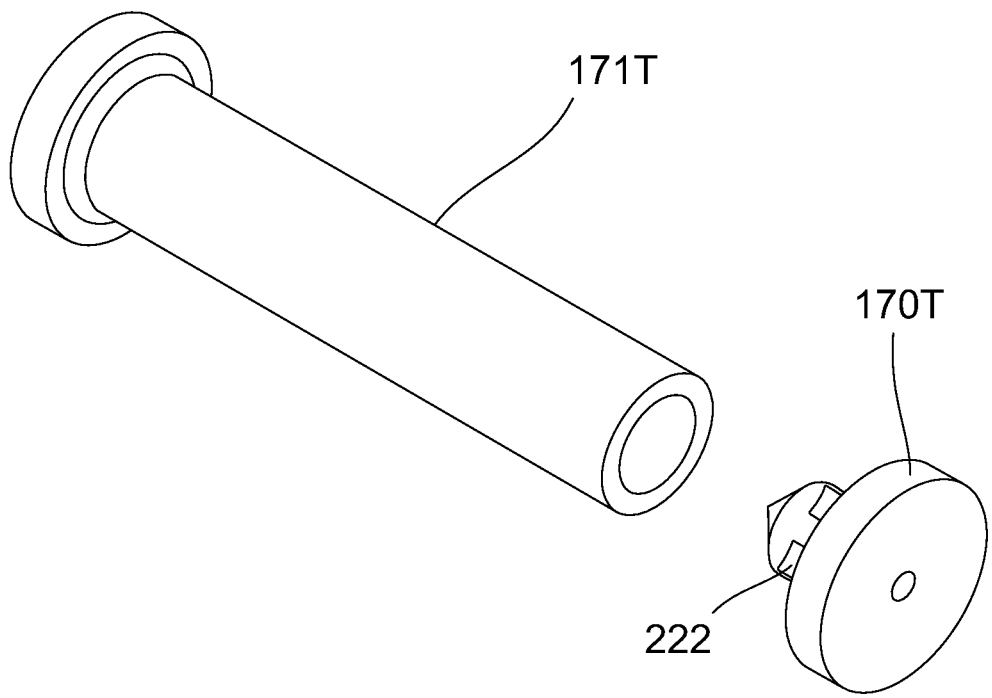
FIG. 52 illustrates an exploded view of an alternative type of fastening implant.
Figure 53:
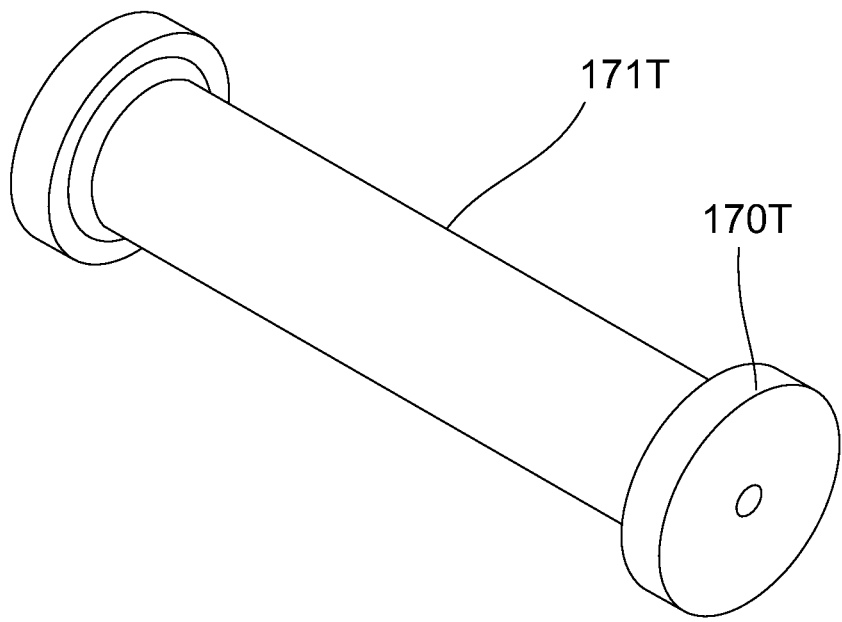
FIG. 53 illustrates an alternative view of FIG. 52.

Referring to FIGS. 52-53, fastener 170T may be used with sleeve 171T, potentially to contain and/or release therapeutic substances into a body. Fastener 170T may engage with sleeve 171T by mechanical interlock, thread, or vibratory energy bond. End effector 104 may engage with fastener 170T for vibratory energy bonding. Any fastener 170 disclosed herein may have energy director 222 to facilitate bonding by directing energy to the desired location of bonding.

Figure 54:
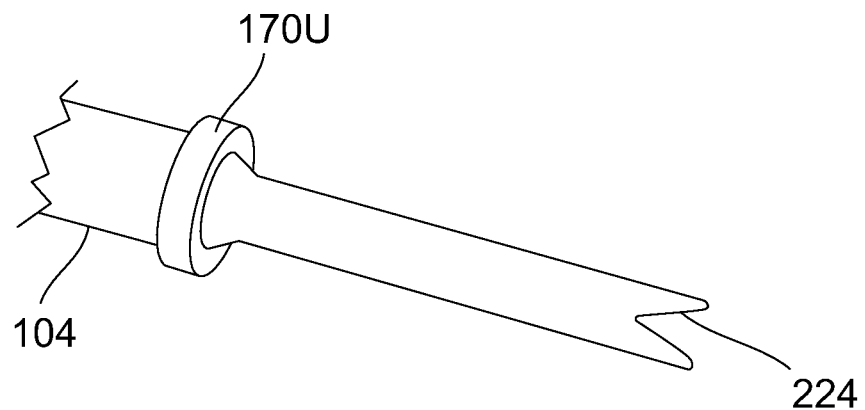
FIG. 54 illustrates an alternative configuration of a fastening implant.
Figure 55:
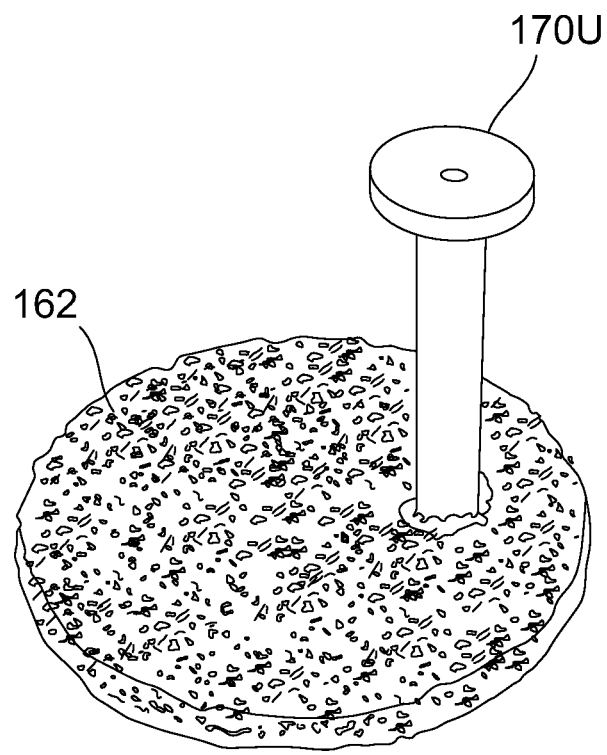
FIG. 55 illustrates the fastening implant of FIG. 54 bonded to another implant.

Referring to FIGS. 54-55, fastener 170U may have energy director 224. Energy director 224 may facilitate bonding with implant 162, especially if a portion or the entirety of implant 162 includes a porous material. For example, implant 162 may include a porous metal. End effector 104 may engage with fastener 170U for vibratory energy bonding.

Figure 56:
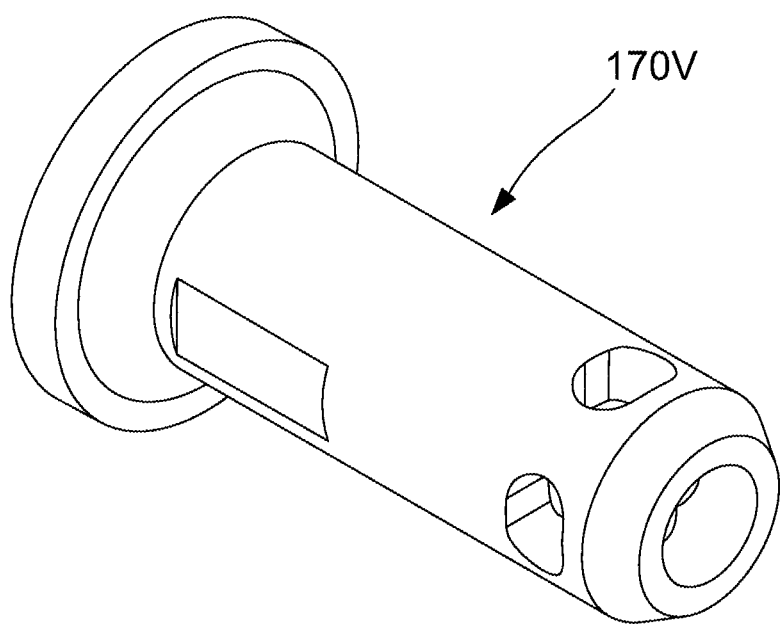
FIG. 56 illustrates an alternative configuration of a fastening implant or embedding implant.

Referring to FIG. 56, fastener 170F may be embedded into a bondable material with its leading end and stabilize a support 168 (i.e. plate) with its trailing end. End effector 104 may engage with fastener 170F, preferably near the trailing end, for vibratory energy bonding. Fastener 170F may include any material disclosed herein, but preferably titanium or titanium with at least a portion coated with PEEK or PLLA.

Figure 57:
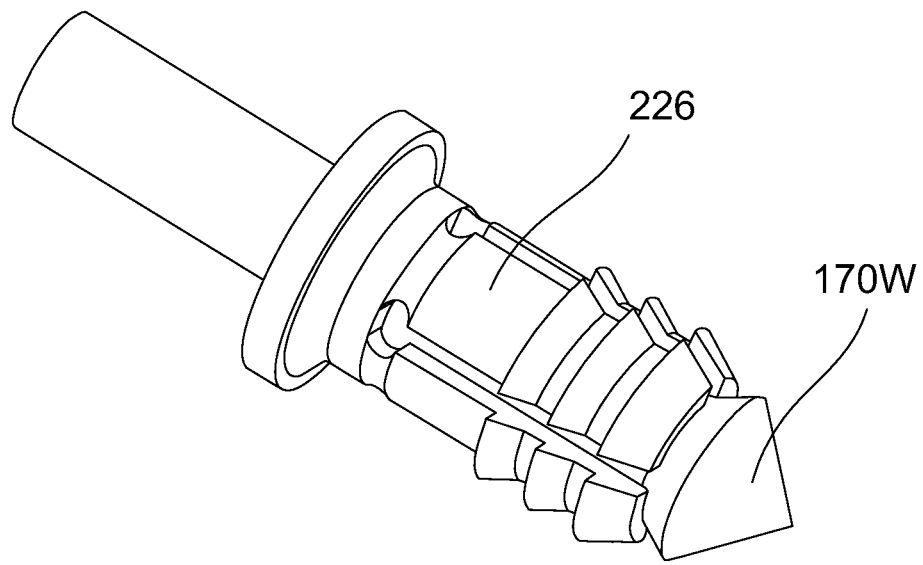
FIG. 57 illustrates an expandable configuration of a fastening implant and expanding implant.
Figure 58:
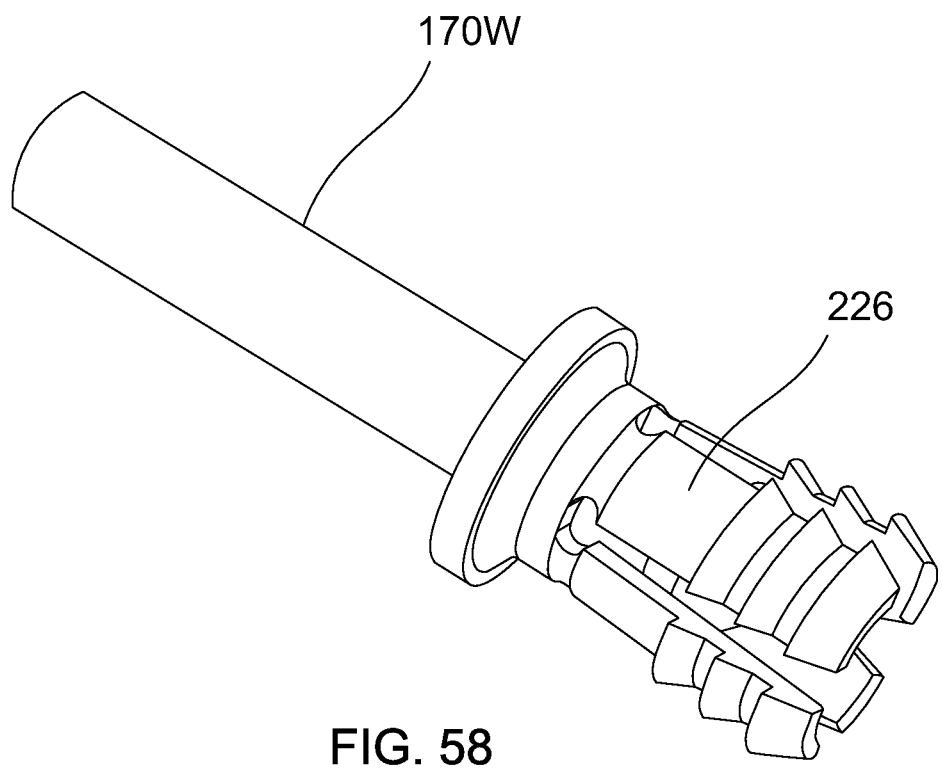
FIG. 58 illustrates an alternative view of FIG. 57.

Referring to FIGS. 57-58, fastener 170W may be used with, preferably disposed within, expanding anchor 226. End effector 104 may engage with fastener 170W, preferably near the trailing end, for vibratory energy bonding. A hole in tissue and/or bondable material may be formed or drilled into body tissue 160 prior to or during the implantation of fastener 170W and expanding anchor 226. Fastener 170W and expanding anchor 226 may pass into body tissue 160, for example in the configuration shown in FIG. 57. Fastener 170W may be retracted into expanding anchor 226, preferably after being positioned in body tissue 160. Expanding anchor 226 may expand outwards (shown in FIG. 58), thereby engaging and/or exerting a radially outward force on body tissue 160. Preferably after fastener 170W and expanding anchor 226 are in an expanded condition, vibratory energy may be applied to fastener 170W, preferably near the trailing end, to bond fastener 170W and expanding anchor 226 together. In another embodiment, fastener 170W and/or expanding anchor 226 may be configured to bond into a bondable material. After fastener 170W and expanding anchor 226 have been stabilized in the expanded configuration, the excess length of the trailing end of fastener 170W may be removed to be substantially flush with the trailing end of expanding anchor 226.

Figure 59:
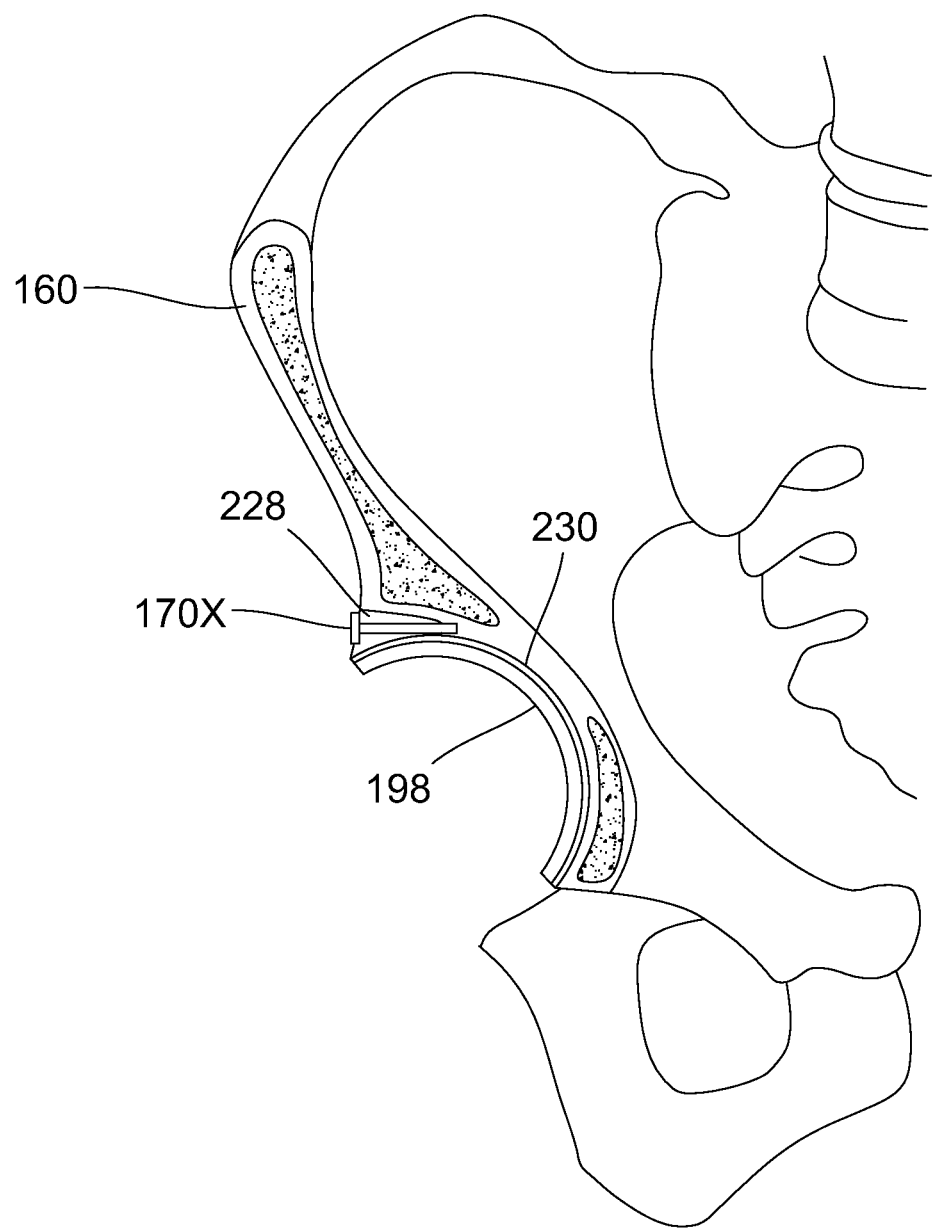
FIG. 59 illustrates an alternative configuration of an implant, interference implant, and fastening implant.

Referring to FIG. 59, fastener 170 may be used to increase interference between body tissue 160 and implant 198. Fastener 170 may be an interference screw and/or used in conjunction with interference implant 228 to position and/or stabilize implant 198. Fastener 170 may pass through all or a portion of implant 198. In additional embodiments, fastener 170 may stabilize body tissue 160 (i.e. ACL graft) against the side of a hole in body tissue 160 (i.e. bone) (not shown), stabilize body tissue 160 (i.e. soft tissue) to another body tissue 160 (i.e. bone), or stabilize interference implant 228 (or tissue graft 202) to body tissue 160 (i.e. bone) and/or implant 198 (FIG. 59). In another embodiment, fastener 170 may be part or entirely made of a biodegradable and/or bondable material. In an embodiment, fastener 170 may have a snap that would overlay part of implant 198 for interference. In another embodiment, implant 198 may include porous surface 230 (FIG. 59) or a coating of bondable material. In another example, implant 198 may be bonded with vibratory energy, hydrophilic, and/or mechanically expandable against body tissue 160 (i.e. bone), which may allow the implant to sequentially expand and provide interference against body tissue 160 (i.e. bone) or another implant.

In an embodiment related to hip (or shoulder) resurfacing, implant 198 may be an acetabular component or cup (or glenoid component), which is commonly stabilized using screws through its center. To replace the use of these screws or to provide additional stabilization, implant 198 may be stabilized by positioning fastener 170 between implant 198 and body tissue 160 (i.e. acetabulum or glenoid), which may urge implant 198 to the desired position and/or enhance interference with body tissue 160. In an embodiment, implant 198 may be free of holes, as fastener 170 may provide the majority of interference.

There are many different features to the present invention and its contemplated that these features may be used together or separately. Thus, the invention should not be limited to any particular combination of features or to a particular application of the invention. Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention.

The following is claimed:

1. A method of utilizing a bondable material to position a fastening implant in a body, said method comprising:

engaging an end effector and at least a trailing end of the fastening implant;

passing at least a portion of the end effector and the fastening implant into the body;

positioning at least a leading end surface of the fastening implant in contact with the bondable material, such that the leading end surface directly contacts the surface of the bondable material, wherein the bondable material is fixed inside the body;

applying vibratory energy to at least the trailing end of the fastening implant, thereby transmitting vibratory energy to the leading end of the fastener to soften at least a portion of the bondable material in contact with the leading end surface, such that the bondable material mechanically interlocks with at least a portion of the leading end of the fastening implant when the bondable material is solidified; and disengaging the end effector from the trailing end of the fastening implant.

2. The method of claim 1 wherein the bondable material is at least one of polymethyl methacrylate (PMMA), polyaryletherketone (PAEK), polyetheretherketone (PEEK), polyetherketoneketone (PEKK), and Poly-l-lactide (PLLA).

3. The method of claim 1 wherein at least a portion of the fastening implant is bonded into the bondable material.

4. The method of claim 1 wherein the bondable material is substantially hard before application of energy.

5. The method of claim 1 wherein at least a portion of the bondable material flows into the fastening implant to secure the at least a portion of the fastening implant to the bondable material.

6. The method of claim 1 wherein disengaging the end effector from the trailing end of the fastening implant includes rotationally disengaging the end effector from the fastening implant.

7. The method of claim 1 wherein the fastening implant includes at least a portion of titanium.

8. The method of claim 1 wherein the fastening implant includes at least a portion of at least one of stainless steel, nitinol, tantalum, porous tantalum, titanium, cobalt-chrome alloy, polyaryletherketone (PAEK), poly etheretherketone (PEEK), polyetherketoneketone (PEKK), and Poly-l-lactide (PLLA).

9. The method of claim 1 wherein the fastening implant includes at least a portion of titanium and at least a portion of a polymer.

10. The method of claim 1 wherein applying vibratory energy includes applying ultrasonic energy.

11. The method of claim 1 wherein the fastening implant stabilizes a bone of a body by embedding in a previously hardened bondable material adjacent to the bone.

12. The method of claim 1 wherein disengaging the end effector from the trailing end of the fastening implant includes disengaging the end effector from the fastening implant when the bondable material solidifies and mechanically interlocks with the fastening implant.

13. A method of utilizing a bondable material adjacent a tissue in a body, said method comprising:
passing an embedding implant and at least a portion of an end effector into the body;
positioning at least a leading end surface of the embedding implant in contact with the bondable material, such that the leading end surface directly contacts the surface of the bondable material, wherein the bondable material is fixed inside the body;
applying vibratory energy to the embedding implant to embed the embedding implant into at least a portion of the bondable material; and
engaging a fastening implant with the embedding implant to remain in the body to secure the tissue.

14. The method of claim 13 wherein embedding the embedding implant into at least a portion of the bondable material includes bonding the embedding implant to the bondable material.

15. The method of claim 13 wherein the bondable material is at least one of polymethyl methacrylate (PMMA), polyaryletherketone (PAEK), polyetheretherketone (PEEK), polyetherketoneketone (PEKK), and Poly-l-lactide (PLLA).

16. The method of claim 13 wherein applying vibratory energy includes applying ultrasonic energy.

17. The method of claim 13 wherein the bondable material has previously polymerized before positioning the embedding implant.

18. The method of claim 13 wherein applying vibratory energy includes applying vibratory energy to enable the bondable material to flow around the fastening implant.

19. The method of claim 13 wherein applying vibratory energy includes applying vibratory energy to enable the bondable material to flow into the fastening implant.

20. A method of utilizing a bondable material adjacent a tissue in a body, said method comprising:
engaging an embedding implant and an end effector;
passing the embedding implant and at least a portion of the end effector into the body;
positioning at least a leading end surface of the embedding implant in contact with the bondable material, such that the leading end surface directly contacts the surface of the bondable material, wherein the bondable material is fixed inside the body;
applying vibratory energy to the embedding implant to embed the embedding implant into at least a portion of the bondable material;
positioning a supporting implant adjacent the tissue; and
engaging a fastening implant with the embedding implant to remain in the body to secure the supporting implant adjacent the tissue.

21. The method of claim 20 wherein the embedding implant is bonded to the bondable material.

22. The method of claim 20 wherein the bondable material is at least one of polymethyl methacrylate (PMMA), polyaryletherketone (PAEK), polyetheretherketone (PEEK), polyetherketoneketone (PEKK), and Poly-l-lactide (PLLA).

23. The method of claim 20 wherein vibratory energy includes ultrasonic energy.

24. The method of claim 20 wherein the bondable material has previously polymerized before positioning the embedding implant.

25. The method of claim 20 wherein bondable material flows around the fastening implant during application of vibratory energy.

26. The method of claim 20 wherein the bondable material flows into the fastening implant during application of vibratory energy.

27. The method of claim 20 wherein the supporting implant includes a plate.

28. The method of claim 20 wherein the tissue includes a bone of the body.

* * * * *